US006953688B2

(12) United States Patent  
Ferrick et al.

(10) Patent No.: US 6,953,688 B2  
(45) Date of Patent: Oct. 11, 2005

(54) VECTOR FOR SCREENING FOR MODULATORS OF IGE SYNTHESIS, SECRETION AND SWITCH REARRANGEMENT

(75) Inventors: David A. Ferrick, Sunnyvale, CA (US); Susan E. Swift, Menlo Park, CA (US); Randall Armstrong, Hayward, CA (US); Bryan Fox, Pacifica, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 257 days.

(21) Appl. No.: 09/966,976

(22) Filed: Sep. 27, 2001

(65) Prior Publication Data

US 2002/0168649 A1 Nov. 14, 2002

Related U.S. Application Data

(63) Continuation of application No. 09/076,624, filed on May 12, 1998.

(51) Int. Cl.$^7$ ..................... C12N 15/00; C12N 15/12; C12N 15/63; C07H 21/04
(52) U.S. Cl. .............. 435/320.1; 536/23.5; 536/23.1; 536/24.1; 435/325; 435/69.1
(58) Field of Search ............................ 435/320.1, 325, 435/69.1; 536/23.5, 23.1, 24.1

(56) References Cited

U.S. PATENT DOCUMENTS

| 5,804,387 A | 9/1998 | Cormack et al. |
| 5,834,266 A | * 11/1998 | Crabtree et al. ......... 435/172.3 |
| 5,958,707 A | 9/1999 | de Vries et al. |

FOREIGN PATENT DOCUMENTS

| DE | 41 26 414 | 2/1993 |
| WO | WO 92/14836 | 9/1992 |
| WO | WO 95/25812 | 9/1995 |
| WO | WO 96/30515 | 10/1996 |
| WO | WO 96/40721 | 12/1996 |

OTHER PUBLICATIONS

Iida A, Chen ST, Friedmann T, Yee JK. J Virol. Sep. 1996; 70(9): 6054–9.*
Mikita T et al. Mol Cell Biol. Oct. 1996;16(10):5811–5820.*
Persons DA et al. Blood. Sep. 1, 1997; 90(5): 1777–86.*
Adam, et al., "Signal Transduction through a Bimolecular Receptor Tyrosine Protein Kinase Composed of a Platelet–derived Growth Factor Receptor–CD4 Chimera and the Nonreceptor Tyrosine Protein Kinase Lck," *J Biol Chem.,* 268(26):19882–19888 (1993).
Albrecht, B., et al., "A bifunctional control element in the human IgE germline promoter involved in repression and IL–4 activation," *Int. Immunol.* Aug. 1994;6(8):1143–51.
Allgood, et al., "Chimeric Receptors as Gene Switches," *Curr Opin Biotechnol.,* 8(4):474–479 (1997).

Amara, et al., "A Versatile Synthetic Dimerizer for the Regulation of Protein–Protein Interactions," *Proc Natl Acad Sci USA,* 94(20):10618–10623 (1997).
Anders, et al., "Chimeric Granulocyte/Macrophage Colony–stimulating Factor/Transforming Growth Factor–β (TGF–β) Receptors Define a Model System for Investigating the Role of Homomeric and Heteromeric Receptors in TGF–β Signaling," *J Biol Chem.,* 271(36):21758–21766 (1996).
Bazzoni, et al., "Chimeric Tumor Necrosis Factor Receptors with Constitutive Signaling Activity," *Proc Natl Acad Sci US.,* 92(12):5380 (1995).
Chen, et al., "Potentiation of Cytochrome P450/Cyclophosphamide–Based Cancer Gene Therapy By Coexpression of the P450 Reductase Gene," *Cancer Res,* 57(21):4830–4837 (Nov. 1, 1997).
Claassen et al., "Mechanism of pokeweed mitogen inhibition of rhIL–4 induced human IgE synthesis," *Cell Immunol.* 140(2):357–69 (Apr. 1992).
Cormack et al., "FACS–optimized mutants of the green fluorescent protein (GFP)," *Gene* 173:33–38 (1996).
Declercq, et al., "Dimerization of Chimeric Erythropietin/75 kDa Tumour Necrosis Factor (TNF) Receptors Transduces TNF Signals: Necessity for the 75 kDa–TNF Receptor Transmembrane Domain," *Cytokine,* 7(7):701–709 (1995).
Desai, et al., "Ligand–Mediated Negative regulation of a Chimeric Transmembrane Receptor Tyrosine Phosphatase," *Cell,* 73(3):541–554 (1993).
Ezernieks, J. et al., "The Human IgE Germline Promoter i9s Regulated by Interleukin–4, Interleukin–13, Interferon–α and Interferon–γ Via an Interferon–γ–activated Site and its Flanking Regions," Eur. J. Biochem., 240:667–673 (1996).
Ferlin, W. et al., "CD40 Signaling Induces Interleukin–4–Independent IgE Switching In Vivo," Eur. J. Immunol., 26:2911–2915 (1996).
Fiering, et al., "Single Cell Assay of Transcription Factor Reveals a Threshold in Transcription Activated By Signals Emanating From the T–Cell Antigen Receptor," *Genes Dev,* 4:1823–1834 (Oct. 1990).
Gauchat JF, et al., "Regulation of human IgE synthesis: the role of CD4+ and CD8+ T–cells and the inhibitory effects of interferon–alpha," *Eur Respir J Suppl.* 13:31s–38s (Apr. 1991).
Gauchat et al., "Regulation of germ–line epsilon transcription and induction of epsilon switching in cloned EBV–transformed and malignant human B cell lines by cytokines and CD4+ T cells," *J Immunol.* 148(7):2291–9 (Apr. 1992).
Gauchat et al., "Structure and expression of germline epsilon transcripts in human B cells induced by interleukin 4 to switch to IgE production," *J Exp Med* 172(2):463–473 (Aug. 1990).

(Continued)

*Primary Examiner*—Joseph Murphy

(57) ABSTRACT

The invention relates to methods and compositions useful in screening for modulators of IgE synthesis, secretion and switch rearrangement.

10 Claims, 28 Drawing Sheets

OTHER PUBLICATIONS

Gauchat, J.F. et al., "Modulation of II–4 Induced Germline ε RNA Syntheses in Human B Cells by Tumor Necrosis Factor–α, anti–CD40 Monoclonal Antibodies or Transforming Growth Factor–β Correlates with Levels of IgE Production," *International Immunology*, 4(3):397–406 (1992).

Gerondakis S., "Structure and expression of murine germline immunoglobulin epsilon heavy chain transcripts induced by interleukin 4," *Proc Natl Acad Sci USA*, 87(4):1581–5 (Feb. 1990).

Gonzalez–Cuadrado, et al., "Agonistic anti–Fas Antibodies Induce Glomerular Cell Apoptosis in Mice In Vivo," *Kidney Int* 51(6):1739–1746 (Jun. 1997).

Harper et al., "The p21 Cdk–Interacting Protein Cip 1 is a Potent Inhibitor of GI Cyclin–Dependent Kinases," *Cell*, 75:805–816, (Nov. 19, 1993).

Heidaran, et al., "Chimeric α– and β–Platelet– derived Growth Factor (PDGF) Receptors Define Three Immunoglobulin–like Domains of the α–PDGF Receptor that Determine PDGF–AA Binding Specificity," *J Biol Chem.*, 265(31):18741–18744 (1990).

Ichiki, T., et al., "Regulation of the expression of human C epsilon germline transcript. Identification f a novel IL–4 responsive element." *J. Immunol.* Jun. 15, 1993; 150(12):5408–17.

Jabara et al., "Induction of germ–line and mature C epsilon transcripts in human B cells stimulated with rIL–4 and EBV," *J Immunol.* 145(10):3468–73 (Nov. 1990).

Jardieu, "Anti–IgE Therapy," *Current Op. Immunol.*, 7:779–782 (1995).

Kawaguchi, et al., "Expression of Fas–estrogen Receptor Fusion Protein Induces Cell Death in pancreatic Cancer Cell Lines," *Cancer Lett.*, 116:53–59 (1997).

Kim, et al., "Construction of a Bifunctional mRNA in the Mouse By Using the Internal Ribosomal Entry Site of the Encephalomycarditis Virus," *Molecular and Cellular Biology*, 12(8):3636–3643 (Aug. 1992).

Krishnan, et al., "Dimerization of a Chimeric CD4–interferon–α Receptor Reconstitutes the Signaling Events preceding STAT Phosphorylation," *Oncogene*, 13(1):125–133 (1996).

Kumar, et al., "Human BCGF–12kD Functions as an Autocrine Growth Factor in Transformed B Cells," *Eur Cytokine Netw* 1(2):109 (1990).

Loh, R.K.S., et al., "Role of protein tyrosine kinases in CD40/interleukin–4–mediated isotype switching to IgE," *J. Allergy Clin. Immunol.* 1994 vol. 94(4):784–792.

Loh, R.K.S., et al., "Mechanisms of inhibition of IgE synthesis by nedocromil sodium: Nedocromil sodium inhibits deletional switch recombination in human B cells," *J. Allergy Clin. Immunol.* 1996 vol. 97(5):1141–1150.

Luo et al., "In vitro IgE production by interleukin 4–stimulated human peripheral blood mononuclear cells is suppressed by rapamycin," *Clin Immunol Immunopathol* 62(3):410–420 (Dec. 1991).

Mares, et al., "A Chimera Between platelet–Derived Growth Factor β–Receptor and Fibroblast Growth Factor Receptor–1 Stimulates Pancreatic β–Cell DNA Synthesis in the Presence of PDGF–BB," *Growth Factors*, 6(2):93–101 (1992).

Wang, et al., "UCN–01: A Potent Abrogator of G2 Checkpoint Function in Cancer Cells with Dirupted p53," *J Natl Cancer Inst*, 88(14):956–965 (1996).

Xu et al., "Replacement of germ–line ε promoter by gene targeting alters control of immunoglobulin heavy chain class switching," *Proc. Natl. Acad. Sci. USA* 90:3705–3709 (Apr. 1993).

* cited by examiner

CTCGAGGACAGTGACCTGGGAGTGAGTACAAGGTGAGGCCACCACTCAGGGT
GCCAGCTCCAAGCGGGTCACAGGGACGAGGGCTGCGGCCATCAGGAGGCCCT
GCACACATCTGGGACACGCGCCCCGAGGGCCAGTTCACCTCAGTGCGCC
TCATTCTCCTGCACAAAAGCGCCCCATCCTTTCTTCACAAGGCTTTCGTGG
AAGCAGAGGCGTCGATGCCCAGTACCTCTCCCTTTCCCAGGCAACGGGACC
CCAAGTTTGCTGACTGGGACCACCAAGCCACGCATGCGTCAAGAGTGAGAGT
CCGGGACCTAGGCAGGGGCCCTGGGGTTGGGCCTGAGAGAGAAGAGAACCTC
CCCCAGCACTCGGTGTGCATCGGTAGTGAAGGAGCCTCACCTGACCCCCGCT
GTTGCTCAATCGACTTCCCAAGAACAGAGAGAAAAGGGAACTTCCAGGGCGG
CCCGGGCCTCCTGGGGGTTCCCACCCCATTTTTAGCTGAAAGCACTGAGGCA
GAGCTCCCCTACCCAGGCTCCACTGCCCGGCACAGAAATAACAACCACGGT
TACTGATCATCTGGGAGCTGTCCAGGAATTC

FIG._1A

```
  1  GCTGGGCTAA ACTGGGCTAG CCTGAGCTGG GCTGAACTGG GCTGCTGGGC
 51  TGGACTGGGT AAGCTGGGCT GAGCTGGGTT GGGTGGAAAT GGGCTGAGCT
101  GAGCTAGGCT AAACTGGGTT TGGCTGGGCT GGGCTGGGCT GGG
```

FIG._2B

```
  1  GGTTTGGCTG GGCTGGGCTG GGCTGGGCTG GGTTCAGCTG AGCGGGTTGG
 51  GTTAGACTGG GTCAAACTGG TTCAGC
```

FIG._2C

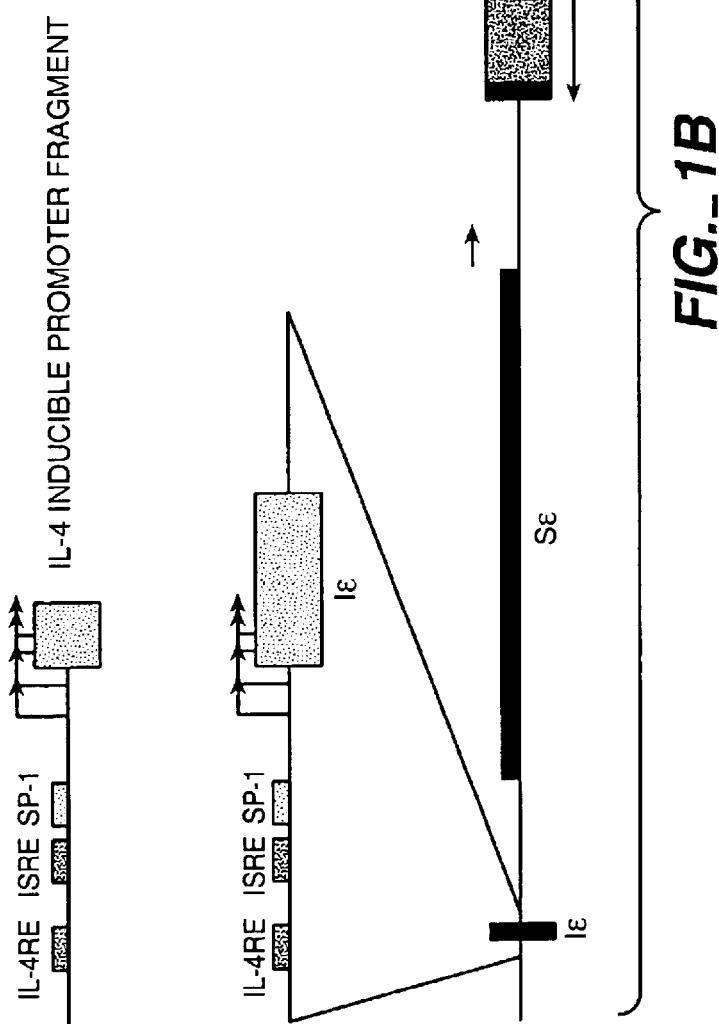
FIG._1B

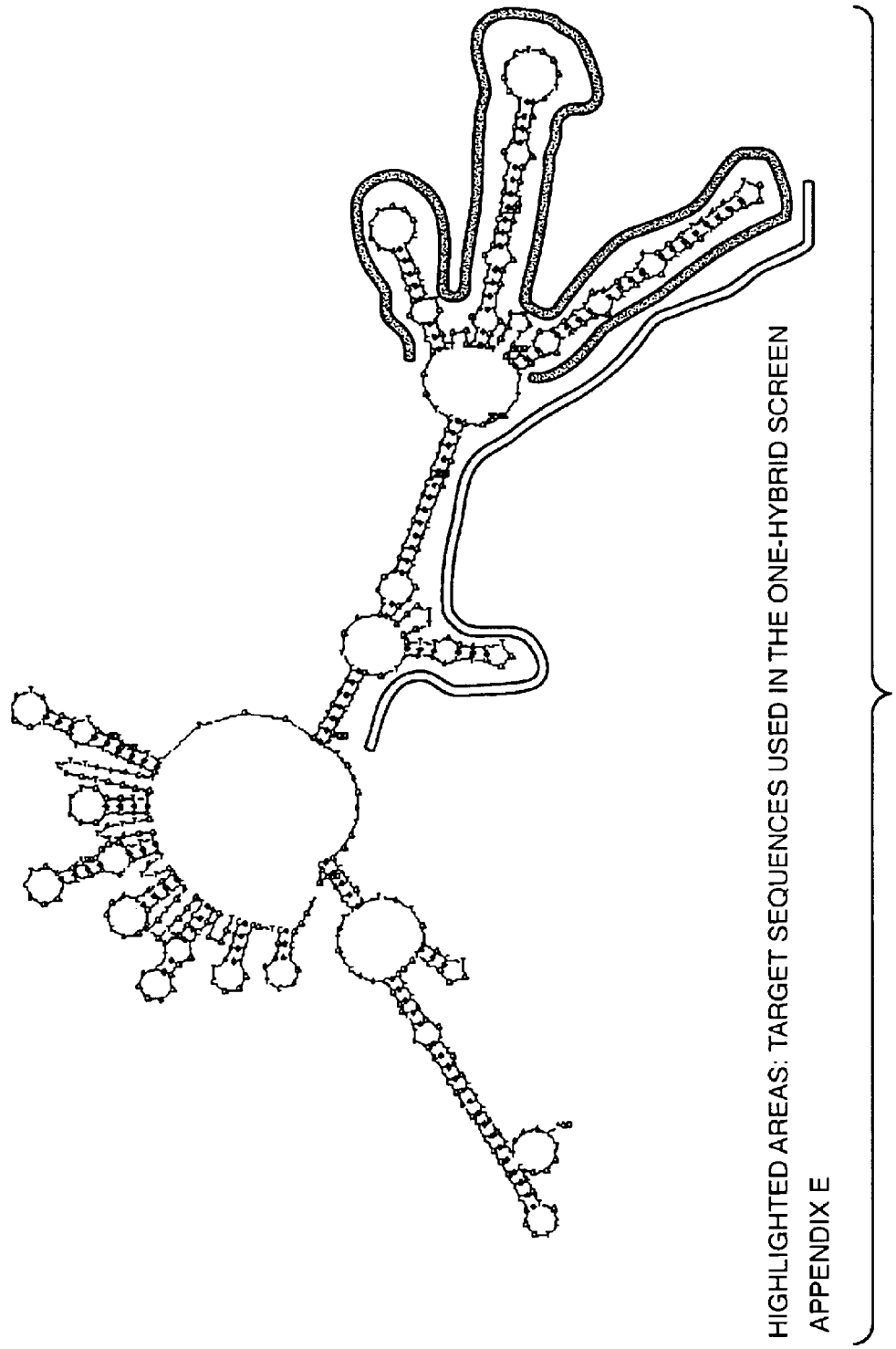
LOW ENERGY DNA FOLDING OF THE Sε REGION
HIGHLIGHTED AREAS: TARGET SEQUENCES USED IN THE ONE-HYBRID SCREEN
APPENDIX E
FIG._2A

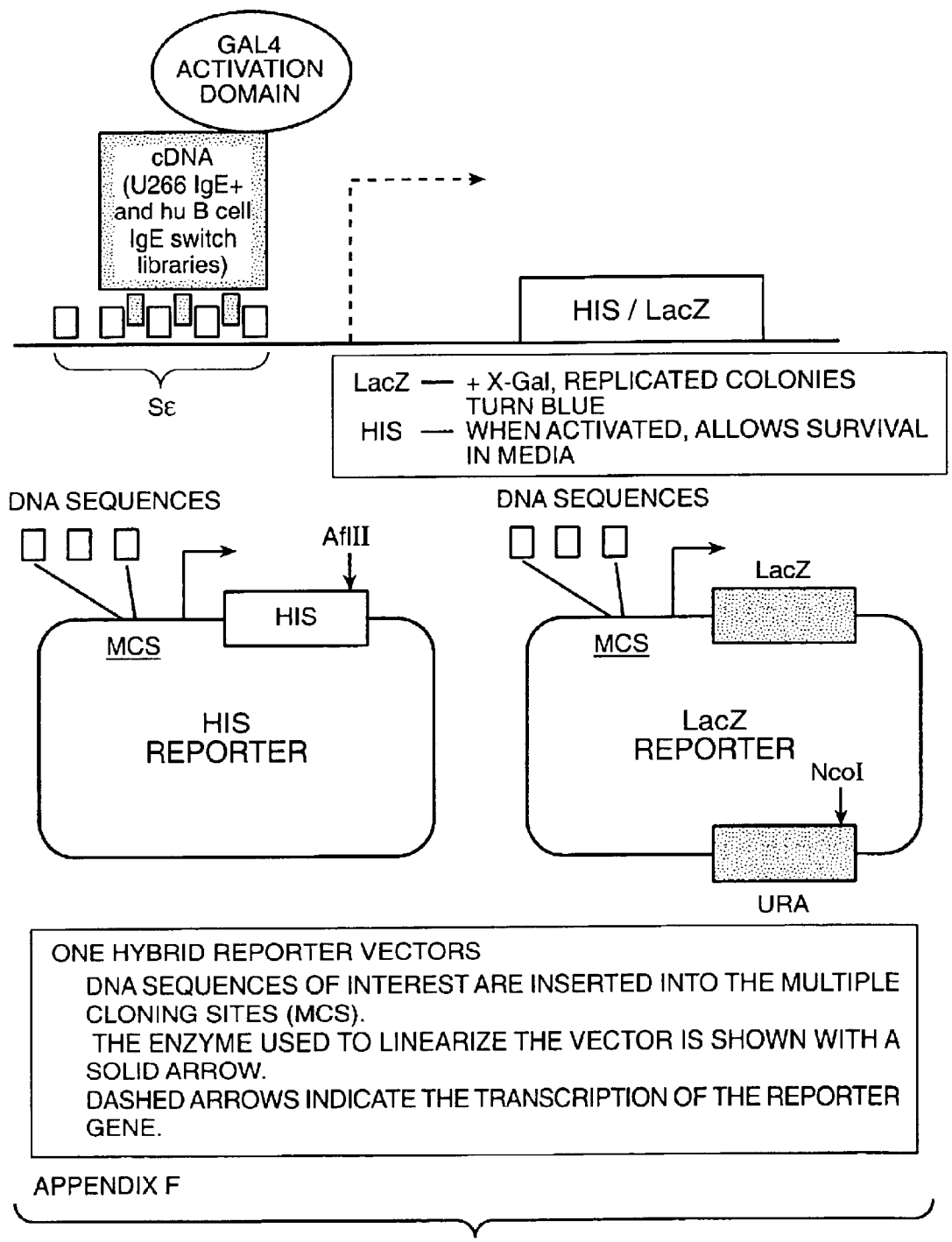
FIG._3

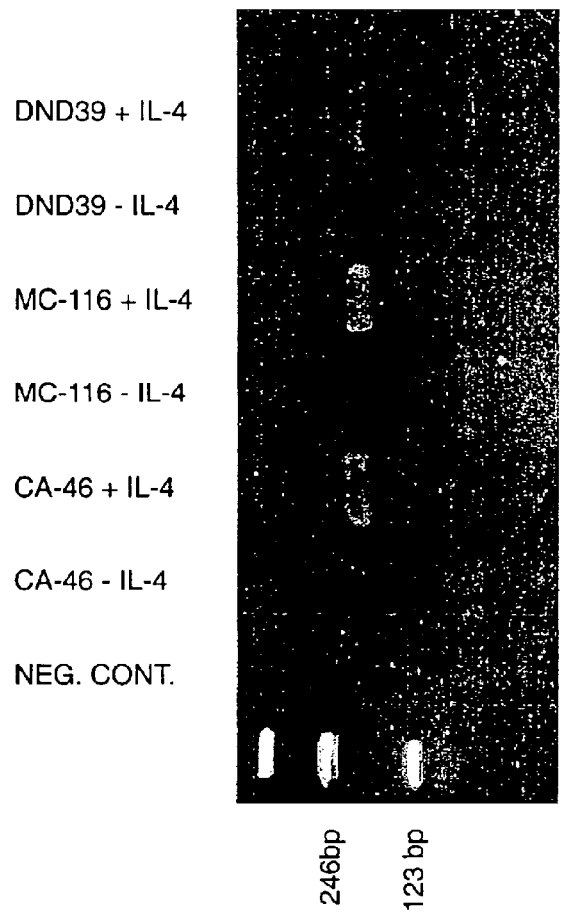
FIG._4
IL-4 INDUCTION OF GERMLINE ε mRNA IN THE IgM + B CELL LINES: CA-46, MC-116 AND DND39
CELLS WERE INCUBATED FOR 48 HRS. IN 300 U / ml OF h-IL-4. RT-PCR WAS PERFORMED USING PRIMERS SPECIFIC FOR THE GERMLINE ε EXON AND THE 5'-END OF THE Cε CH1 EXON (PREDICTED SIZE ~ 200 bp).
APPENDIX G

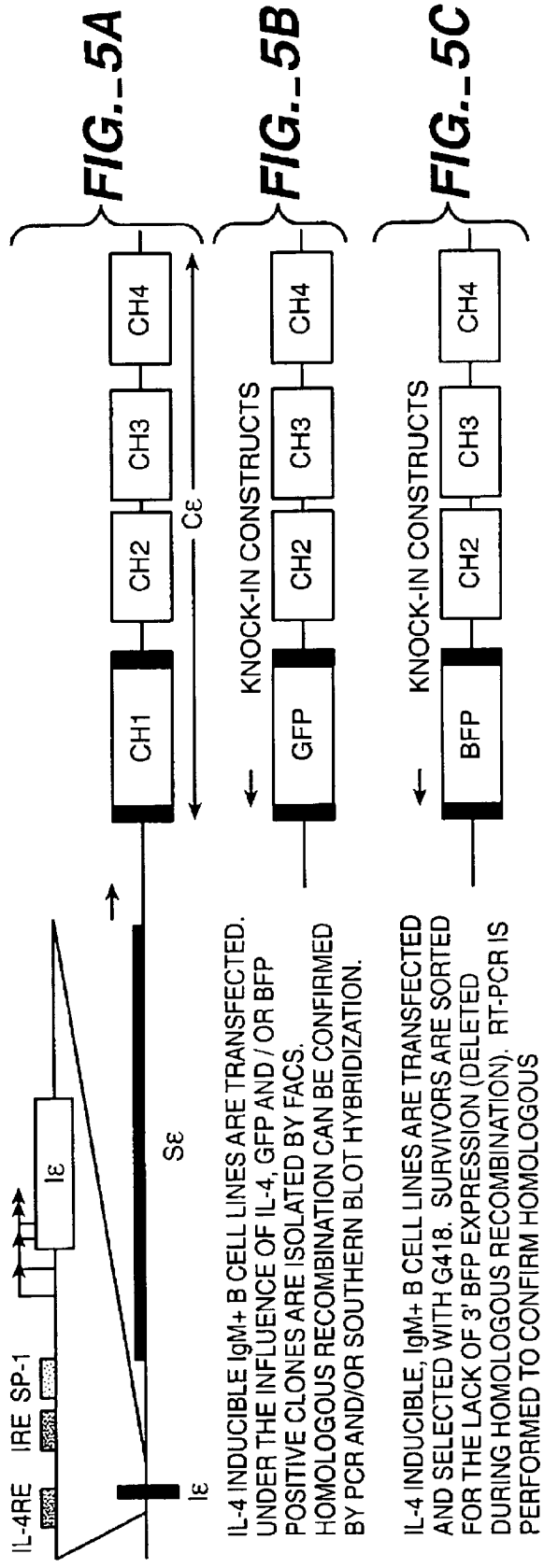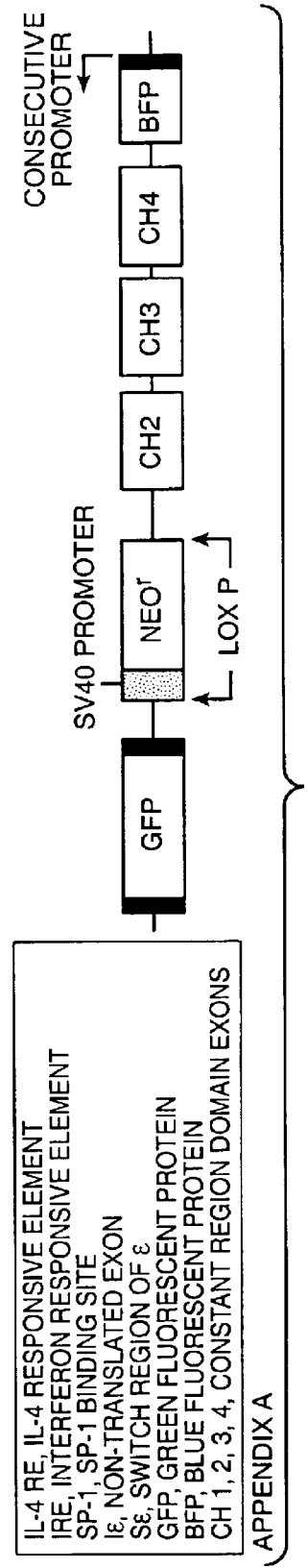

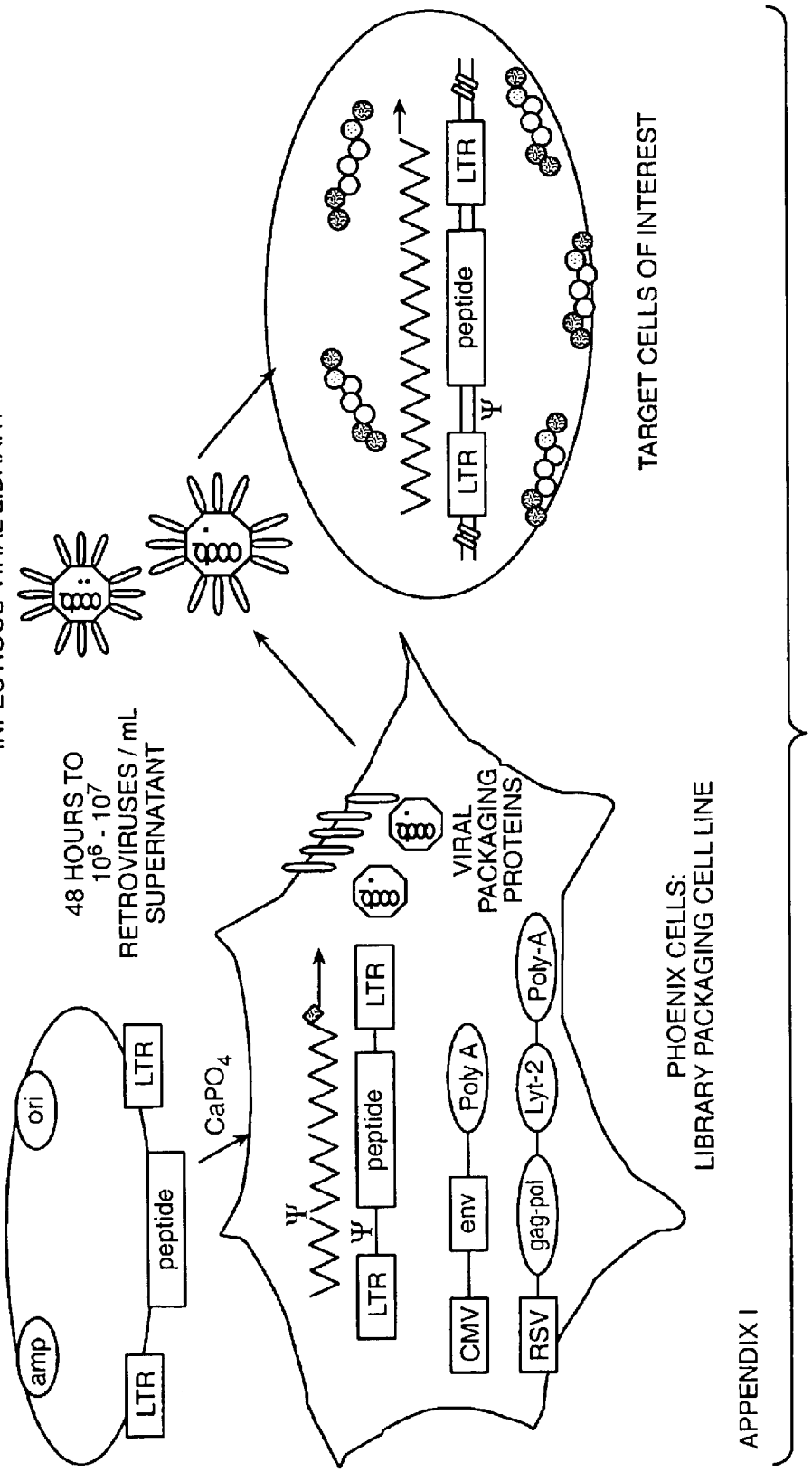
FIG._7

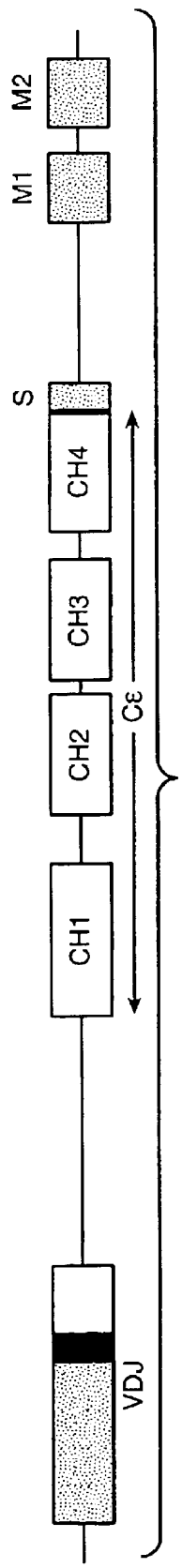
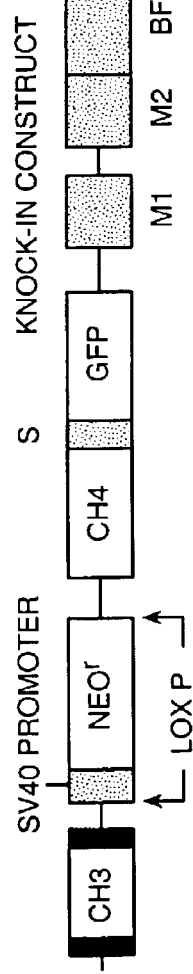
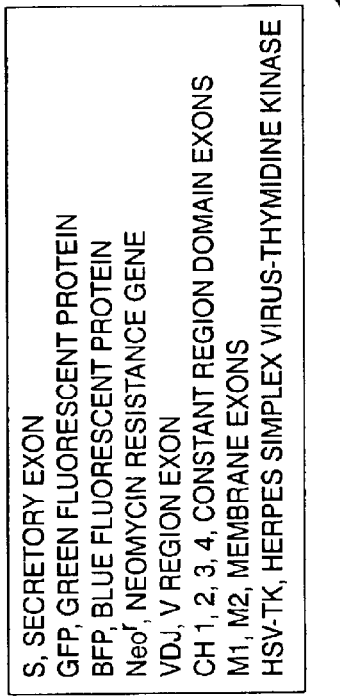

FIG. 8A ε HEAVY CHAIN GFP / BFP KNOCK-IN CELL LINE

FIG. 8B

S, SECRETORY EXON
GFP, GREEN FLUORESCENT PROTEIN
BFP, BLUE FLUORESCENT PROTEIN
Neo$^r$, NEOMYCIN RESISTANCE GENE
VDJ, V REGION EXON
CH 1, 2, 3, 4, CONSTANT REGION DOMAIN EXONS
M1, M2, MEMBRANE EXONS
HSV-TK, HERPES SIMPLEX VIRUS-THYMIDINE KINASE

U266 CELLS ARE TRANSFECTED AND SELECTED WITH G418. SURVIVORS ARE TREATED WITH GANCICLOVIR (HSV-TK DELETED DURING HOMOLOGOUS RECOMBINATION). RT-PCR IS PERFORMED TO CONFIRM HOMOLOGOUS RECOMBINATION. THOSE CLONES ARE TRANSFECTED WITH cre TO REMOVE THE SV40 NEOMYCIN RESISTANCE GENE.

APPENDIX D

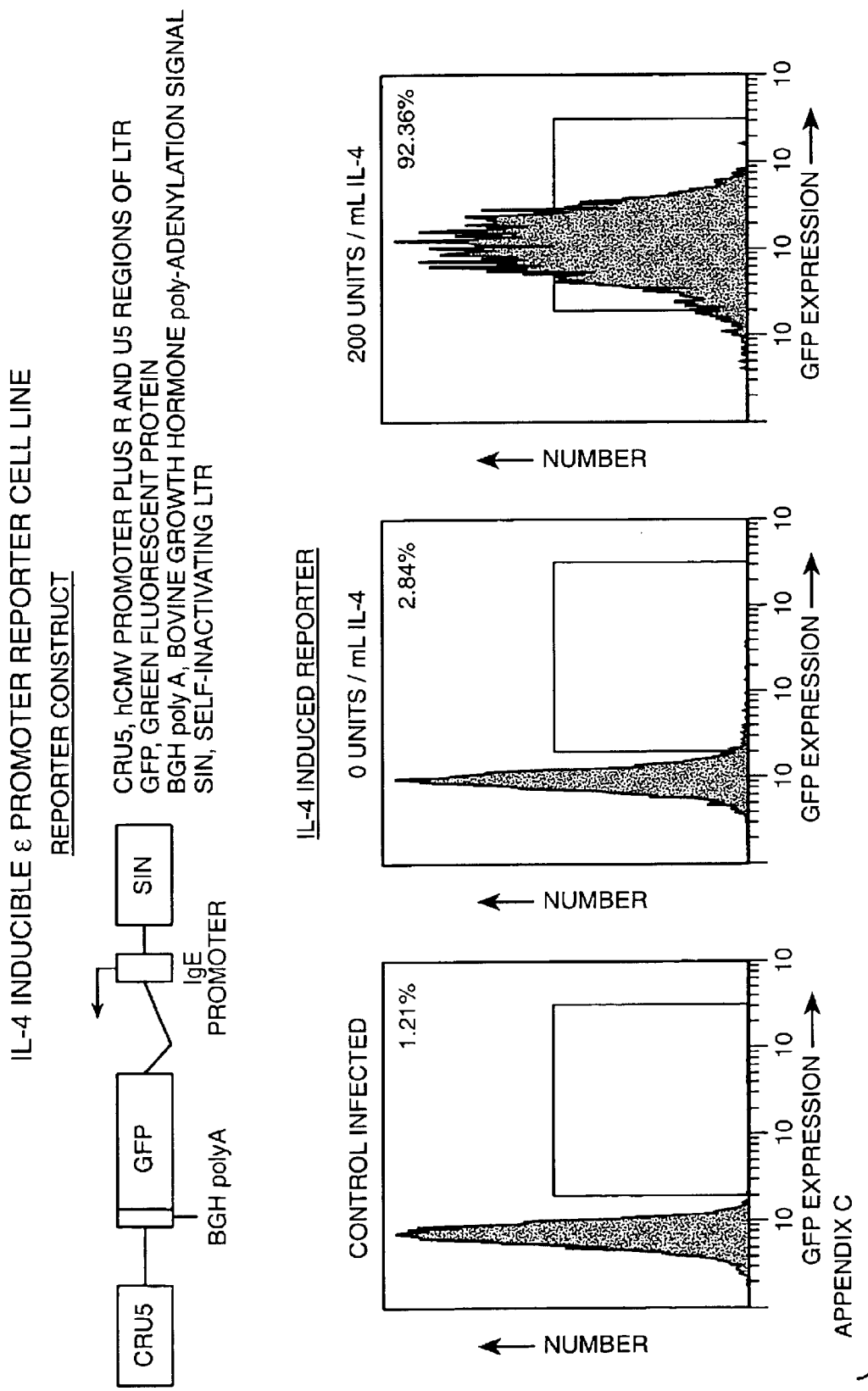
FIG._9A

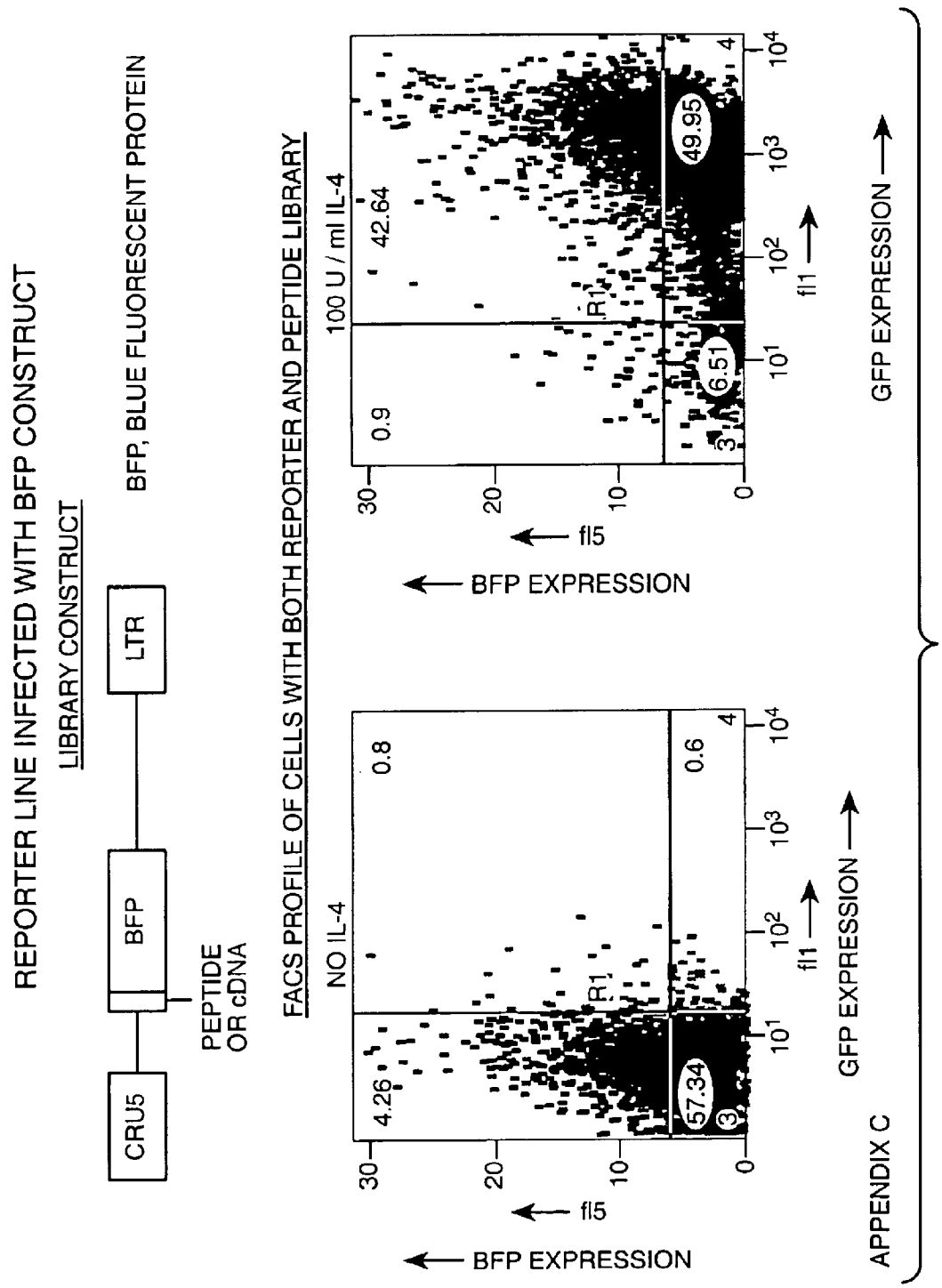
FIG._9B

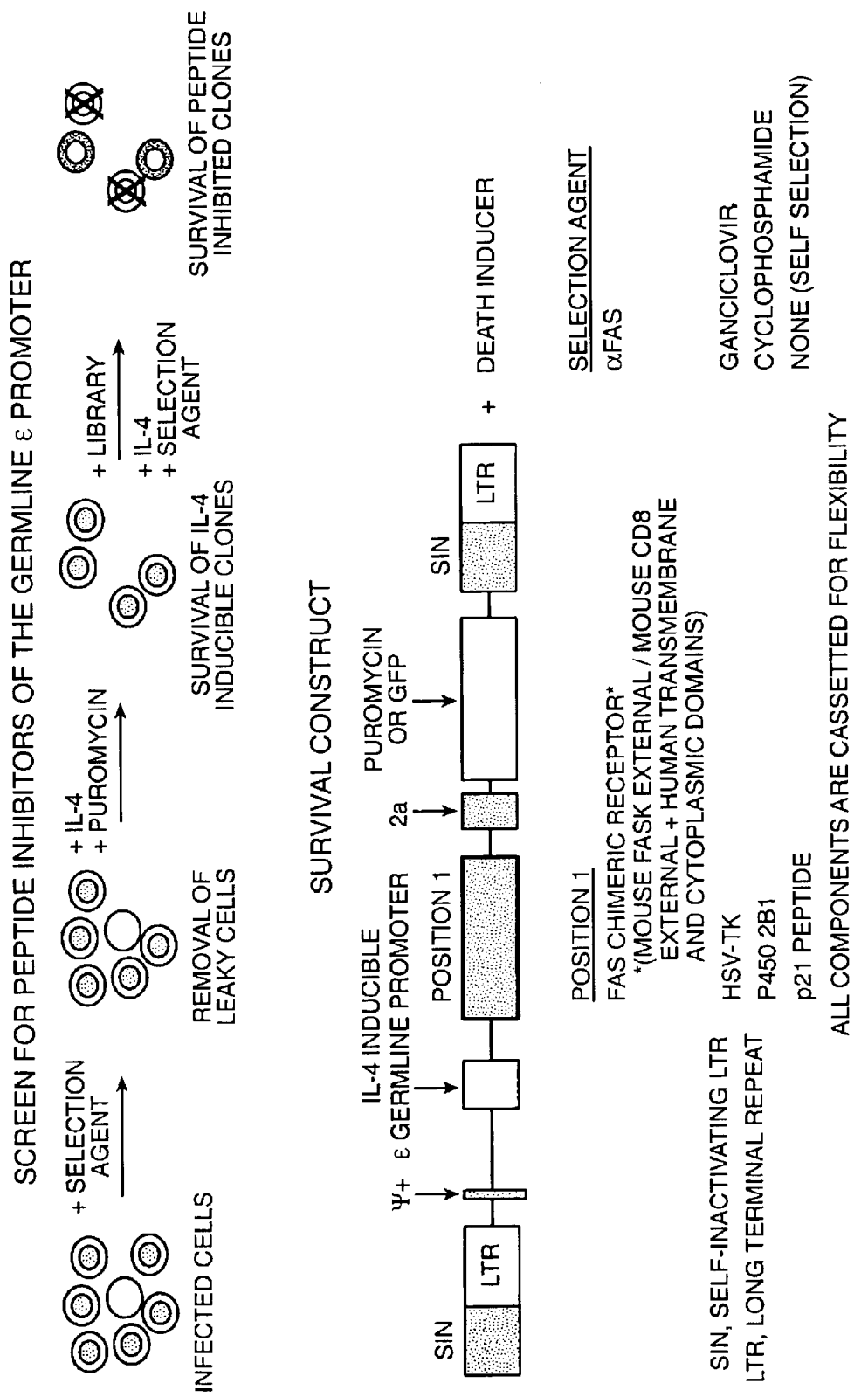
FIG._10

1-845    CMV promoter/R/U5 5' LTR
1322     GAG ATG-ATC mutation
850-2100 extended Ψ region
2146-2173 two Bstxl peptide cloning sites
2205-2723 ECMV IRES (cloned as EcoR1/Mscl fragment from
         pCITE-4a [Novagen])
2746-3465 GFP coding region
3522-4115 3' LTR
4122-6210 pGEM backbone (pUC origin, ampR)

```
ATCACGAGGCCCTTTCGTCTTCAAGAACAGCTTTGCTCTTAGGAGTTTCCTAATACATCC
CAAACTCAAATATATAAAGCATTTGACTTGTTCTATGCCCTAGTTATTAATAGTAATCAA
TTACGGGGTCATTAGTTCATAGCCCATATATGGAGTTCCGCGTTACATAACTTACGGTAA
ATGGCCCGCCTGGCTGACCGCCCAACGACCCCGCCCATTGACGTCAATAATGACGTATG
TTCCCATAGTAACGCCAATAGGGACTTTCCATTGACGTCAATGGGTGGAGTATTTACGGT
AAACTGCCCACTTGGCAGTACATCAAGTGTATCATATGCCAAGTACGCCCCCTATTGACG
TCAATGACGGTAAATGGCCCGCCTGGCATTATGCCCAGTACATGACCTTATGGGACTTTC
CTACTTGGCAGTACATCTACGTATTAGTCATCGCTATTACCATGGTGATGCGGTTTTGGC
AGTACATCAATGGGCGTGGATAGCGGTTTGACTCACGGGGATTTCCAAGTCTCCACCCCA
TTGACGTCAATGGGAGTTTGTTTTGGCACCAAAATCAACGGGACTTTCCAAAATGTCGTA
ACAACTCCGCCCCATTGACGCAAATGGGCGGTAGGCATGTACGGTGGGAGGTCTATATAA
GCAGAGCTCAATAAAAGAGCCCACAACCCCTCACTCGGGGCGCCAGTCCTCCGATTGACT
GAGTCGCCCGGGTACCCGTGTATCCAATAAACCCTCTTGCAGTTGCATCCGACTTGTGGT
CTCGCTGTTCCTTGGGAGGGTCTCCTCTGAGTGATTGACTACCCGTCAGCGGGGGTCTTT
CATTTGGGGGCTCGTCCGGGATCGGGAGACCCCTGCCCAGGGACCACCGACCCACCACCG
GGAGGTAAGCTGGCCAGCAACTTATCTGTGTCTGTCCGATTGTCTAGTGTCTATGACTGA
TTTTATGCGCCTGCGTCGGTACTAGTTAGCTAACTAGCTCTGTATCTGGCGGACCCGTGG
TGGAACTGACGAGTTCGGAACACCCGGCCGCAACCCTGGGAGACGTCCCAGGGACTTCGG
GGGCCGTTTTTGTGGCCCGACCTGAGTCCAAAAATCCCGATCGTTTTGGACTCTTTGGTG
CACCCCCCTTAGAGGAGGGATATGTGGTTCTGGTAGGAGACGAGAACCTAAAACAGTTCC
CGCCTCCGTCTGAATTTTTGCTTTCGGTTTGGGACCGAAGCCGCGCCGCGCGTCTTGTCT
GCTGCAGCATCGTTCTGTGTTGTCTCTGTCTGACTGTGTTTCTGTATTTGTCTGAAAATA
TCGGCCCGGGCCAGACTGTTACCACTCCCTTAAGTTTGACCTTAGGTCACTGGAAAGATG
TCGAGCGGATCGCTCACAACCAGTCGGTAGATGTCAAGAAGAGACGTTGGGTTACCTTCT
GCTCTGCAGAATGGCCAACCTTTAACGTCGGATGGCCGCGAGACGGCACCTTTAACCGAG
ACCTCATCACCCAGGTTAAGATCAAGGTCTTTTCACCTGGCCCGCATGGACACCCAGACC
AGGTCCCCTACATCGTGACCTGGGAAGCCTTGGCTTTTGACCCCCCTCCCTGGGTCAAGC
CCTTTGTACACCCTAAGCCTCCGCCTCCTCTTCCTCCATCCGCCCCGTCTCTCCCCCTTG
AACCTCCTCGTTCGACCCCGCCTCGATCCTCCCTTTATCCAGCCCTCACTCCTTCTCTAG
GCGCCCCCATATGGCCATATGAGATCTTATATGGGGCACCCCCGCCCCTTGTAAACTTCC
CTGACCCTGACATGACAAGAGTTACTAACAGCCCCTCTCTCCAAGCTCACTTACAGGCTC
TCTACTTAGTCCAGCACGAAGTCTGGAGACCTCTGGCGGCAGCCTACCAAGAACAACTGG
ACCGACCGGTGGTACCTCACCCTTACCGAGTCGGCGACACAGTGGGTCCGCCGACACC
AGACTAAGAACCTAGAACCTCGCTGGAAAGGACCTTACACAGTCCTGCTGACCACCCCA
CCGCCCTCAAAGTAGACGGCATCGCGCTTGGATACACGCCGCCCACGTGAAGGCTGCCGA
CCCCGGGGGTGGACCATCCTCTAGACTGCCGGATCTCGAGGGATCCACCACCATGGACCC
CCATTAAATTGGAATTCCTGCAGCCCGGGGGATCCACTAGTTCTAGAGCGAATTAATTCC
```

FIG._11A-1

```
GGTTATTTTCCACCATATTGCCGTCTTTTGGCAATGTGAGGGCCCGGAAACCTGGCCCTG
TCTTCTTGACGAGCATTCCTAGGGGTCTTTCCCTCTCGCCAAAGGAATGCAAGGTCTGT
TGAATGTCGTGAAGGAAGCAGTTCCTCTGGAAGCTTCTTGAAGACAAACAACGTCTGTAG
CGACCCTTTGCAGGCAGCGGAACCCCCACCTGGCGACAGGTGCCTCTGCGGCCAAAAGC
CACGTGTATAAGATACACCTGCAAAGGCGGCACAACCCCAGTGCCACGTTGTGAGTTGGA
TAGTTGTGGAAAGAGTCAAATGGCTCTCCTCAAGCGTATTCAACAAGGGGCTGAAGGATG
CCCAGAAGGTACCCCATTGTATGGGATCGATCTGGGGCCTCGGTGCACATGCTTTACAT
GTGTTTAGTCGAGGTTAAAAAACGTCTAGGCCCCCCGAACCACGGGGACGTGGTTTTCCT
TTGAAAAACACGATGATAATATGGGGATCCACCGGTCGCCACCATGGTGAGCAAGGGCG
AGGAGCTGTTCACCGGGGTGGTGCCCATCCTGGTCGAGCTGGACGGCGACGTAAACGGCC
ACAAGTTCAGCGTGTCCGGCGAGGGCGAGGGCGATGCCACCTACGGCAAGCTGACCCTGA
AGTTCATCTGCACCACCGGCAAGCTGCCCGTGCCCTGGCCCACCCTCGTGACCACCCTGA
CCTACGGCGTGCAGTGCTTCAGCCGCTACCCCGACCACATGAAGCAGCACGACTTCTTCA
AGTCCGCCATGCCCGAAGGCTACGTCCAGGAGCGCACCATCTTCTTCAAGGACGACGGCA
ACTACAAGACCCGCGCCGAGGTGAAGTTCGAGGGCGACACCCTGGTGAACCGCATCGAGC
TGAAGGGCATCGACTTCAAGGAGGACGGCAACATCCTGGGGCACAAGCTGGAGTACAACT
ACAACAGCCACAACGTCTATATCATGGCCGACAAGCAGAAGAACGGCATCAAGGTGAACT
TCAAGATCCGCCACAACATCGAGGACGGCAGCGTGCAGCTCGCCGACCACTACCAGCAGA
ACACCCCCATCGGCGACGGCCCCGTGCTGCTGCCCGACAACCACTACCTGAGCACCCAGT
CCGCCCTGAGCAAAGACCCCAACGAGAAGCGCGATCACATGGTCCTGCTGGAGTTCGTGA
CCGCCGCCGGGATCACTCTCGGCATGGACGAGCTGTACAAGTAAAGCGGCCGCTCGACGA
TAAAATAAAAGATTTTATTTAGTCTCCAGAAAAAGGGGGGAATGAAAGACCCCACCTGTA
GGTTTGGCAAGCTAGCTTAAGTAACGCCATTTTGCAAGGCATGGAAAAATACATAACTGA
GAATAGAGAAGTTCAGATCAAGGTCAGGAACAGATGGAACAGCTGAATATGGGCCAAACA
GGATATCTGTGGTAAGCAGTTCCTGCCCCGGCTCAGGGCCAAGAACAGATGGAACAGCTG
AATATGGGCCAAACAGGATATCTGTGGTAAGCAGTTCCTGCCCCGGCTCAGGGCCAAGAA
CAGATGGTCCCCAGATGCGGTCCAGCCCTCAGCAGTTTCTAGAGAACCATCAGATGTTTC
CAGGGTGCCCCAAGGACCTGAAATGACCCTGTGCCTTATTTGAACTAACCAATCAGTTCG
CTTCTCGCTTCTGTTCGCGCGCTTCTGCTCCCCGAGCTCAATAAAAGAGCCCACAACCCC
TCACTCGGGGCGCCAGTCCTCCGATTGACTGAGTCGCCCGGGTACCCGTGTATCCAATAA
ACCCTCTTGCAGTTGCATCCGACTTGTGGTCTCGCTGTTCCTTGGGAGGGTCTCCTCTGA
GTGATTGACTACCCGTCAGCGGGGGTCTTTCATTTCCGACTTGTGGTCTCGCTGCCTTGG
GAGGGTCTCCTCTGAGTGATTGACTACCCGTCAGCGGGGTCTTCACATGCAGCATGTAT
CAAAATTAATTTGGTTTTTTTTCTTAAGTATTTACATTAAATGGCCATAGTTGCATTAAT
GAATCGGCCAACGCGCGGGGAGAGGCGGTTTGCGTATTGGCGCTCTTCCGCTTCCTCGCT
CACTGACTCGCTGCGCTCGGTCGTTCGGCTGCGGCGAGCGGTATCAGCTCACTCAAAGGC
GGTAATACGGTTATCCACAGAATCAGGGGATAACGCAGGAAAGAACATGTGAGCAAAAGG
CCAGCAAAAGGCCAGGAACCGTAAAAAGGCCGCGTTGCTGGCGTTTTTCCATAGGCTCCG
CCCCCCTGACGAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTGT
GCACGAACCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGGCTACAC
```

FIG._11A-2

```
TAGAAGGACAGTATTTGGTATCTGCGCTCTGCTGAAGCCAGTTACCTTCGGAAAAAGAGT
TGGTAGCTCTTGATCCGGCAAACAAACCACCGCTGGTAGCGGTGGTTTTTTTGTTTGCAA
GCAGCAGATTACGCGCAGAAAAAAGGATCTCAAGAAGATCCTTTGATCTTTTCTACGGG
GTCTGACGCTCAGTGGAACGAAAACTCACGTTAAGGGATTTTGGTCATGAGATTATCAAA
AAGGATCTTCACCTAGATCCTTTTAAATTAAAAATGAAGTTTGCGCAAATCAATCTAAAG
TATATATGAGTAAACTTGGTCTGACAGTTACCAATGCTTAATCAGTGAGGCACCTATCTC
AGCGATCTGTCTATTTCGTTCATCCATAGTTGCCTGACTCCCCGTCGTGTAGATAACTAC
GATACGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAAGTGG
TCCTGCAACTTTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCATCGTGGTGTC
ACGCTCGTCGTTTGGTATGGCTTCATTCAGCTCCGGTTCCCAACGATCAAGGCGAGTTAC
ATGATCCCCCATGTTGTGCAAAAAAGCGGTTAGCTCCTTCGGTCCTCCGATCGTTGTCAG
AAGTAAGTTGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAGTCATTCTG
AGAATAGTGTATGCGGCGACCGAGTTGCTCTTGCCCGGCGTCAACACGGGATAATACCGC
GCCACATAGCAGAACTTTAAAAGTGCTCATCATTGGAAAACGTTCTTCGGGGCGAAAACT
CTCAAGGATCTTACCGCTGTTGAGATCCAGTTCGATGTAACCCACTCGTGCACCCAACTG
ATCTTCAGCATCTTTTACTTTCACCAGCGTTTCTGGGTGAGCAAAAACAGGAAGGCAAAA
TGCCGCAAAAAAGGGAATAAGGGCGACACGGAAATGTTGAATACTCATACTCTTCCTTTT
TCAATATTATTGAAGCATTTATCAGGGTTATTGTCTCATGAGCGGATACATATTTGAATG
TATTTAGAAAAATAAACAAATAGGGGTTCCGCGCACATTTC
```

FIG._11A-3

1-845 CMVpromoter/R/U5 5' LTR
1322 GAG ATG-ATC mutation
850-2100 extended ψ r gion
2151-2865 GFP coding region
2866-2894 GGGSGGG linker
2895-2952 FMDV 2a cleavage sequence
2953-3004 Bstx1/Bstx1/HinD3/Hpa1/Sal1/Not1 polylinker
3052-3645 3' LTR
3652-5715 pGEM backbone (pUC origin, ampR)

ATCACGAGGCCCTTTCGTCTTCAAGAACAGCTTTGCTCTTAGGAGTTTCCTAATACATC
CCAAACTCAAATATATAAAGCATTTGACTTGTTCTATGCCCTAGTTATTAATAGTAATC
AATTACGGGGTCATTAGTTCATAGCCCATATATGGAGTTCCGCGTTACATAACTTACGG
TAAATGGCCCGCCTGGCTGACCGCCCAACGACCCCCGCCCATTGACGTCAATAATGACG
TATGTTCCCATAGTAACGCCAATAGGGACTTTCCATTGACGTCAATGGGTGGAGTATTT
ACGGTAAACTGCCCACTTGGCAGTACATCAAGTGTATCATATGCCAAGTACGCCCCCTA
TTGACGTCAATGACGGTAAATGGCCCGCCTGGCATTATGCCCAGTACATGACCTTATGG
GACTTTCCTACTTGGCAGTACATCTACGTATTAGTCATCGCTATTACCATGGTGATGCG
GTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCA
AAATGTCGTAACAACTCCGCCCCATTGACGCAAATGGGCGGTAGGCATGTACGGTGGGA
GGTCTATATAAGCAGAGCTCAATAAAAGAGCCCACAACCCCTCACTCGGGGCGCCAGTC
CTCCGATTGACTGAGTCGCCCGGGTACCCGTGTATCCAATAAACCCTCTTGCAGTTGCA
TCCGACTTGTGGTCTCGCTGTTCCTTGGGAGGGTCTCCTCTGAGTGATTGACTACCCGT
CAGCGGGGGTCTTTCATTTGGGGGCTCGTCCGGGATCGGGAGACCCCTGCCCAGGGACC
ACCGACCCACCACCGGGAGGTAAGCTGGCCAGCAACTTATCTGTGTCTGTCCGATTGTC
TAGTGTCTATGACTGATTTTATGCGCCTGCGTCGGTACTAGTTAGCTAACTAGCTCTGT
ATCTGGCGGACCCGTGGTGGAACTGACGAGTTCGGAACACCCGGCCGCAACCCTGGGAG
ACGTCCCAGGGACTTCGGGGGCCGTTTTTGTGGCCCGACCTGAGTCCAAAAATCCCGAT
CGTTTTGGACTCTTTGGTGCACCCCCCTTAGAGGAGGGATATGTGGTTCTGGTAGGAGA
CGAGAACCTAAAACAGTTCCCGCCTCCGTCTGAATTTTTGCTTTCGGTTTGGGACCGAA
GCCGCGCCGCGCGTCTTGTCTGCTGCAGCATCGTTCTGTGTTGTCTCTGTCTGACTGTG
TTTCTGTATTTGTCTGAAAATATCGGCCCGGGCCAGACTGTTACCACTCCCTTAAGTTT
GACCTTAGGTCACTGGAAAGATGTCGAGCGGATCGCTCACAACCAGTCGGTAGATGTCA
AGAAGAGACGTTGGGTTACCTTCTGCTCTGCAGAATGGCCAACCTTTAACGTCGGATGG
CCGCGAGACGGCACCTTTAACCGAGACCTCATCACCCAGGTTAAGATCAAGGTCTTTTC
ACCTGGCCCGCATGGACACCCAGACCAGGTCCCCTACATCGTGACCTGGGAAGCCTTGG
CTTTTGACCCCCCTCCCTGGGTCAAGCCCTTTGTACACCCTAAGCCTCCGCCTCCTCTT
CCTCCATCCGCCCCGTCTCTCCCCCTTGAACCTCCTCGTTCGACCCCGCCTCGATCCTC
CCTTTATCCAGCCCTCACTCCTTCTCTAGGCGCCCCCATATGGCCATATGAGATCTTAT
ATGGGGCACCCCCGCCCCTTGTAAACTTCCCTGACCCTGACATGACAAGAGTTACTAAC
AGCCCCTCTCTCCAAGCTCACTTACAGGCTCTCTACTTAGTCCAGCACGAAGTCTGGAG
ACCTCTGGCGGCAGCCTACCAAGAACAACTGGACCGACCGGTGGTACCTCACCCTTACC
GAGTCGGCGACACAGTGTGGGTCCGCCGACACCAGACTAAGAACCTAGAACCTCGCTGG
AAAGGACCTTACACAGTCCTGCTGACCACCCCCACCGCCCTCAAAGTAGACGGCATCGC
AGCTTGGATACACGCCGCCCACGTGAAGGCTGCCGACCCCGGGGGTGGACCATCCTCTA
GACTGCCGGATCTCGAGGGATCCACCATGGTGAGCAAGGGCGAGGAGCTGTTCACCGGG

FIG._11B-1

```
GTGGTGCCCATCCTGGTCGAGCTGGACGGCGACGTAAACGGCCACAAGTTCAGCGTGTC
CGGCGAGGGCGAGGGCGATGCCACCTACGGCAAGCTGACCCTGAAGTTCATCTGCACCA
CCGGCAAGCTGCCCGTGCCCTGGCCCACCCTCGTGACCACCCTGACCTACGGCGTGCAG
TGCTTCAGCCGCTACCCCGACCACATGAAGCAGCACGACTTCTTCAAGTCCGCCATGCC
CGAAGGCTACGTCCAGGAGCGCACCATCTTCTTCAAGGACGACGGCAACTACAAGACCC
GCGCCGAGGTGAAGTTCGAGGGCGACACCCTGGTGAACCGCATCGAGCTGAAGGGCATC
GACTTCAAGGAGGACGGCAACATCCTGGGGCACAAGCTGGAGTACAACTACAACAGCCA
CAACGTCTATATCATGGCCGACAAGCAGAAGAACGGCATCAAGGTGAACTTCAAGATCC
GCCACAACATCGAGGACGGCAGCGTGCAGCTCGCCGACCACTACCAGCAGAACACCCCC
ATCGGCGACGGCCCCGTGCTGCTGCCCGACAACCACTACCTGAGCACCCAGTCCGCCCT
GAGCAAAGACCCCAACGAGAAGCGCGATCACATGGTCCTGCTGGAGTTCGTGACCGCCG
CCGGGATCACTCTCGGCATGGACGAGCTGTACAAGGAATTCGGAGGTGGCAGCGGTGGC
GGTCAGCTGTTGAATTTTGACCTTCTTAAACTTGCGGGAGACGTCGAGTCCAACCCTGG
GCCCACCACCACCATGGAAGCTTCCATTAAATTGGTTAACGTCGACGCGGCCGCTCGAC
GATAAAATAAAAGATTTTATTTAGTCTCCAGAAAAAGGGGGGAATGAAAGACCCCACCT
GTAGGTTTGGCAAGCTAGCTTAAGTAACGCCATTTTGCAAGGCATGGAAAAATACATAA
CTGAGAATAGAGAAGTTCAGATCAAGGTCAGGAACAGATGGAACAGCTGAATATGGGCC
AAACAGGATATCTGTGGTAAGCAGTTCCTGCCCCGGCTCAGGGCCAAGAACAGATGGAA
CAGCTGAATATGGGCCAAACAGGATATCTGTGGTAAGCAGTTCCTGCCCCGGCTCAGGG
CCAAGAACAGATGGTCCCCAGATGCGGTCCAGCCCTCAGCAGTTTCTAGAGAACCATCA
GATGTTTCCAGGGTGCCCCAAGGACCTGAAATGACCCTGTGCCTTATTTGAACTAACCA
ATCAGTTCGCTTCTCGCTTCTGTTCGCGCGCTTCTGCTCCCCGAGCTCAATAAAAGAGC
CCACAACCCCTCACTCGGGGCGCCAGTCCTCCGATTGACTGAGTCGCCCGGGTACCCGT
GTATCCAATAAACCCTCTTGCAGTTGCATCCGACTTGTGGTCTCGCTGTTCCTTGGGAG
GGTCTCCTCTGAGTGATTGACTACCCGTCAGCGGGGGTCTTTCATTTCCGACTTGTGGT
CTCGCTGCCTTGGGAGGGTCTCCTCTGAGTGATTGACTACCCGTCAGCGGGGGTCTTCA
CATGCAGCATGTATCAAAATTAATTTGGTTTTTTTTCTTAAGTATTTACATTAAATGGC
CATAGTTGCATTAATGAATCGGCCAACGCGCGGGGAGAGGCGGTTTGCGTATTGGCGCT
CTTCCGCTTCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAACGCAGGAAA
GAACATGTGAGCAAAAGGCCAGCAAAGGCCAGGAACCGTAAAAAGGCCGCGTTGCTGG
CGTTTTTCCATAGGCTCCGCCCCCTGACGAGCATCACAAAAATCGACGCTCAAGTCAG
AGGTGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGGTC
GTTCGCTCCAAGCTGGGCTGTGTGCACGAACCCCCCGTTCAGCCCGACCGCTGCGCCTT
ATCCGGTAACTATCGTCTTGAGTCCAACCCGGTAAGACACGACTTATCGCCACTGGCAG
CAGCCACTGGTAACAGGATTAGCAGAGCGAGGTATGTAGGCGGTGCTACAGAGTTCTTG
AAGTGGTGGCCTAACTACGGCTACACTAGAAGGACAGTATTTGGTATCTGCGCTCTGCT
GAAGCCAGTTACCTTCGGAAAAGAGTTGGTAGCTCTTGATCCGGCAAACAAACCACCG
CTGGTAGCGGTGGTTTTTTTGTTTGCAAGCAGCAGATTACGCGCAGAAAAAAGGATCT
CAAGAAGATCCTTTGATCTTTTCTACGGGGTCTGACGCTCAGTGGAACGAAAACTCACG
TTAAGGGATTTTGGTCATGAGATTATCAAAAGGATCTTCACCTAGATCCTTTTAAATT
AAAATGAAGTTTGCGCAAATCAATCTAAAGTATATATGAGTAAACTTGGTCTGACAGT
TACCAATGCTTAATCAGTGAGGCACCTATCTCAGCGATCTGTCTATTTCGTTCATCCAT
AGTTGCCTGACTCCCCGTCGTGTAGATAACTACGATACGGGAGGGCTTACCATCTGGCC
CCAGTGCTGCAATGATACCGCGAGACCCACGCTCACCGGCTCCAGATTTATCAGCAATA
```

FIG._11B-2

```
AACCAGCCAGCCGGAAGGGCCGAGCGCAGAAGTGGTCCTGCAACTTTATCCGCCTCCAT
CCAGTCTATTAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTTGGTATGGCT
TCATTCAGCTCCGGTTCCCAACGATCAAGGCGAGTTACATGATCCCCCATGTTGTGCAA
AAAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCG
ACCGAGTTGCTCTTGCCCGGCGTCAACACGGGATAATACCGCGCCACATAGCAGAACTT
TAAAAGTGCTCATCATTGGAAAACGTTCTTCGGGGCGAAAACTCTCAAGGATCTTACCG
CTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAGG
GAATAAGGGCGACACGGAAATGTTGAATACTCATACTCTTCCTTTTTCAATATTATTGA
AGCATTTATCAGGGTTATTGTCTCATGACATTAACCTATAAAAATAGGCGT
```

FIG._11B-3

1-845    CMVpormoter/R/U5 5' LTR
1322     GAG ATG-ATC mutation
850-2100 extended ψ region
2146-2173 two Bstx1 peptide cloning sites
2173-2214 EoR1/Apa1/Hpa1/Not1 polylinker
2262-2855 3' LTR
2855-4901 pGEM backbone (pUC origin, ampR)

```
ATCACGAGGCCCTTTCGTCTTCAAGAACAGCTTTGCTCTTAGGAGTTTCCTAATACATC
CCAAACTCAAATATATAAAGCATTTGACTTGTTCTATGCCCTAGTTATTAATAGTAATC
AATTACGGGGTCATTAGTTCATAGCCATATATGGAGTTCCGCGTTACATAACTTACGGT
AAATGGCCCGCCTGGCTGACCGCCCAACGACCCCCGCCCATTGACGTCAATAATGACGT
ATGTTCCCATAGTAACGCCAATAGGGACTTTCCATTGACGTCAATGGGTGGAGTATTTA
CGGTAAACTGCCCACTTGGCAGTACATCAAGTGTATCATATGCCAAGTACGCCCCCTAT
TGACGTCAATGACGGTAAATGGCCCGCCTGGCATTATGCCCAGTACATGACCTTATGGG
ACTTTCCTACTTGGCAGTACATCTACGTATTAGTCATCGCTATTACCATGGTGATGCGG
TTTTGGCAGTACATCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAA
AATGTCGTAACAACTCCGCCCCATTGACGCAAATGGGCGGTAGGCATGTACGGTGGGAG
GTCTATATAAGCAGAGCTCAATAAAAGAGCCCACAACCCCTCACTCGGGGCGCCAGTCC
TCCGATTGACTGAGTCGCCCGGGTACCCGTGTATCCAATAAACCCTCTTGCAGTTGCAT
CCGACTTGTGGTCTCGCTGTTCCTTGGGAGGGTCTCCTCTGAGTGATTGACTACCCGTC
AGCGGGGGTCTTTCATTTGGGGGCTCGTCCGGGATCGGGAGACCCCTGCCCAGGGACCA
CCGACCCACCACCGGGAGGTAAGCTGGCCAGCAACTTATCTGTGTCTGTCCGATTGTCT
AGTGTCTATGACTGATTTTATGCGCCTGCGTCGGTACTAGTTAGCTAACTAGCTCTGTA
TCTGGCGGACCCGTGGTGGAACTGACGAGTTCGGAACACCCGGCCGCAACCCTGGGAGA
CGTCCCAGGGACTTCGGGGCCGTTTTGTGGCCCGACCTGAGTCCAAAAATCCCGATC
GTTTTGGACTCTTTGGTGCACCCCCCTTAGAGGAGGGATATGTGGTTCTGGTAGGAGAC
GAGAACCTAAAACAGTTCCCGCCTCCGTCTGAATTTTTGCTTTCGGTTTGGGACCGAAG
CCGCGCCGCGCGTCTTGTCTGCTGCAGCATCGTTCTGTGTTGTCTCTGTCTGACTGTGT
TTCTGTATTTGTCTGAAAATATCGGCCCGGGCCAGACTGTTACCACTCCCTTAAGTTTG
ACCTTAGGTCACTGGAAAGATGTCGAGCGGATCGCTCACAACCAGTCGGTAGATGTCAA
GAAGAGACGTTGGGTTACCTTCTGCTCTGCAGAATGGCCAACCTTTAACGTCGGATGGC
CGCGAGACGGCACCTTTAACCGAGACCTCATCACCCAGGTTAAGATCAAGGTCTTTTCA
CCTGGCCCGCATGGACACCCAGACCAGGTCCCCTACATCGTGACCTGGGAAGCCTTGGC
TTTTGACCCCCCTCCCTGGGTCAAGCCCTTTGTACACCCTAAGCCTCCGCCTCCTCTTC
CTCCATCCGCCCCGTCTCTCCCCCTTGAACCTCCTCGTTCGACCCCGCCTCGATCCTCC
CTTTATCCAGCCCTCACTCCTTCTCTAGGCGCCCCCATATGGCCATATGAGATCTTATA
TGGGGCACCCCCGCCCCTTGTAAACTTCCCTGACCCTGACATGACAAGAGTTACTAACA
GCCCCTCTCTCCAAGCTCACTTACAGGCTCTCTACTTAGTCCAGCACGAAGTCTGGAGA
CCTCTGGCGGCAGCCTACCAAGAACAACTGGACCGACCGGTGGTACCTCACCCTTACCG
AGTCGGCGACACAGTGTGGGTCCGCCGACACCAGACTAAGAACCTAGAACCTCGCTGGA
AAGGACCTTACACAGTCCTGCTGACCACCCCACCGCCCTCAAAGTAGACGGCATCGCA
GCTTGGATACACGCCGCCCACGTGAAGGCTGCCGACCCCGGGGGTGGACCATCCTCTAG
ACTGCCGGATCTCGAGGGATCCACCACCATGGACCCCCATTAAATTGGAATTCGGGGCC
CAAGCTTTGTTAACGTCGACGCGGCCGCCGTCGACGATAAAATAAAAGATTTTATTTAG
TCTCCAGAAAAAGGGGGGAATGAAAGACCCCACCTGTAGGTTTGGCAAGCTAGCTTAAG
TAACGCCATTTTGCAAGGCATGGAAAAATACATAACTGAGAATAGAGAAGTTCAGATCA
```

FIG._11C-1

```
AGGTCAGGAACAGATGGAACAGCTGAATATGGGCCAAACAGGATATCTGTGGTAAGCAG
TTCCTGCCCCGGCTCAGGGCCAAGAACAGATGGAACAGCTGAATATGGGCCAAACAGGA
TATCTGTGGTAAGCAGTTCCTGCCCCGGCTCAGGGCCAAGAACAGATGGTCCCCAGATG
CGGTCCAGCCCTCAGCAGTTTCTAGAGAACCATCAGATGTTTCCAGGGTGCCCCAAGGA
CCTGAAATGACCCTGTGCCTTATTTGAACTAACCAATCAGTTCGCTTCTCGCTTCTGTT
CGCGCGCTTCTGCTCCCCGAGCTCAATAAAAGAGCCCACAACCCCTCACTCGGGGCGCC
AGTCCTCCGATTGACTGAGTCGCCCGGGTACCCGTGTATCCAATAAACCCTCTTGCAGT
TGCATCCGACTTGTGGTCTCGCTGTTCCTTGGGAGGGTCTCCTCTGAGTGATTGACTAC
CCGTCAGCGGGGGTCTTTCATTTCCGACTTGTGGTCTCGCTGCCTTGGGAGGGTCTCCT
CTGAGTGATTGACTACCCGTCAGCGGGGTCTTCACATGCAGCATGTATCAAAATTAAT
TTGGTTTTTTTTCTTAAGTATTTACATTAAATGGCCATAGTTGCATTAATGAATCGGCC
AACGCGCGGGGAGAGGCGGTTTGCGTATTGGCGCTCTTCCGCTTCCTCGCTCACTGACT
CGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCT
GCCGCTTACCGGATACCTGTCCGCCTTTCTCCCTTCGGGAAGCGTGGCGCTTTCTCATA
GCTCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAGTC
CAACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTAC
ACTAGAAGGACAGTATTTGGTATCTGCGCTCTGCTGAAGCCAGTTACCTTCGGAAAAAG
AGTTGGTAGCTCTTGATCCGGCAAACAAACCACCGCTGGTAGCGGTGGTTTTTTTGTTT
GCAAGCAGCAGATTACGCGCAGAAAAAAGGATCTCAAGAAGATCCTTTGATCTTTTCT
ACGGGGTCTGACGCTCAGTGGAACGAAAACTCACGTTAAGGGATTTTGGTCATGAGATT
ATCAAAAGGATCTTCACCTAGATCCTTTTAAATTAAAAATGAAGTTTGCGCAAATCAA
TCTAAAGTATATATGAGTAAACTTGGTCTGACAGTTACCAATGCTTAATCAGTGAGGCA
CCTATCTCAGCGATCTGTCTATTTCGTTCATCCATAGTTGCCTGACTCCCCGTCGTGTA
GATAACTACGATACGGGAGGGCTTACCATCTGGCCCCAGTGCTGCAATGATACCGCGAG
ACCCACGCTCACCGGCTCCAGATTTATCAGCAATAAACCAGCCAGCCGGAAGGGCCGAG
CGCAGAAGTGGTCCTGCAACTTTATCCGCCTCCATCCAGTCTATTAATTGTTGCCGGGA
AGCTAGAGTAAGTAGTTCGCCAGTTAATAGTTTGCGCAACGTTGTTGCCATTGCTACAG
GCATCGTGGTGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTCCTTCGGTCC
TCCGATCGTTGTCAGAAGTAAGTTGGCCGCAGTGTTATCACTCATGGTTATGGCAGCAC
TGCATAATTCTCTTACTGTCATGCCATCCGTAAGATGCTTTTCTGTGACTGGTGAGTAC
TCAACCAAGTCATTCTGAGAATAGTGTATGCGGCGACCGAGTTGCTCTTGCCCGGCGTC
AACACGGGATAATACCGCGCCACATAGCAGAACTTTAAAAGTGCTCATCATTGGAAAAC
GTTCTTCGGGGCGAAAACTCTCAAGGATCTTACCGCTGTTGAGATCCAGTTCGATGTAA
CCCACTCGTGCACCCAACTGATCTTCAGCATCTTTTACTTTCACCAGCGTTTCTGGGTG
AGCAAAAACAGGAAGGCAAAATGCCGCAAAAAAGGGAATAAGGGCGACACGGAAATGTT
GAATACTCATACTCTTCCTTTTTCAATATTATTGAAGCATTTATCAGGGTTATTGTCTC
ATGACATTAACCTATAAAAATAGGCGT
```

FIG._11C-2

(1) C12ScFas Survival construct

C12ScFas: epsilon-cFas(CD95)-Ires-Hygro-BGH PolyA put into C12s vector backwards
so that no leaky transcription happens through the cmv promoter.

atcacgaggccctttcgtcttcaagaacagcttgtctcttaggagtttcctaatacatcccaaactcaaatataaagc
atttgactgtctctatgccctagttattaatcaattacgggtcattagttcatagcccatatatggagttccg
cgttacataacttacggtaaatgccccgcctgactttccattgacgtcaatagtaatgacgtatg
ttcccatagtaacgccaataggactttccattgacgtcaatgggtggagtatttacggtaaactgcccacttggcagta
catcaagtgtatcatatgccaagtacgccccctattgacgtcaatgacggtaaatggcccgcctggcattatgcccagta
catgaccttatgggactttcctacttggcagtacatctacgtattagtcatcgctattaccatggtgatgcggttttggc
agtacatcaatgggcgtggatagcggtttgactcacggggatttccaagtctccaccccattgacgtcaatgggagtttg
tttggcaccaaaatcaacgggactttccaaaatgtcgtaacaactccgccccattgacgcaaatgggcggtaggcgtgt
acgggtgagtccgcccccctattgacgcaaatgggcggtaggcgtgtacggtgggaggtctatataagcagagctcgttt
gagtcgctctgagtgattgactaccgtgactataacctcttgcagttgcatccgatccgagacccctgccag
tctcctctgagtgattgactaccgtgactataacctcttgcagttgcatccgatccgagacccctgccag
ggaccaccgaccacccaggaggtaagctgcccagaactctgtgtctgtctgcggaccccgattgtctagtgtctgactga
tttatgcgcctgcctgcgtcgtactagtctgcccagggactttcggggagacgttgtgcccgaccctttgtgtgcccgaccctagtgaactgacgagttcggaa
cacccggccgccgcaacctctttggtgcacccccttgagaggaggacttcggtaggagagaagaacctaaacagttcc
tcgttttggactcttttgccgtcctgaattttttgcttttcgggtccgtgcgcgaagcgcgaaagatatatggcgggaccgaagccttgtctgctgcagcatcgtctgt
cgcctcgtctgaatttttgcttttcgggtccgtgcgcgaagcgcgaaagatatgggcggaccgaagccttgtctgctgcagcatcgtctgt
tgtctctgtctgactgtgttttctgtatttgtctgaaaaatatgggcccagatcgttaccactccctaagtttgac
cttagtcactggaaagatgccagcggatcgctcgagcgattgcctgccccagccgtcggtagatgtcaagagacgttggtttaccttct
gctctgcagaatggccaacctcttttaacgctgccgagacgagccccaccttaaccgagaccttaacatcgtgctctctactcaccaggttaag
atcaaggtcttttccctgggtcaaagcccgcctttgtacacctttatccagcctcccttatctcactccttctctaggcgccccatatggccatat
cccccccccgttgacccccgccagctcgatccctgtaaactttccctgacatgacaagagttactaaccaactgg
aacctctgttgaccccgccagctcgatccctgtaaactttccctgacatgacaagagttactaaccaactgg
gagatcttatatgggcaccccgctcttcaccctactcagtccagcacgaagtctggagacctgggtccgccgacactggaacctcct
ccaagtcacttacaggtcctccacccgagtcggcgacacacagtgtgggtccgccgacacagtggcagtggcagcttggatacacgc
accgaccggtggtacctcaccctacacagtgccgaaaggaccttctgctgaccaccccagctcgacgacgaccccaaagtagacggcagcttggatacacgc
cgctggaaaggaccttctgctgaccaccccagctcgacgacgaccccaaagtagacggcagcttggatacacgc
cgccacgtgaaggctgccgaccccgggggtgaccatcctctagactgccGGATCTCGAGGGATCCTCCCCAGCATGCC TGCTATTGTCTTCCCAATCCTCCCCCCTTGCTGTCCTGCCCACCCCCAGAATAGAATGACACCTACTCAGACAA
TGCGATGCAATTTCCTCATTTTATTAGGAAAGACAGTGGGAGTGGCACCTTCCAGGGTCAAGGAAGGCACGGGGGAGGG
GCAAACAACAGATGCTGGCAACTAGAAGGCACAGTCGAGTCCTAGCTTGCCAAACCTACAGGTGGGGTCTTTCATTCCC

```
CCAGAGGCAGGACAGCCCAGATCCACACCATgGTGGCTTTACCAACAGTACCGGAATGCCAAGCTTGCGGCCGCTTAAGA
GCTGTAATTGAACCTGGGAGTGGACACCTGTGGAGAGAAAGGCAAAGTGGATGTCAGTAAGACCAATAGGTGCCTATCAG
AAACGCAAGAGTCTTCTCTGTCTCGACAAGCCCAGTTTCTATTGGTCTCCTTAAACCTGTCTTGTAACCTTGATACTTAC
CTGCCCAGTGCCTCACGACCAACTTctgcaggaattcctggacagctcccagatgatcagtaacgtggttgttattct
gtgccgggcagtggagcctgggtagggggagctctgctcagtgcttcagctaaaaatgggtgggaacccCcaggagg
cccgggccgccgtcccttctctctgttctcttgggaagtcgattgagcaacagcgggggtcaggtgaggctcc
ttcactaccgatgcacaccgagtgctGgggagggttctctctctcaggcccaacCccaggcccctgcctaggtccc
ggactctCactcCttgacgacgcatcCttgctCccacgaaagcctTgggtcccgttccctgcctgggaagggagag
ggtactgggcatcgacagtgtgcttccacgaaagcctTgtgaagaaaggatggggcgctttgtgcaggagaatgagg
cgcactgaggtgaactggcccctcggggGcgcgtgtcccagatgtgtgcagggcctcctgatggccgcagccctgtcc
ctgtgacccgcttgagcttggcaccctgagtgctggcctcacCTTGTACTCACTCCCAGGTCACTGTCCtcgacGCGGCC
GCTCGAcgatAAAATAAAAGATTTTATTAGTCTCCAGAAAAAGGGGGAATGAAAGACCCCACCTGTAGGTTTGGCAAg
ctagcTTAAGTAACCCATTTTGCAAGGCATGGAAAAATACATAACTGAGAATAGAGAAGTTCAGATCAAGGTCGAACAG
ATGGAACAGGCAATAAAGAGCCCACAACCCCTCACTCGGGGCGCGCAGTCCTCCGATTGACTGAGTCGCCCGGGTACCCG
TGTATCCAATAAACCCTCTTGCAGTTGCATCCGACTTGTGTGCTCTCGCGTTCCTTGGAGGGTCTCCCTCGAGTGATTGA
CTACCCGTCAGCGGGGGTCTTTCAcatgcaGCATGTATCAAAATTAATTTGGTTTTTTTTCTTAAGTATTTACATTAAAT
GGCCATAgtttcGTAATCATGGTCATAGCCTGTTTCCTGTGTGAAATTGTTATCCGCTCACAATTCCACACAACATACGAG
CCGGAAGCATAAGTGTAAAGCCTGGGGTGCCTAATGAGTGAGCTAACTCACATTAATTGCGTTGCGCTCACTGCCCGCT
TTCCAGTCGGGAAACCTGTCGTGCCAGCTGCATTAATGAATCGGCCAACGCGCGGGGAGAGGCGGTTTGCGTATTGGGCG
CTCTTCCGCTTCCTCGCTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGAGCATCACAAAAATCGACGCTCAAGTCAGAG
GTGGCGAAACCCGACAGGACTATAAAGATACCAGGCGTTTCCCCCTGGAAGCTCCCTCGTGCGCTCTCCTGTTCCGACCC
```

FIG._12D

```
TGCCGCTTACCGGATACCTGTCCGGCCCTTTCTCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCCCGTTCAGCCCGACCGCTGCGCCTTATCCGG
TAACTATCGTCTTGAGTCCAACCCGGTAAGACACGACTTATCGCCACTGGCAGCAGCCACTGGTAACAGGATTAGCAGAG
CGAGGTATGTAGGCGGTGCTACAGAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGCAAACAAACCACCGCTGGTAGCGG
TGGTTTTTTGTTGCAAGCAGCAGATTACGCGCAGAAAAAAGGATCTCAAGAAGATCCTTTGATCTTTTCTACGGGGT
CTGACGCTCAGTGGAACGAAAACTCACGTTAAGGGATTTTGGTCATGAGATTATCAAAAAGGATCTTCACCTAGATCCTT
TTAAATTAAAAATGAAGTTTGCGCAAATCAATCTAAAGTATATATATGAGTAAACTTGGTCTGACAGTTACCAATGCTTAAT
CAGTGAGGCACCTATCTCAGCGATCTGTCTATTTCGTTCATCCATAGTTGCCTGACTCCCCGTCGTAGATAACTACGA
TACGGGAGGGCTTACCATCTGGCCCCAGTGCTGCAATGATACCGCGAGACCACGCTCACCGGCTCCAGATTTATCAGCA
ATAAACCAGCCAGCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTGCTACAGGCATCGTGGTGTCAC
GCTCGTCGTTTGGTATGGCTTCATTCAGCTCCGGTTCCCAACGATCAAGGCGAGTTACATGATCCCCCATGTTGTGCAAA
AAAGCGGTTAGCTCCTTCGGTCCTCCGATCGTTGTCAGAAGTAAGTTGGCCGCAGTGTTATCACTCATGGTTATGGCAGC
ACTGCATAATTCTCTTACTGTCATGCCATCCGTAAGATGCTTTTCTGTGACTGGTGagtactcaaccagtcattctgag
aatagtgtatgcggcgaccgagttgctcttgcccggcgtcaacacgggataataccgcgccacatagcagaactttaaaa
gtgctcatcattggaaaacgttcttcggggcgaaaactctcaaggatcttaccgctgttgagatccagttcgatgtaacc
cactcgtgcacccaactgatcttcagcatcttttactttcaccagcgtttctgggtgagcaaaaacaggaaggcaaaatg
ccgcaaaaaagggaataagggcgacacggaaatgttgaatactcatactcttcctttttcaatattattgaagcattat
cagggttattgtctcatgagcggatacatatttgaatgtatttagaaaaataaacaaataggcgt
```

(2) Ahhhh: Survival construct

2.) Ahhhh: epsilon-cFas' (CD8 or mLyt2)-Ires-Hygro-BGHpolyA also in C12s backwards

```
atcacgaggccctttcgtcttcaagaacagctttgctctttaggagtttcctaatacatccaaactcaaatatataaagc
atttgacttgttctatgccctagttattaatagtaatcaattacgggtcattagttcatagcccatatatggagttccg
cgttacataacttacggtaaatggccgcctggctgacgtcaataatgacgtattagttcatagcccatatatggagttccg
ttcccatagtaacgccaataggactttccattgacgtcaatgggtggagtatttacggtaaactgcccacttggcagta
catcaagtgtatcatatgccaagtacgccccctattgacgtcaatgacggtaaatggcccgcctggcattatgccagta
catgaccttatgggactttcctacttggcagtacatctacgtattagtcatcgctattaccatggtgatgcggttttgg
agtacatcaatgggcgtggatagcggtttgactcacggggatttccaagtctccaccccattgacgtcaatgggagtttg
tttggcaccaaaatcaacgggactttccaaaatgtcgtaacaactccgccccattgacgcaaatgggcggtaggcatgt
acggtgggaggtctatataagcagagctcgtttagtgaaccgtcagatcgcctggagacgccatccacgctgttttgac
gagtcgccgggtacccgtgattgactaccggtaagctggctaactagtagtctctgtatctgtcgaccttagctcatgaa
tctctctgagtgattgactaccacggagctaagctggctaactagtagtctctgtatctgtcggaatctgtaggagtcggaa
ggaccacgaccaccgctcgtcggtactagttagtactgaaacgtccaggacttcgggggcgttttttgtggccgacctgagtt
tttatgcgccgctgcgcaacctggagagccagggatctcggggcttcggggatatgtggttctgtggttctgcagcatcgttctgt
cacccggccgcaactctttggtgcacccccttagagaggaggatatgtggttctgtgcgcgaagccgaagccgaaaaataaacagttcc
tcgttttggactctttggtgcacccccttagagaggaggatatgtggttctgtgcgcgaagccgaagccgaaaaataaacagttcc
cgcctccgtctgaattttttgctctgtcttctgtattttgtctgaaaatatgggcccagacgtcttgttaccactccctttaagtttgac
tgtctctgtctgactgtgtcttctgtattttgtctgaaaatatgggcccagacgtcttgttaccactccctttaagtttgac
cttaggtcactgaaagatgtcgagcggatcgctcacaaccagtcggtagatgtcaagaagagacctcatcaccaggttaag
gctctgcagaatggccaacctggcccgcatggggacacaccagtccccctctcagcccctgaccgtgactcggcttttga
atcaaggtctttcacctggcccgcatggggacacaccagtccccctctcagcccctgaccgtgactcggcttttga
ccccccctctcccggggtcaagccccctgctctacttgtaaacttccctgtaaacttccctgacatgacaggttactaacagccctctct
aacctcctgtcgaccccgcctcgatcccgcctttgtaaacttccctgtaaacttccctgacatgacaggttactaacagccctctct
gagatcttatatgggcacaggctgtctcaccctcacacagtcctgctgaccccaaagtagacggcatcgcagcttgatacacgc
ccaagctcactacaggctgtctcaccctctacacagtcctgctgaccccaaagtagacggcatcgcagcttgatacacgc
acgaccggtgaaggaccttacacagtcctgctgaccccaaagtagacggcatcgcagcttgatacacgc
cgctgaaaggaccttacacagtcctgctgaccccaaagtagacggcatcgcagcttgatacacgc
cgcccacgtgaaggctgccgaccccgggggtggaccatcctctagactgccGGATCTCGAGGGATCCTCCCCAGCATGCC TGCTATTGTCTTCCCAATCCTCCCCCTGCTCCTGTCCTGCCCACCCCAGAATAGAATGACACCTACTCAGACAA
TGCGATGCAATTTCCTCATTTATTAGGAAAGGACAGTGGGAGTGGCACCTTCCAGGGTCAAGGAAGGCACGGGGAGGG
GCAAACAACAGATGCTGGCAACTAGAAGGCACAGTCGAGGTCTAGCCTTGCCAAACCTACAGGTGGGGTCTTTCATTCCC
```

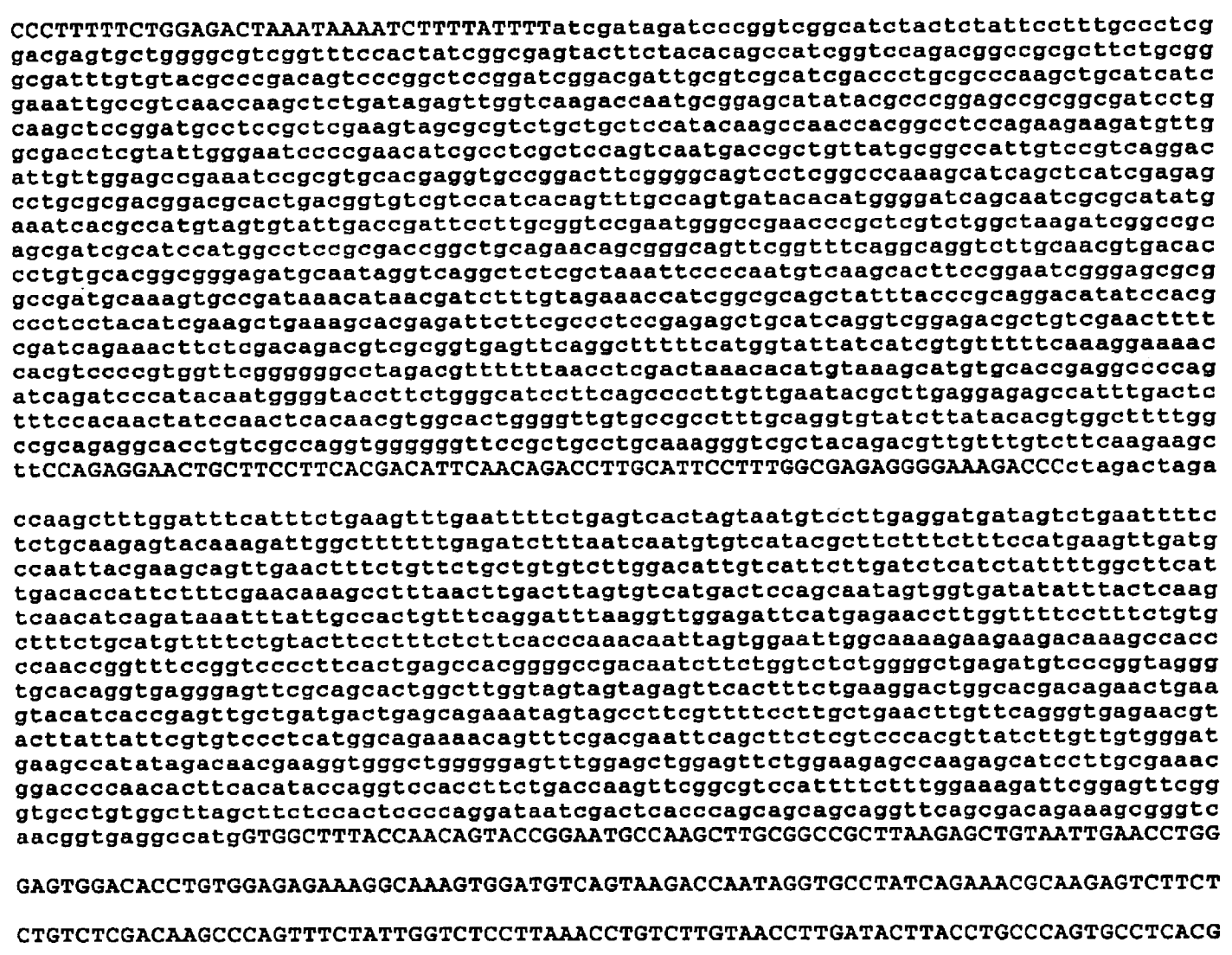

ACCAACTTctgcaggaattcctggacagctcccagatgatcagtaaccgtggttgttattctgtgccgggcagtggagc
ctgggtaggggagctctgcctcagtgctcttcagtaaaaatggggtgggaaccccCaggagcccggccgccctggaa
gttccctttctctctgttcttgggaagtcgattgagcaacagcggggggtcagtgaggctcctcactaccgatgcaca
ccgagtgctGgggagttctctctctccagtcagcaaacttgggtcccgttgctggagaaggagaggtactgggcatcgacg
gcatgcgtggcttggtgtccacgaaagccttgtgaagaaggatggggcgcttctgatggccgcagcctgtccctgtgagc
ccctcggggGcgcgtgtccagatgtgtgcaggcctgtgcaggggcgcctgtccctgtgaccgctggag
ctggcaccctgagtggtggcctcaccCTTGTACTTCCACTCCCAGTGCACTGTCCtcgacGCGGCCGCTCgaCGAtaAAAATAA AAGATTTATTTAGTCTCCAGAAAAGACCCCACCTGTAGGTTTGGCAAgctagcTTAAGTAACCCA

TTTTGCAAGGCATGAAAAATACATAACTGAGAAATAGAGAAGTTCAGATCAAGGTCGGAACAGATGGAACAGGCAATAAA

AGAGCCCACAACCCCTCACTCGGGCGCCAGTCCTCCGATTGACTGAGTCGCCCCGGTACCCGTGTATCCAATAAACCCT

CTTGCAGTTGCATCCGACTGTGGTCTCGCTGTTCCTTGGAGGGTCTCCTCTGAGTGATTGACTACCCGTCAGCGGGGG

TCTTTCAcatgcaGCATGTATCAAAATTAATTTGGTTTTTTTTCTTAAGTATTTACATTAAATGCCATAgtttcGTAAT

CATGGTCATAGCTGTGTTTCCTGTGTGAAATTGTTATCCGCTCACAATTCCACACAACATACGAGCCGAAGCATAAAGTGT

AAAGCCTGGGGTGCCTAATGAGTGAGCTAACTCACATTAATTGCGTTGCGCTCACTGCCCGCTTTCCAGTCGGGAAACCT

GTCGTGCCAGCTGCATTAATGAATCGGCCAACGCGCGGGAGAGGCGGTTTGCGTATTGGGCGCTCTTCCGCTTCCTCGC

TCACTGACTCGCTGCGCTCGGTCGTTCGGCTGCGGCGAGCGGTATCAGCTCACTCAAAGGCGGTAATACGGTTATCCACA

GAATCAGGGGATAACGCAGGAAAGAACATGTGAGCAAAAGGCCAGCAACAAAAGGCCGCGTTGCTGGCGTTTTTCCATAGGCTCCGCCCCCCTGACGAGCATCACAAAAATCGACGCTCAAGTCAGAGGTGGCGAAACCCGACAG

GACTATAAAGATACCAGGCGTTTCCCCCTGGAAGCTCCCTCGTGCGCTCTCCTGTTCCGACCCTGCCGCTTACCGGATAC

CTGTCCGCCTTTCTCCCTTCGGGAAGCGTGGCGCTTTCTCATAGCTCACGCTGTAGGTATCTCAGTTCGGTGTAGGTCGT

TCGCTCCAAGCTGGGCTGTGTGCACGAACCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGAGCGAGGTATGTAGGCGGT

```
GCTACAGAGTTCTTGAAGTGGTGGCCTAACTACGGCTACACTAGAAGGACACAGTATTTGGTATCTCGCGCTCTGCTGAAGCC
AGTTACCTTCGGAAAAAGAGTTGGTAGCTCTTGATCCGGCAAACAAACCACCGCTGGTAGCGGTGGTTTTTTTGTTTGCA
AGCAGCAGATTACGCGCAGAAAAAAGGATCTCAAGAAGATCCTTTGATCTTTTCTACGGGTCTGACGCTCAGTGGAAC
GAAAACTCACGTTAAGGGATTTGGTCATGAGATTATCAAAAAGGATCTTCACCTAGATCCTTTTAAATTAAAAATGAAG
TTTGCGCAAATCAATCTAAAGTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTACGATACGGGAGGGCTTACCA
TCTGGCCCCAGTGCTGCAATGATACCGCGAGACCCACGCTCACCGGCTCCAGATTTATCAGCAATAAACCAGCCAGCCGG
AAGGGCCGAGCGCAGAAGTGGTCCTGCAACTTTATCCGCCTCCAGTCTATTAATTGTTGCCGGGAAGCTAGAGTAA
GTAGTTCGCCAGTTAATAGTTTGCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTGCAAAAAAGCGGTTAGCTCCTT
CGGTCCTCCGATCGTTGTCAGAAGTAAGTTGGCCGCAGTGTTATCACTCATGGTTATGGCAGCACTGCATAATTCTCTTA
CTGTCATGCCATCCGTAAGATGCTTTTCTGTGACTGGTGagtactcaaccaagtcattctgagaatagtgtatgcgggcga
ccgagttgctcttgcccggcgtcaacacgggataataccgcgccacatagcagaactttaaaagtgctcatcattggaaa
acgttcttcggggcgaaaactctcaaggatcttaccgctgttgagatccgagttcgatgtaacccactcgtgcacccaact
gatcttcagcatctttactttcaccagcgtttctgggtgagcaaaaacaggaaggcaaaatgccgcaaaaaagggaata
agggcgacacggaaatgttgaatactcatactcttcctttttcaatattattgaagcatttatcagggtattgtctcat
gacattaacctataaaaataggcgt
```

FIG._13D

SEQUENCE LISTING

<160> NUMBER OF SEQ ID NOS: 19

<210> SEQ ID NO 1
<211> LENGTH: 603
<212> TYPE: DNA
<213> ORGANISM: Homo sapiens

<400> SEQUENCE: 1

```
ctcgaggaca gtgacctggg agtgagtaca aggtgaggcc accactcagg gtgccagctc      60
caagcgggtc acagggacga gggctgcggc catcaggagg ccctgcacac acatctggga     120
cacgcgcccc cgagggccag ttcacctcag tgcgcctcat tctcctgcac aaaagcgccc     180
ccatcctttc ttcacaaggc tttcgtggaa gcagaggcgt cgatgcccag taccctctcc     240
ctttcccagg caacgggacc ccaagtttgc tgactgggac caccaagcca cgcatgcgtc     300
aagagtgaga gtccgggacc taggcagggg ccctggggtt gggcctgaga gagaagagaa     360
cctcccccag cactcggtgt gcatcggtag tgaaggagcc tcacctgacc cccgctgttg     420
ctcaatcgac ttcccaagaa cagagagaaa agggaacttc cagggcggcc cgggcctcct     480
gggggttccc accccatttt tagctgaaag cactgaggca gagctcccc  tacccaggct     540 ccactgcccg gcacagaaat aacaaccacg gttactgatc atctgggagc tgtccaggaa     600
ttc                                                                   603
```

-continued

```
<210> SEQ ID NO 2
<211> LENGTH: 143
<212> TYPE: DNA
<213> ORGANISM: Artificial sequence
<220> FEATURE:
<223> OTHER INFORMATION: synthetic

<400> SEQUENCE: 2
gctgggctaa actgggctag cctgagctgg gctgaactgg gctgctgggc tggactgggt    60
aagctgggct gagctgggtt gggtggaaat gggctgagct gagctaggct aaactgggtt   120
tggctgggct gggctgggct ggg                                           143

<210> SEQ ID NO 3
<211> LENGTH: 76
<212> TYPE: DNA
<213> ORGANISM: Artificial sequence
<220> FEATURE:
<223> OTHER INFORMATION: synthetic

<400> SEQUENCE: 3
ggtttggctg ggctgggctg ggctgggctg ggttcagctg agcgggttgg gttagactgg    60
gtcaaactgg ttcagc                                                    76

<210> SEQ ID NO 4
<211> LENGTH: 6219
<212> TYPE: DNA
<213> ORGANISM: Artificial sequence
<220> FEATURE:
<223> OTHER INFORMATION: synthetic

<400> SEQUENCE: 4
atcacgaggc cctttcgtct tcaagaacag ctttgctctt aggagtttcc taatacatcc    60
caaactcaaa tatataaagc atttgacttg ttctatgccc tagttattaa tagtaatcaa   120
ttacggggtc attagttcat agcccatata tggagttccg cgttacataa cttacggtaa   180
atggcccgcc tggctgaccg cccaacgacc cccgcccatt gacgtcaata atgacgtatg   240
ttcccatagt aacgccaata gggactttcc attgacgtca atgggtggag tatttacggt   300
aaactgccca cttggcagta catcaagtgt atcatatgcc aagtacgccc cctattgacg   360
tcaatgacgg taaatggccc gcctggcatt atgcccagta catgacctta tgggactttc   420
ctacttggca gtacatctac gtattagtca tcgctattac catggtgatg cggttttggc   480
agtacatcaa tgggcgtgga tagcggtttg actcacgggg atttccaagt ctccacccca   540
ttgacgtcaa tgggagtttg ttttggcacc aaaatcaacg ggactttcca aaatgtcgta   600
acaactccgc cccattgacg caaatgggcg gtaggcatgt acgtgggag gtctatataa    660 gcagagctca ataaagagc ccacaacccc tcactcgggg cgccagtcct ccgattgact   720
gagtcgcccg gtacccgtg tatccaataa accctcttgc agttgcatcc gacttgtggt    780
ctcgctgttc cttgggaggg tctcctctga gtgattgact acccgtcagc ggggtcttt    840 catttggggg ctcgtccggg atcgggagac ccctgcccag gaccaccga cccaccaccg    900 ggaggtaagc tggccagcaa cttatctgtg tctgtccgat tgtctagtgt ctatgactga    960
ttttatgcgc ctgcgtcggt actagttagc taactagctc tgtatctggc ggacccgtgg   1020
tggaactgac gagttcggaa cacccggccg caaccctggg agacgtccca gggacttcgg   1080
gggccgtttt tgtggcccga cctgagtcca aaatcccga tcgttttgga ctctttggtg   1140
cacccccctt agaggaggga tatgtggttc tggtaggaga cgagaaccta aaacagttcc   1200
```

```
cgcctccgtc tgaattttg ctttcggttt gggaccgaag ccgcgccgcg cgtcttgtct    1260
gctgcagcat cgttctgtgt tgtctctgtc tgactgtgtt tctgtatttg tctgaaaata    1320
tcggcccggg ccagactgtt accactccct taagtttgac cttaggtcac tggaaagatg    1380
tcgagcggat cgctcacaac cagtcggtag atgtcaagaa gagacgttgg gttaccttct    1440
gctctgcaga atggccaacc tttaacgtcg gatggccgcg agacggcacc tttaaccgag    1500
acctcatcac ccaggttaag atcaaggtct tttcacctgg cccgcatgga cacccagacc    1560
aggtccccta catcgtgacc tgggaagcct tggcttttga cccccctccc tgggtcaagc    1620
cctttgtaca ccctaagcct ccgcctcctc ttcctccatc cgccccgtct ctccccttg    1680
aacctcctcg ttcgaccccg cctcgatcct cccttatcc agccctcact ccttctctag    1740
gcgcccccat atggccatat gagatcttat atggggcacc cccgccccttgtaaacttcc    1800
ctgaccctga catgacaaga gttactaaca gcccctctct ccaagctcac ttacaggctc    1860
tctacttagt ccagcacgaa gtctggagac tctggcggc agcctaccaa gaacaactgg    1920
accgaccggt ggtacctcac ccttaccgag tcggcgacac agtgtgggtc gccgacacc    1980
agactaagaa cctagaacct cgctggaaag gaccttacac agtcctgctg accacccca    2040
ccgccctcaa agtagacggc atcgcgcttg atacacgcc gcccacgtga aggctgccga    2100
cccccggggg ggaccatcct ctagactgcc ggatctcgag ggatccacca ccatggaccc    2160
ccattaaatt ggaattcctg cagcccgggg gatccactag ttctagagcg aattaattcc    2220
ggttattttc caccatattg ccgtcttttg gcaatgtgag ggcccggaaa cctggccctg    2280
tcttcttgac gagcattcct aggggtcttt ccctctcgc caaggaatg caaggtctgt    2340
tgaatgtcgt gaaggaagca gttcctctgg aagcttcttg aagacaaaca acgtctgtag    2400
cgacccttg caggcagcgg aaccccccac ctggcgacag gtgcctctgc ggccaaaagc    2460
cacgtgtata agatacacct gcaaaggcgg cacaacccca gtgccacgtt gtgagttgga    2520
tagttgtgga aagagtcaaa tggctctcct caagcgtatt caacaagggg ctgaaggatg    2580
cccagaaggt acccccattgt atgggatctg atctggggcc tcggtgcaca tgctttacat    2640
gtgtttagtc gaggttaaaa aacgtctagg ccccccgaac cacggggacg tggttttcct    2700
ttgaaaaaca cgatgataat atgggggatc caccggtcgc caccatggtg agcaagggcg    2760
aggagctgtt caccggggtg gtgcccatcc tggtcgagct ggacggcgac gtaaacggcc    2820
acaagttcag cgtgtccggc gagggcgagg gcgatgccac ctacggcaag ctgaccctga    2880
agttcatctg caccaccggc aagctgcccg tgccctggcc caccctcgtg accaccctga    2940
cctacggcgt gcagtgcttc agccgctacc ccgaccacat gaagcagcac gacttcttca    3000
agtccgccat gcccgaaggc tacgtccagg agcgcaccat cttcttcaag gacgacggca    3060
actacaagac ccgcgccgag gtgaagttcg agggcgacac cctggtgaac cgcatcgagc    3120
tgaagggcat cgacttcaag gaggacggca acatcctggg gcacaagctg gagtacaact    3180
acaacagcca caacgtctat atcatggccg acaagcagaa gaacggcatc aaggtgaact    3240
tcaagatccg ccacaacatc gaggacggca gcgtgcagct cgccgaccac taccagcaga    3300
acaccccat cggcgacggc cccgtgctgc tgcccgacaa ccactacctg agcacccagt    3360
ccgccctgag caaagacccc aacgagaagc gcgatcacat ggtcctgctg gagttcgtga    3420
ccgccgccgg gatcactctc ggcatggacg agctgtacaa gtaaagcggc cgctcgacga    3480
taaaataaaa gatttttattt agtctccaga aaagggggg aatgaaagac ccacctgta    3540
ggtttggcaa gctagcttaa gtaacgccat tttgcaaggc atggaaaaat acataactga    3600
```

-continued

```
gaatagagaa gttcagatca aggtcaggaa cagatggaac agctgaatat gggccaaaca    3660
ggatatctgt ggtaagcagt tcctgccccg gctcagggcc aagaacagat ggaacagctg    3720
aatatgggcc aaacaggata tctgtggtaa gcagttcctg ccccggctca gggccaagaa    3780
cagatggtcc ccagatgcgg tccagccctc agcagtttct agagaaccat cagatgtttc    3840
cagggtgccc caaggacctg aaatgaccct gtgccttatt tgaactaacc aatcagttcg    3900
cttctcgctt ctgttcgcgc gcttctgctc cccgagctca ataaaagagc ccacaacccc    3960
tcactcgggg cgccagtcct ccgattgact gagtcgcccg ggtacccgtg tatccaataa    4020
accctcttgc agttgcatcc gacttgtggt ctcgctgttc cttgggaggg tctcctctga    4080
gtgattgact acccgtcgcg ggggtctttc atttccgact tgtggtctcg ctgccttggg    4140
agggtctcct ctgagtgatt gactacccgt cagcggggt cttcacatgc agcatgtatc    4200
aaaattaatt tggttttttt tcttaagtat ttacattaaa tggccatagt tgcattaatg    4260
aatcggccaa cgcgcgggga gaggcggttt gcgtattggc gctcttccgc ttcctcgctc    4320
actgactcgc tgcgctcgt cgttcggctg cggcgagcgg tatcagctca ctcaaaggcg    4380
gtaatacggt tatccacaga atcaggggat aacgcaggaa agaacatgtg agcaaaaggc    4440
cagcaaaagg ccaggaaccg taaaaaggcc gcgttgctgg cgttttttcca taggctccgc    4500
cccctgacg agcatcacaa aatcgacgc tcaagtcaga ggtggcgaaa cccgacagga    4560
ctataaagat accaggcgtt tccccctgga agctccctcg tgcgctctcc tgttccgacc    4620
ctgccgctta ccggatacct gtccgccttt ctcccttcgg gaagcgtggc gctttctcat    4680
agctcacgct gtaggtatct cagttcggtg taggtcgttc gctccaagct gggctgtgtg    4740
cacgaacccc ccgttcagcc cgaccgctgc gccttatccg gtaactatcg tcttgagtcc    4800
aacccggtaa gacacgactt atcgccactg gcagcagcca ctggtaacag gattagcaga    4860
gcgaggtatg taggcggtgc tacagagttc ttgaagtggt ggcctaacta cggctacact    4920
agaaggacag tatttggtat ctgcgctctg ctgaagccag ttaccttcgg aaaaagagtt    4980
ggtagctctt gatccggcaa acaaaccacc gctggtagcg gtggttttt tgtttgcaag    5040
cagcagatta cgcgcagaaa aaaggatct caagaagatc ctttgatctt ttctacgggg    5100
tctgacgctc agtggaacga aaactcacgt taagggattt tggtcatgag attatcaaaa    5160
aggatcttca cctagatcct tttaaattaa aaatgaagtt tgcgcaaatc aatctaaagt    5220
atatatgagt aaacttggtc tgacagttac caatgcttaa tcagtgaggc acctatctca    5280
gcgatctgtc tatttcgttc atccatagtt gcctgactcc ccgtcgtgta taactacg    5340
atacgggagg gcttaccatc tggccccagt gctgcaatga taccgcgaga cccacgctca    5400
ccggctccag atttatcagc aataaaccag ccagccggaa gggccgagcg cagaagtggt    5460
cctgcaactt tatccgcctc catccagtct attaattgtt gccgggaagc tagagtaagt    5520
agttcgccag ttaatagttt gcgcaacgtt gttgccattg ctacaggcat cgtggtgtca    5580
cgctcgtcgt ttggtatggc ttcattcagc tccggttccc aacgatcaag gcgagttaca    5640
tgatccccca tgttgtgcaa aaaagcggtt agctccttcg gtcctccgat cgttgtcaga    5700
agtaagttgg ccgcagtgtt atcactcatg gttatggcag cactgcataa ttctcttact    5760
gtcatgccat ccgtaagatg cttttctgtg actggtgagt actcaaccaa gtcattctga    5820
gaatagtgta tgcggcgacc gagttgctct tgcccggcgt caacacggga taataccgcg    5880
ccacatagca gaactttaaa agtgctcatc attggaaaac gttcttcggg gcgaaaactc    5940
```

-continued

| | |
|---|---|
| tcaaggatct taccgctgtt gagatccagt tcgatgtaac ccactcgtgc acccaactga | 6000 |
| tcttcagcat cttttacttt caccagcgtt tctgggtgag caaaaacagg aaggcaaaat | 6060 |
| gccgcaaaaa agggaataag ggcgacacgg aaatgttgaa tactcatact cttccttttt | 6120 |
| caatattatt gaagcattta tcaggttatt gtctcatgag cggatacata tttgaatgta | 6180 |
| tttagaaaaa taaacaaata ggggttccgc gcacatttc | 6219 |

<210> SEQ ID NO 5
<211> LENGTH: 5713
<212> TYPE: DNA
<213> ORGANISM: Artificial sequence
<220> FEATURE:
<223> OTHER INFORMATION: synthetic

<400> SEQUENCE: 5

| | |
|---|---|
| atcacgaggc cctttcgtct tcaagaacag ctttgctctt aggagtttcc taatacatcc | 60 |
| caaactcaaa tatataaagc atttgacttg ttctatgccc tagttattaa tagtaatcaa | 120 |
| ttacggggtc attagttcat agcccatata tggagttccg cgttacataa cttacggtaa | 180 |
| atggcccgcc tggctgaccg cccaacgacc cccgcccatt gacgtcaata atgacgtatg | 240 |
| ttcccatagt aacgccaata gggactttcc attgacgtca atgggtggag tatttacggt | 300 |
| aaactgccca cttggcagta catcaagtgt atcatatgcc aagtacgccc cctattgacg | 360 |
| tcaatgacgg taaatggccc gcctggcatt atgcccagta catgacctta tgggactttc | 420 |
| ctacttggca gtacatctac gtattagtca tcgctattac catggtgatg cggttttggc | 480 |
| agtacatcaa tgggcgtgga tagcggtttg actcacgggg atttccaagt ctccacccca | 540 |
| ttgacgtcaa tgggagtttg ttttggcacc aaaatcaacg ggactttcca aaatgtcgta | 600 |
| acaactccgc cccattgacg caaatgggcg gtaggcatgt acgtgggag gtctatataa | 660 |
| gcagagctca ataaaagagc ccacaacccc tcactcgggg cgccagtcct ccgattgact | 720 |
| gagtcgcccg ggtacccgtg tatccaataa accctcttgc agttgcatcc gacttgtggt | 780 |
| ctcgctgttc cttgggaggg tctcctctga gtgattgact acccgtcagc ggggtcttt | 840 |
| catttggggg ctcgtccggg atcgggagac ccctgcccag ggaccaccga cccaccaccg | 900 |
| ggaggtaagc tggccagcaa cttatctgtg tctgtccgat tgtctagtgt ctatgactga | 960 |
| ttttatgcgc ctgcgtcggt actagttagc taactagctc tgtatctggc ggacccgtgg | 1020 |
| tggaactgac gagttcggaa cacccggccg caaccctggg agacgtccca gggacttcgg | 1080 |
| gggccgtttt tgtgccccga cctgagtcca aaaatcccga tcgttttgga ctctttggtg | 1140 |
| cacccccctt agaggaggga tatgtggttc tggtaggaga cgagaaccta aaacagttcc | 1200 |
| cgcctccgtc tgaattttg ctttcggttt gggaccgaag ccgcgccgcg cgtcttgtct | 1260 |
| gctgcagcat cgttctgtgt tgtctctgtc tgactgtgtt tctgtatttg tctgaaaata | 1320 |
| tcggcccggg ccagactgtt accactccct aagtttgac cttaggtcac tggaaagatg | 1380 |
| tcgagcggat cgctcacaac cagtcggtag atgtcaagaa gagacgttgg gttaccttct | 1440 |
| gctctgcaga atggccaacc tttaacgtcg gatggccgcg agacggcacc tttaaccgag | 1500 |
| acctcatcac ccaggttaag atcaaggtct tttcacctgg cccgcatgga cacccagacc | 1560 |
| aggtccccta tcgtgtgacc tgggaagcct tggcttttga ccccctccc tgggtcaagc | 1620 |
| cctttgtaca ccctaagcct ccgcctcctc ttcctccatc cgccccgtct ctcccccttg | 1680 |
| aacctcctcg ttcgacccg cctcgatcct ccctttatcc agccctcact ccttctctag | 1740 |
| gcgccccccat atggccatat gagatcttat atggggcacc ccgccccctt gtaaacttcc | 1800 |

```
ctgaccctga catgacaaga gttactaaca gcccctctct ccaagctcac ttacaggctc    1860
tctacttagt ccagcacgaa gtctggagac ctctggcggc agcctaccaa gaacaactgg    1920
accgaccggt ggtacctcac ccttaccgag tcggcgacac agtgtgggtc cgccgacacc    1980
agactaagaa cctagaacct cgctggaaag gaccttacac agtcctgctg accacccca     2040 ccgcccctcaa gtagacggca tcgcagcttg gatacacgcc gcccacgtga aggctgccga   2100
ccccgggggt ggaccatcct ctagactgcc ggatctcgag ggatccacca tggtgagcaa    2160
gggcgaggag ctgttcaccg gggtggtgcc catcctggtc gagctggacg gcgacgtaaa    2220
cggccacaag ttcagcgtgt ccggcgaggg cgagggcgat gccacctacg gcaagctgac    2280
cctgaagttc atctgcacca ccggcaagct gcccgtgccc tggcccaccc tcgtgaccac    2340
cctgacctac ggcgtgcagt gcttcagccg ctaccccgac cacatgaagc agcacgactt    2400
cttcaagtcc gccatgcccg aaggctacgt ccaggagcgc accatcttct tcaaggacga    2460
cggcaactac aagacccgcg ccgaggtgaa gttcgagggc gacaccctgg tgaaccgcat    2520
cgagctgaag ggcatcgact tcaaggagga cggcaacatc ctggggcaca agctggagta    2580
caactacaac agccacaacg tctatatcat ggccgacaag cagaagaacg gcatcaaggt    2640
gaacttcaag atccgccaca acatcgagga cggcagcgtg cagctcgccg accactacca    2700
gcagaacacc cccatcggcg acggccccgt gctgctgccc gacaaccact acctgagcac    2760
ccagtccgcc ctgagcaaag accccaacga gaagcgcgat cacatggtcc tgctggagtt    2820
cgtgaccgcc gccgggatca ctctcggcat ggacgagctg tacaaggaat cggaggtggg    2880
cagcggtggc ggtcagctgt tgaattttga ccttcttaaa cttgcgggag acgtcgagtc    2940
caaccctggg cccaccacca ccatggaagc ttccattaaa ttggttaacg tcgacgcggc    3000
cgctcgacga taaaataaaa gatttatttt agtctccaga aaaggggggg aatgaaagac    3060
cccacctgta ggtttggcaa gctagcttaa gtaacgccat tttgcaaggc atggaaaaat    3120
acataactga gaatagagaa gttcagatca aggtcaggaa cagatggaac agctgaatat    3180
gggccaaaca ggatatctgt ggtaagcagt tcctgccccg gctcagggcc aagaacagat    3240
ggaacagctg aatatgggcc aaacaggata tctgtggtaa gcagttcctg ccccggctca    3300
gggccaagaa cagatggtcc ccagatgcgg tccagccctc agcagtttct agagaaccat    3360
cagatgtttc cagggtgccc caaggacctg aaatgaccct gtgccttatt tgaactaacc    3420
aatcagttcg cttctcgctt ctgttcgcgc gcttctgctc cccgagctca ataaaagagc    3480
ccacaacccc tcactcgggg cgccagtcct ccgattgact gagtcgcccg ggtacccgtg    3540
tatccaataa accctcttgc agttgcatcc gacttgtggt ctcgctgttc cttgggaggg    3600
tctcctctga gtgattgact acccgtcagc gggggtcttt catttccgac ttgtggtctc    3660
gctgccttgg gagggtctcc tctgagtgat tgactacccg tcagcggggg tcttcacatg    3720
cagcatgtat caaaattaat ttggttttt ttcttaagta tttacattaa atggccatag    3780
ttgcattaat gaatcggcca acgcgcgggg agaggcggtt tgcgtattgg cgctcttccg    3840
cttcctcgct cactgactcg ctgcgctcgg tcgttcggct gcggcgagcg gtatcagctc    3900
actcaaaggc ggtaatacgg ttatccacag aatcagggga taacgcagga agaacatgt    3960 gagcaaaagg ccagcaaaag gccaggaacc gtaaaaaggc cgcgttgctg gcgtttttcc    4020
ataggctccg ccccctgac gagcatcaca aaaatcgacg ctcaagtcag aggtggcgaa    4080
acccgacagg actataagat accaggcgtt tcccctggaa gctccctcg tgcgctctcc    4140
```

```
tgttccgacc ctgccgctta ccggatacct gtccgccttt ctcccttcgg aagcgtggc    4200 gctttctcat agctcacgct gtaggtatct cagttcggtg taggtcgttc gctccaagct    4260
gggctgtgtg cacgaacccc ccgttcagcc cgaccgctgc gccttatccg gtaactatcg    4320
tcttgagtcc aacccggtaa gacacgactt atcgccactg gcagcagcca ctggtaacag    4380
gattagcaga gcgaggtatg taggcggtgc tacagagttc ttgaagtggt ggcctaacta    4440
cggctacact agaaggacag tatttggtat ctgcgctctg ctgaagccag ttaccttcgg    4500
aaaaagagtt ggtagctctt gatccggcaa acaaaccacc gctggtagcg gtggtttttt    4560
tgtttgcaag cagcagatta cgcgcagaaa aaaggatct caagaagatc ctttgatctt    4620
ttctacgggg tctgacgctc agtggaacga aaactcacgt taagggattt tggtcatgag    4680
attatcaaaa aggatcttca cctagatcct tttaaattaa aaatgaagtt tgcgcaaatc    4740
aatctaaagt atatatgagt aaacttggtc tgacagttac caatgcttaa tcagtgaggc    4800
acctatctca gcgatctgtc tatttcgttc atccatagtt gcctgactcc ccgtcgtgta    4860
gataactacg atacgggagg gcttaccatc tggccccagt gctgcaatga taccgcgaga    4920
cccacgctca ccggctccag atttatcagc aataaaccag ccagccggaa gggccgagcg    4980
cagaagtggt cctgcaactt tatccgcctc catccagtct attaattgtt gccgggaagc    5040
tagagtaagt agttcgccag ttaatagttt gcgcaacgtt gttgccattg ctacaggcat    5100
cgtggtgtca cgctcgtcgt ttggtatggc ttcattcagc tccggttccc aacgatcaag    5160
gcgagttaca tgatccccca tgttgtgcaa aaaagcggtt agctccttcg gtcctccgat    5220
cgttgtcaga agtaagttgg ccgcagtgtt atcactcatg gttatggcag cactgcataa    5280
ttctcttact gtcatgccat ccgtaagatg cttttctgtg actggtgagt actcaaccaa    5340
gtcattctga gaatagtgta tgcggcgacc gagttgctct tgcccggcgt caacacggga    5400
taataccgcg ccacatagca gaactttaaa agtgctcatc attggaaaac gttcttcggg    5460
gcgaaaactc tcaaggatct taccgctgtt gagatccagt tcgatgtaac ccactcgtgc    5520
acccaactga tcttcagcat cttttacttt caccagcgtt tctgggtgag caaaaacagg    5580
aaggcaaaat gccgcaaaaa agggaataag ggcgacacgg aaatgttgaa tactcatact    5640 cttcctttt caatattatt gaagcattta tcagggttat tgtctcatga cattaaccta    5700
taaaaatagg cgt                                                       5713
```

<210> SEQ ID NO 6
<211> LENGTH: 4922
<212> TYPE: DNA
<213> ORGANISM: Artificial sequence
<220> FEATURE:
<223> OTHER INFORMATION: synthetic

<400> SEQUENCE: 6

```
atcacgaggc cctttcgtct tcaagaacag ctttgctctt aggagtttcc taatacatcc     60
caaactcaaa tatataaagc atttgacttg ttctatgccc tagttattaa tagtaatcaa    120
ttacggggtc attagttcat agccatatat ggagttccgc gttacataac ttacggtaaa    180
tggcccgcct ggctgaccgc ccaacgaccc ccgcccattg acgtcaataa tgacgtatgt    240
tcccatagta acgccaatag ggactttcca ttgacgtcaa tgggtggagt atttacggta    300
aactgcccac ttggcagtac atcaagtgta tcatatgcca gtacgcccc ctattgacgt    360 caatgacggt aaatggcccg cctggcatta tgcccagtac atgaccttat ggactttcc    420 tacttggcag tacatctacg tattagtcat cgctattacc atggtgatgc ggttttggca    480
```

```
gtacatcaat gggcgtggat agcggtttga ctcacgggga tttccaagtc tccaccccat    540
tgacgtcaat gggagtttgt tttggcacca aaatcaacgg gactttccaa aatgtcgtaa    600
caactccgcc ccattgacgc aaatgggcgg taggcatgta cggtgggagg tctatataag    660
cagagctcaa taaaagagcc cacaacccct cactcggggc gccagtcctc cgattgactg    720
agtcgcccgg gtaccgtgt atccaataaa ccctcttgca gttgcatccg acttgtggtc     780
tcgctgttcc ttgggagggt ctcctctgag tgattgacta cccgtcagcg gggtctttc    840 atttgggggc tcgtccggga tcgggagacc cctgcccagg gaccaccgac ccaccaccgg    900
gaggtaagct ggccagcaac ttatctgtgt ctgtccgatt gtctagtgtc tatgactgat    960
tttatgcgcc tgcgtcggta ctagttagct aactagctct gtatctggcg gacccgtggt    1020
ggaactgacg agttcggaac accggccgc aaccctggga gacgtccag ggacttcggg      1080 ggccgttttt gtggcccgac ctgagtccaa aaatcccgat cgttttggac tctttggtgc    1140
acccccctta gaggagggat atgtggttct ggtaggagac gagaacctaa aacagttccc    1200
gcctccgtct gaattttgc tttcggtttg ggaccgaagc cgcgccgcgc gtcttgtctg     1260
ctgcagcatc gttctgtgtt gtctctgtct gactgtgttt ctgtatttgt ctgaaaatat    1320
cggcccgggc cagactgtta ccactcccct aagtttgacc ttaggtcact ggaaagatgt    1380
cgagcggatc gctcacaacc agtcggtaga tgtcaagaag agacgttggg ttaccttctg    1440
ctctgcagaa tggccaacct ttaacgtcgg atggccgcga gacggcacct ttaaccgaga    1500
cctcatcacc caggttaaga tcaaggtctt ttcacctggc ccgcatggac acccagacca    1560
ggtcccctac atcgtgacct gggaagcctt ggcttttgac ccccctccct gggtcaagcc    1620 cttttgtacac cctaagcctc cgcctcctct tcctccatcc gccccgtctc tccccttga    1680 acctcctcgt tcgacccgc ctcgatcctc cctttatcca gccctcactc cttctctagg     1740
cgcccccata tggccatatg agatcttata tggggcaccc ccgcccccttg taaacttccc   1800 tgaccctgac atgacaagag ttactaacag cccctctctc caagctcact tacaggctct    1860
ctacttagtc cagcacgaag tctggagacc tctggcggca gcctaccaag aacaactgga    1920
ccgaccggtg gtacctcacc cttaccgagt cggcgacaca gtgtgggtcc gccgacacca    1980
gactaagaac ctagaacctc gctggaaagg accttacaca gtcctgctga ccaccccac     2040 cgccctcaag tagacggcat cgcagcttgg atacacgccg cccacgtgaa ggctgccgac    2100
cccgggggtg gaccatcctc tagactgccg gatctcgagg gatccaccac catggacccc    2160
cattaaattg gaattcgggg cccaagcttt gttaacgtcg acgcggccgc cgtcgacgat    2220
aaaataaaag attttatta gtctccagaa aaagggggga atgaaagacc ccacctgtag    2280
gtttggcaag ctagcttaag taacgccatt ttgcaaggca tggaaaaata cataactgag    2340
aatagagaag ttcagatcaa ggtcaggaac agatggaaca gctgaatatg ggccaaacag    2400
gatatctgtg gtaagcagtt cctgccccgg ctcagggcca agaacagatg gaacagctga    2460
atatgggcca aacaggatat ctgtggtaag cagttcctgc cccggctcag ggccaagaac    2520
agatggtccc cagatgcggt ccagccctca gcagtttcta gagaaccatc agatgtttcc    2580
agggtgcccc aaggacctga atgaccctg tgccttattt gaactaacca atcagttcgc     2640
ttctcgcttc tgttcgcgcg cttctgctcc ccgagctcaa taaaagagcc cacaacccct    2700
cactcggggc gccagtcctc cgattgactg agtcgcccgg gtaccgtgt atccaataaa     2760 ccctcttgca gttgcatccg acttgtggtc tcgctgttcc ttgggagggt ctcctctgag    2820
```

```
tgattgacta cccgtcagcg ggggtctttc atttccgact tgtggtctcg ctgccttggg    2880
agggtctcct ctgagtgatt gactacccgt cagcggggt cttcacatgc agcatgtatc    2940
aaaattaatt tggttttttt tcttaagtat ttacattaaa tggccatagt tgcattaatg    3000
aatcggccaa cgcgcgggga gaggcggttt gcgtattggc gctcttccgc ttcctcgctc    3060
actgactcgc tgcgctcggt cgttcggctg cggcgagcgg tatcagctca ctcaaaggcg    3120
gtaatacggt tatccacaga atcagggat aacgcaggaa agaacatgtg agcaaaaggc    3180
cagcaaaagg ccaggaaccg taaaaaggcc gcgttgctgg cgttttttcca taggctccgc    3240 cccctgacg agcatcacaa aaatcgacgc tcaagtcaga ggtggcgaaa cccgacagga    3300
ctataaagat accaggcgtt ccccctgga agctccctcg tgcgctctcc tgttccgacc    3360
ctgccgctta ccggatacct gtccgccttt ctcccttcgg gaagcgtggc gctttctcat    3420
agctcacgct gtaggtatct cagttcggtg taggtcgttc gctccaagct gggctgtgtg    3480
cacgaacccc ccgttcagcc cgaccgctgc gccttatccg gtaactatcg tcttgagtcc    3540
aacccggtaa gacacgactt atcgccactg gcagcagcca ctggtaacag gattagcaga    3600
gcgaggtatg taggcggtgc tacagagttc ttgaagtggt ggcctaacta cggctacact    3660
agaaggacag tatttggtat ctgcgctctg ctgaagccag ttaccttcgg aaaaagagtt    3720
ggtagctctt gatccggcaa acaaaccacc gctggtagcg gtggtttttt tgtttgcaag    3780
cagcagatta cgcgcagaaa aaaggatct caagaagatc ctttgatctt ttctacgggg    3840
tctgacgctc agtggaacga aaactcacgt taagggattt tggtcatgag attatcaaaa    3900
aggatcttca cctagatcct tttaaattaa aaatgaagtt tgcgcaaatc aatctaaagt    3960
atatatgagt aaacttggtc tgacagttac caatgcttaa tcagtgaggc acctatctca    4020
gcgatctgtc tatttcgttc atccatagtt gcctgactcc ccgtcgtgta gataactacg    4080
atacgggagg gcttacatct ggccccagtg ctgcaatgat accgcgagac ccacgctcac    4140
cggctccaga tttatcagca ataaaccagc cagccggaag ggccgagcgc agaagtggtc    4200
ctgcaacttt atccgcctcc atccagtcta ttaattgttg ccgggaagct agagtaagta    4260
gttcgccagt taatagtttg cgcaacgttg ttgccattgc tacaggcatc gtggtgtcac    4320
gctcgtcgtt tggtatggct tcattcagct ccggttccca acgatcaagg cgagttacat    4380
gatcccccat gttgtgcaaa aaagcggtta gctccttcgg tcctccgatc gttgtcagaa    4440
gtaagttggc cgcagtgtta tcactcatgg ttatggcagc actgcataat tctcttactg    4500
tcatgccatc cgtaagatgc ttttctgtga ctggtgagta ctcaaccaag tcattctgag    4560
aatagtgtat gcggcgaccg agttgctctt gcccggcgtc aacacgggat aataccgcgc    4620
cacatagcag aactttaaaa gtgctcatca ttggaaaacg ttcttcgggg cgaaaactct    4680
caaggatctt accgctgttg agatccagtt cgatgtaacc cactcgtgca cccaactgat    4740
cttcagcatc ttttactttc accagcgttt ctgggtgagc aaaaacagga aggcaaaatg    4800
ccgcaaaaaa gggaataagg gcgacacgga aatgttgaat actcatactc ttcctttttc    4860
aatattattg aagcatttat cagggttatt gtctcatgac attaacctat aaaaataggc    4920
gt                                                                 4922
```

<210> SEQ ID NO 7
<211> LENGTH: 8282
<212> TYPE: DNA
<213> ORGANISM: Artificial sequence
<220> FEATURE:
<223> OTHER INFORMATION: synthetic

<400> SEQUENCE: 7

```
atcacgaggc cctttcgtct tcaagaacag ctttgctctt aggagtttcc taatacatcc      60
caaactcaaa tatataaagc atttgacttg ttctatgccc tagttattaa tagtaatcaa     120
ttacggggtc attagttcat agcccatata tggagttccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtgatg cggttttggc     480
agtacatcaa tgggcgtgga tagcggtttg actcacgggg atttccaagt ctccacccca     540
ttgacgtcaa tgggagtttg ttttggcacc aaaatcaacg ggactttcca aatgtcgta     600
acaactccgc cccattgacg caaatgggcg gtaggcatgt acgtgggag gtctatataa     660
gcagagctca ataaaagagc ccacaacccc tcactcgggg cgccagtcct ccgattgact     720
gagtcgcccg ggtacccgtg tatccaataa accctcttgc agttgcatcc gacttgtggt     780
ctcgctgttc cttgggaggg tctcctctga gtgattgact accgtcagc ggggtcttt      840
catttggggg ctcgtccggg atcgggagac ccctgcccag ggaccaccga cccaccaccg     900
ggaggtaagc tggccagcaa cttatctgtg tctgtccgat tgtctagtgt ctatgactga     960
ttttatgcgc ctgcgtcggt actagttagc taactagctc tgtatctggc ggacccgtgg    1020
tggaactgac gagttcggaa cacccggccg caacctggg agacgtccca gggacttcgg    1080
gggccgtttt tgtggcccga cctgagtcca aaaatcccga tcgttttgga ctctttggtg    1140
cacccccctt agaggaggga tatgtggttc tggtaggaga cgagaaccta aaacagttcc    1200
cgcctccgtc tgaatttttg ctttcggttt gggaccgaag ccgcgccgcg cgtcttgtct    1260
gctgcagcat cgttctgtgt tgtctctgtc tgactgtgtt tctgtatttg tctgaaaata    1320
tgggcccggg ccagactgtt accactccct taagtttgac cttaggtcac tggaaagatg    1380
tcgagcggat cgctcacaac cagtcggtag atgtcaagaa gagacgttgg gttaccttct    1440
gctctgcaga atggccaacc tttaacgtcg gatggccgcg agacggcacc tttaaccgag    1500
acctcatcac ccaggttaag atcaaggtct tttcacctgg cccgcatgga cacccagacc    1560
aggtcccta catcgtgacc tgggaagcct ggcttttga ccccctccc tgggtcaagc      1620
cctttgtaca ccctaagcct ccgcctcctc ttcctccatc cgccccgtct ctccccttg     1680
aacctcctcg ttcgaccccg cctcgatcct cccttatcc agccctcact ccttctctag    1740
gcgccccat atggccatat gagatcttat atggggcacc ccgcccctt gtaaacttcc      1800
ctgaccctga catgacaaga gttactaaca gcccctctct ccaagctcac ttacaggctc    1860
tctacttagt ccagcacgaa gtctggagac ctctggcggc agcctaccaa gaacaactgg    1920
accgaccggt ggtacctcac ccttaccgag tcggcgacac agtgtgggtc cgccgacacc    1980
agactaagaa cctagaacct cgctggaaag gaccttacac agtcctgctg accaccccca    2040
ccgccctcaa gtagacggc atcgcagctt ggatacacgc cgcccacgtg aaggctgccg     2100
accccggggg tggaccatcc tctagactgc cggatctcga gggatcctcc ccagcatgcc    2160
tgctattgtc ttcccaatcc tcccccttgc tgtcctgccc caccccaccc ccagaatag    2220
aatgacacct actcagacaa tgcgatgcaa tttcctcatt ttattaggaa aggacagtgg    2280
```

```
gagtggcacc ttccagggtc aaggaaggca cggggggaggg gcaaacaaca gatggctggc    2340
aactagaagg cacagtcgag gtctagcttg ccaaacctac aggtggggtc tttcattccc    2400
ccctttttct ggagactaaa taaaatcttt tattttatcg atagatcccg gtcggcatct    2460
actctattcc tttgccctcg gacgagtgct ggggcgtcgg tttccactat cggcgagtac    2520
ttctacacag ccatcggtcc agacggccgc gcttctgcgg gcgatttgtg tacgcccgac    2580
agtcccggct ccggatcgga cgattgcgtc gcatcgaccc tgcgcccaag ctgcatcatc    2640
gaaattgccg tcaaccaagc tctgatagag ttggtcaaga ccaatgcgga gcatatacgc    2700
ccggagccgc ggcgatcctg caagctccgg atgcctccgc tcgaagtagc gcgtctgctg    2760
ctccatacaa gccaaccacg gcctccagaa gaagatgttg gcgacctcgt attgggaatc    2820
cccgaacatc gcctcgctcc agtcaatgac cgctgttatg cggccattgt ccgtcaggac    2880
attgttggag ccgaaatccg cgtgcacgag gtgccggact tcgggcagt  cctcggccca    2940 aagcatcagc tcatcgagag cctgcgcgac ggacgcactg acgtgtcgt  ccatcacagt    3000 ttgccagtga tacacatggg gatcagcaat cgcgcatatg aaatcacgcc atgtagtgta    3060
ttgaccgatt ccttgcggtc cgaatgggcc gaacccgctc gtctggctaa gatcggccgc    3120
agcgatcgca tccatggcct ccgcgaccgg ctgcagaaca gcgggcagtt cggtttcagg    3180
caggtcttgc aacgtgacac cctgtgcacg gcgggagatg caataggtca ggctctcgct    3240
aaattcccca atgtcaagca cttccggaat cgggagcgcg gccgatgcaa agtgccgata    3300
aacataacga tctttgtaga aaccatcggc gcagctattt acccgcagga catatccacg    3360
ccctcctaca tcgaagctga aagcacgaga ttcttcgccc tccgagagct gcatcaggtc    3420
ggagacgctg tcgaactttt cgatcagaaa cttctcgaca gacgtcgcgg tgagttcagg    3480 cttttttcatg gtattatcat cgtgtttttc aaaggaaaac cacgtccccg tggttcgggg    3540
ggcctagacg ttttttaacc tcgactaaac acatgtaaag catgtgcacc gaggccccag    3600
atcagatccc atacaatggg gtaccttctg ggcatccttc agccccttgt tgaatacgct    3660
tgaggagagc catttgactc tttccacaac tatccaactc acaacgtggc actggggttg    3720
tgccgccttt gcaggtgtat cttatacacg tggcttttgg ccgcagaggc acctgtcgcc    3780
aggtgggggg ttccgctgcc tgcaaagggt cgctacagac gttgtttgtc ttcaagaagc    3840
ttccagagga actgcttcct tcacgacatt caacagacct tgcattcctt tggcgagagg    3900
ggaaagaccc ctagactaga ccaagctttg gatttcattt ctgaagtttg aattttctga    3960
gtcactagta atgtccttga ggatgatagt ctgaattttc tctgcaagag tacaaagatt    4020
ggcttttttg agatctttaa tcaatgtgtc atacgcttct ttctttccat gaagttgatg    4080
ccaattacga agcagttgaa cttctgttc  tgctgtgtct tggacattgt cattcttgat    4140
ctcatctatt ttggcttcat tgacaccatt ctttcgaaca aagcctttaa cttgacttag    4200
tgtcatgact ccagcaatag tggtgatata tttactcaag tcaacatcag ataaattttat   4260 tgccactgtt tcaggattta aggttggaga ttcatgagaa ccttggtttt cctttctgtg    4320 cttttctgcat gttttctgta cttcctttct cttcacccaa acaattagtg gaattggcaa    4380
aagaagaaga caaagccacc ccaaccggtt tctgggactt tgtttcctgc agtttgtatt    4440
gctggttgct gtgcatggct caaggggttcc atgttcacac gaggcgcagc gaacacagtg    4500
ttcacagcca ggagaatcgc agtagaagtc tggtttgcac ttgcacttgg tattctgggt    4560
cagggtgcag tttgtttcca cttctaaacc atgctcttca tcgcagagtg tgcatcttct    4620
gcatttatca gcataatggt tcttgtccat gtactccttc ccttctgtgc atgggcaca    4680
```

-continued

```
ggttggtgta ccccccattca tttttgcagtc ctcaacttttt tttttaccag gttggcatgg    4740
ttgacagcaa aatgggcctc cttgatataa tccttctgag cagttttttat cagtttcatg     4800
aacccgcctc ctcagctttta aactctcgga gatgctatta gtaccttgag tatgaactct     4860
taactgtgag ccagcaagca ccagaggcag acagcccag atccacacca tggtggcttt      4920
accaacagta ccggaatgcc aagcttgcgg ccgcttaaga gctgtaattg aacctgggag     4980
tggacacctg tggagagaaa ggcaaagtgg atgtcagtaa gaccaatagg tgcctatcag     5040
aaacgcaaga gtcttctctg tctcgacaag cccagtttct attggtctcc ttaaacctgt     5100
cttgtaacct tgatacttac ctgcccagtg cctcacgacc aacttctgca ggaattcctg     5160
gacagctccc agatgatcag taaccgtggt tgttatttct gtgccgggca gtggagcctg     5220
ggtaggggga gctctgcctc agtgctttca gctaaaaatg gggtgggaac ccccaggagg     5280
cccgggccgc cctggaagtt ccctttttctc tctgttcttg ggaagtcgat tgagcaacag    5340
cgggggtcag gtgaggctcc ttcactaccg atgcacaccg agtgctgggg gaggttctct    5400
tctctctcag gcccaacccc agggcccctg cctaggtccc ggactctcac tcttgacgca    5460
tgcgtggctt ggtggtccca gtcagcaaac ttggggtccc gttgcctggg aaagggagag    5520
ggtactgggc atcgacgcct ctgcttccac gaaagccttg tgaagaaagg atgggggcgc    5580
ttttgtgcag gagaatgagg cgcactgagg tgaactggcc ctcgggggcg cgtgtcccag    5640
atgtgtgtgc agggcctcct gatggccgca gccctcgtcc ctgtgacccg cttggagctg    5700
gcaccctgag tggtggcctc accttgtact cactcccagg tcactgtcct cgacgcggcc    5760
gctcgacgat aaaataaaag atttttattta gtctccagaa aaaggggggga atgaaagacc    5820
ccacctgtag gtttggcaag ctagcttaag taacccattt tgcaaggcat ggaaaaatac     5880
ataactgaga atagagaagt tcagatcaag gtcggaacag atggaacagg caataaaaga    5940
gcccacaacc cctcactcgg ggcgccagtc ctccgattga ctgagtcgcc cgggtacccg    6000
tgtatccaat aaaccctctt gcagttgcat ccgacttgtg gtctcgctgt tccttgggag    6060
ggtctcctct gagtgattga ctacccgtca gcgggggtct ttcacatgca gcatgtatca    6120
aaattaattt ggttttttttt cttaagtatt tacattaaat ggccatagtt tcgtaatcat    6180
ggtcatagct gtttcctgtg tgaaattgtt atccgctcac aattccacac aacatacgag    6240
ccggaagcat aaagtgtaaa gcctggggtg cctaatgagt gagctaactc acattaattg    6300
cgttgcgctc actgcccgct ttccagtcgg gaaacctgtc gtgccagctg cattaatgaa    6360
tcggccaacg cgcggggaga ggcggtttgc gtattgggcg ctcttccgct tcctcgctca    6420
ctgactcgct gcgctcggtc gttcggctgc ggcgagcggt atcagctcac tcaaaggcgg    6480
taatacggtt atccacagaa tcaggggata acgcaggaaa gaacatgtga gcaaaaggcc    6540
agcaaaaggc caggaaccgt aaaaaggccg cgttgctggc gtttttccat aggctccgcc    6600
cccctgacga gcatcacaaa aatcgacgct caagtcagag gtggcgaaac ccgacaggac    6660
tataaagata ccaggcgttt ccccctggaa gctccctcgt gcgctctcct gttccgaccc    6720
tgccgcttac cggatacctg tccgcctttc tcccttcggg aagcgtggcg ctttctcata    6780
gctcacgctg taggtatctc agttcggtgt aggtcgttcg ctccaagctg ggctgtgtgc    6840
acgaaccccc cgttcagccc gaccgctgcg ccttatccgg taactatcgt cttgagtcca    6900
acccggtaag acacgactta tcgccactgg cagcagccac tggtaacagg attagcagag    6960
cgaggtatgt aggcggtgct acagagttct tgaagtggtg gcctaactac ggctacacta    7020
```

```
gaaggacagt atttggtatc tgcgctctgc tgaagccagt taccttcgga aaaagagttg    7080
gtagctcttg atccggcaaa caaaccaccg ctggtagcgg tggttttttt gtttgcaagc    7140
agcagattac gcgcagaaaa aaggatctc aagaagatcc tttgatcttt tctacgggt     7200 ctgacgctca gtggaacgaa aactcacgtt aagggatttt ggtcatgaga ttatcaaaaa    7260
ggatcttcac ctagatcctt ttaaattaaa aatgaagttt gcgcaaatca atctaaagta    7320
tatatgagta aacttggtct gacagttacc aatgcttaat cagtgaggca cctatctcag    7380
cgatctgtct atttcgttca tccatagttg cctgactccc cgtcgtgtag ataactacga    7440
tacgggaggg cttaccatct ggccccagtg ctgcaatgat accgcgagac ccacgctcac    7500
cggctccaga tttatcagca ataaaccagc cagccggaag ggccgagcgc agaagtggtc    7560
ctgcaacttt atccgcctcc atccagtcta ttaattgttg ccgggaagct agagtaagta    7620
gttcgccagt taatagtttg cgcaacgttg ttgccattgc tacaggcatc gtggtgtcac    7680
gctcgtcgtt tggtatggct tcattcagct ccggttccca acgatcaagg cgagttacat    7740
gatcccccat gttgtgcaaa aaagcggtta gctccttcgg tcctccgatc gttgtcagaa    7800
gtaagttggc cgcagtgtta tcactcatgg ttatggcagc actgcataat tctcttactg    7860
tcatgccatc cgtaagatgc ttttctgtga ctggtgagta ctcaaccaag tcattctgag    7920
aatagtgtat gcggcgaccg agttgctctt gcccggcgtc aacacgggat aataccgcgc    7980
cacatagcag aactttaaaa gtgctcatca ttggaaaacg ttcttcgggg cgaaaactct    8040
caaggatctt accgctgttg agatccagtt cgatgtaacc cactcgtgca cccaactgat    8100
cttcagcatc ttttactttc accagcgttt ctgggtgagc aaaaacagga aggcaaaatg    8160
ccgcaaaaaa gggaataagg gcgacacgga aatgttgaat actcatactc ttcctttttc    8220
aatattattg aagcatttat cagggttatt gtctcatgac attaacctat aaaaataggc    8280
gt                                                                  8282

<210> SEQ ID NO 8
<211> LENGTH: 8345
<212> TYPE: DNA
<213> ORGANISM: Artificial sequence
<220> FEATURE:
<223> OTHER INFORMATION: synthetic

<400> SEQUENCE: 8
atcacgaggc cctttcgtct tcaagaacag ctttgctctt aggagtttcc taatacatcc      60
caaactcaaa tatataaagc atttgacttg ttctatgccc tagttattaa tagtaatcaa     120
ttacggggtc attagttcat agcccatata tggagtccg cgttacataa cttacggtaa     180
atggcccgcc tggctgaccg cccaacgacc cccgcccatt gacgtcaata atgacgtatg     240
ttcccatagt aacgccaata gggactttcc attgacgtca atgggtggag tatttacggt     300
aaactgccca cttggcagta catcaagtgt atcatatgcc aagtacgccc cctattgacg     360
tcaatgacgg taaatggccc gcctggcatt atgcccagta catgacctta tgggactttc     420
ctacttggca gtacatctac gtattagtca tcgctattac catggtgatg cggttttggc     480
agtacatcaa tgggcgtgga tagcggtttg actcacgggg atttccaagt ctccacccca     540
ttgacgtcaa tgggagtttg ttttggcacc aaaatcaacg ggactttcca aaatgtcgta     600
acaactccgc cccattgacg caaatgggcg gtaggcatgt acgtgggag gtctatataa     660 gcagagctca ataaaagagc ccacaacccc tcactcgggg cgccagtcct ccgattgact     720
gagtcgcccg ggtacccgtg tatccaataa accctcttgc agttgcatcc gacttgtggt     780
```

-continued

```
ctcgctgttc cttgggaggg tctcctctga gtgattgact acccgtcagc gggggtcttt    840
catttggggg ctcgtccggg atcgggagac ccctgcccag ggaccaccga cccaccaccg    900
ggaggtaagc tggccagcaa cttatctgtg tctgtccgat tgtctagtgt ctatgactga    960
ttttatgcgc ctgcgtcggt actagttagc taactagctc tgtatctggc ggacccgtgg   1020
tggaactgac gagttcggaa cacccggccg caacccggg agacgtccca gggacttcgg    1080
gggccgtttt tgtggcccga cctgagtcca aaaatcccga tcgttttgga ctctttggtg   1140
cacccccctt agaggaggga tatgtggttc tggtaggaga cgagaaccta aaacagttcc   1200
cgcctccgtc tgaattttg ctttcggttt gggaccgaag ccgcgccgcg cgtcttgtct    1260
gctgcagcat cgttctgtgt tgtctctgtc tgactgtgtt tctgtatttg tctgaaaata   1320
tgggcccggg ccagactgtt accactccct taagtttgac cttaggtcac tggaaagatg   1380
tcgagcggat cgctcacaac cagtcggtag atgtcaagaa gagacgttgg gttaccttct   1440
gctctgcaga atggccaacc tttaacgtcg gatggccgcg agacggcacc tttaaccgag   1500
acctcatcac ccaggttaag atcaaggtct tttcacctgg cccgcatgga cacccagacc   1560
aggtccccta catcgtgacc tgggaagcct tggcttttga cccccctccc tgggtcaagc   1620
cctttgtaca ccctaagcct ccgcctcctc ttcctccatc cgccccgtct ctcccccttg   1680
aacctcctcg ttcgaccccg cctcgatcct ccctttatcc agccctcact ccttctctag   1740
gcgcccccat atggccatat gagatcttat atgggcacc cccgcccctt gtaaacttcc    1800
ctgaccctga catgacaaga gttactaaca gcccctctct ccaagctcac ttacaggctc   1860
tctacttagt ccagcacgaa gtctggagac ctctggcggc agcctaccaa gaacaactgg   1920
accgaccggt ggtacctcac ccttaccgag tcggcgacac agtgtgggtc cgccgacacc   1980
agactaagaa cctagaacct cgctggaaag gaccttacac agtcctgctg accaccccca   2040
ccgcccctcaa agtagacggc atcgcagctt ggatacacgc cgcccacgtg aaggctgccg   2100
accccggggg tggaccatcc tctagactgc cggatctcga gggatcctcc ccagcatgcc   2160
tgctattgtc ttcccaatcc tcccccttgc tgtcctgccc caccccaccc cccagaatag   2220
aatgacacct actcagacaa tgcgatgcaa tttcctcatt ttattaggaa aggacagtgg   2280
gagtggcacc ttccagggtc aaggaaggca cggggaggg gcaaacaaca gatggctggc    2340
aactagaagg cacagtcgag gtctagcttg ccaaacctac aggtgggtc tttcattccc     2400
cccttttct ggagactaaa taaaatcttt tattttatcg atagatcccg gtcggcatct    2460
actctattcc tttgccctcg gacgagtgct ggggcgtcgg tttccactat cggcgagtac   2520
ttctacacag ccatcggtcc agacggccgc gcttctgcgg gcgatttgtg tacgcccgac   2580
agtcccggct ccggatcgga cgattgcgtc gcatcgaccc tgcgcccaag ctgcatcatc   2640
gaaattgccg tcaaccaagc tctgatagag ttggtcaaga ccaatgcgga gcatatacgc   2700
ccggagccgc ggcgatcctg caagctccgg atgcctccgc tcgaagtagc gcgtctgctg   2760
ctccatacaa gccaaccacg gcctccagaa gaagatgttg gcgacctcgt attgggaatc   2820
cccgaacatc gcctcgctcc agtcaatgac cgctgttatg cggccattgt ccgtcaggac   2880
attgttggag ccgaaatccg cgtgcacgag gtgccggact cggggcagt cctcggccca    2940
aagcatcagc tcatcgagag cctgcgcgac ggacgcactg acggtgtcgt ccatcacagt   3000
ttgccagtga tacacatggg gatcagcaat cgcgcatatg aaatcacgcc atgtagtgta   3060
ttgaccgatt ccttgcggtc cgaatgggcc gaacccgctc gtctggctaa gatcggccgc   3120
```

```
agcgatcgca tccatggcct ccgcgaccgg ctgcagaaca gcgggcagtt cggtttcagg    3180
caggtcttgc aacgtgacac cctgtgcacg gcgggagatg caataggtca ggctctcgct    3240
aaattcccca atgtcaagca cttccggaat cgggagcgcg gccgatgcaa agtgccgata    3300
aacataacga tctttgtaga aaccatcggc gcagctattt acccgcagga catatccacg    3360
ccctcctaca tcgaagctga agcacgaga ttcttcgccc tccgagagct gcatcaggtc    3420
ggagacgctg tcgaactttt cgatcagaaa cttctcgaca gacgtcgcgg tgagttcagg    3480 cttttttcatg gtattatcat cgtgtttttc aaaggaaaac cacgtccccg tggttcgggg    3540
ggcctagacg ttttttaacc tcgactaaac acatgtaaag catgtgcacc gaggccccag    3600
atcagatccc atacaatggg gtaccttctg ggcatccttc agcccttgt tgaatacgct    3660 tgaggagagc catttgactc tttccacaac tatccaactc acaacgtggc actgggttg    3720 tgccgccttt gcaggtgtat cttatacacg tggcttttgg ccgcagaggc acctgtcgcc    3780
aggtgggggg ttccgctgcc tgcaaagggt cgctacagac gttgtttgtc ttcaagaagc    3840
ttccagagga actgcttcct tcacgacatt caacagacct tgcattcctt ggcgagagg    3900 ggaaagaccc ctagactaga ccaagctttg gatttcattt ctgaagtttg aattttctga    3960
gtcactagta atgtccttga ggatgatagt ctgaattttc tctgcaagag tacaaagatt    4020
ggcttttttg agatctttaa tcaatgtgtc atacgcttct ttctttccat gaagttgatg    4080
ccaattacga agcagttgaa cttctgttc tgctgtgtct tggacattgt cattcttgat    4140
ctcatctatt ttggcttcat tgacaccatt ctttcgaaca aagcctttaa cttgacttag    4200
tgtcatgact ccagcaatag tggtgatata tttactcaag tcaacatcag ataaatttat    4260
tgccactgtt tcaggattta aggttggaga ttcatgagaa ccttggtttt cctttctgtg    4320 cttctgcat gttttctgta cttcctttct cttcacccaa acaattagtg gaattggcaa    4380
aagaagaaga caaagccacc ccaaccggtt tccggtcccc ttcactgagc cacgggccg    4440 acaatcttct ggtctctggg gctgagatgt cccggtaggg tgcacaggtg agggagttcg    4500
cagcactggc ttggtagtag tagagttcac tttctgaagg actggcacga cagaactgaa    4560
gtacatcacc gagttgctga tgactgagca gaaatagtag ccttcgtttt ccttgctgaa    4620
cttgttcagg gtgagaacgt acttattatt cgtgtccctc atggcagaaa acagtttcga    4680
cgaattcagc ttctcgtccc acgttatctt gttgtgggat gaagccatat agacaacgaa    4740
ggtgggctgg gggagtttgg agctggagtt ctggaagagc caagagcatc cttgcgaaac    4800
ggaccccaac acttcacata ccaggtccac cttctgacca agttcggcgt ccatttctt    4860 tggaaagatt cggagttcgg gtgcctgtgg cttagcttct ccactcccca ggataatcga    4920
ctcacccagc agcagcaggt tcagcgacag aaagcgggtc aacggtgagg ccatggtggc    4980
tttaccaaca gtaccggaat gccaagcttg cggccgctta agagctgtaa ttgaacctgg    5040
gagtggacac ctgtggagag aaaggcaaag tggatgtcag taagaccaat aggtgcctat    5100
cagaaacgca agagtcttct ctgtctcgac aagcccagtt tctattggtc tccttaaacc    5160
tgtcttgtaa ccttgatact tacctgccca gtgcctcacg accaacttct gcaggaattc    5220
ctggacagct cccagatgat cagtaaccgt ggttgttatt tctgtgccgg gcagtggagc    5280
ctgggtaggg ggagctctgc ctcagtgctt tcagctaaaa atgggtgggg aaccccagg    5340 aggcccgggc cgccctggaa gttccctttt ctctctgttc ttgggaagtc gattgagcaa    5400
cagcgggggt caggtgaggc tccttcacta ccgatgcaca ccgagtgctg ggggaggttc    5460
tcttctctct caggcccaac cccagggccc ctgcctaggt cccggactct cactcttgac    5520
```

-continued

```
gcatgcgtgg cttggtggtc ccagtcagca aacttggggt cccgttgcct gggaaaggga      5580
gagggtactg ggcatcgacg cctctgcttc cacgaaagcc ttgtgaagaa aggatggggg      5640
cgcttttgtg caggagaatg aggcgcactg aggtgaactg gccctcgggg gcgcgtgtcc      5700
cagatgtgtg tgcagggcct cctgatggcc gcagccctcg tccctgtgac ccgcttggag      5760
ctggcaccct gagtggtggc ctcaccttgt actcactccc aggtcactgt cctcgacgcg      5820
gccgctcgac gataaaataa aagattttat ttagtctcca gaaaaggggg ggaatgaaag      5880
accccacctg taggtttggc aagctagctt aagtaaccca ttttgcaagg catggaaaaa      5940
tacataactg agaatagaga agttcagatc aaggtcggaa cagatggaac aggcaataaa      6000
agagcccaca acccctcact cggggcgcca gtcctccgat tgactgagtc gcccgggtac      6060
ccgtgtatcc aataaaccct cttgcagttg catccgactt gtggtctcgc tgttccttgg      6120
gagggtctcc tctgagtgat tgactacccg tcagcggggg tctttcacat gcagcatgta      6180
tcaaaattaa tttggttttt tttcttaagt atttacatta aatggccata gtttcgtaat      6240
catggtcata gctgtttcct gtgtgaaatt gttatccgct cacaattcca cacaacatac      6300
gagccggaag cataaagtgt aaagcctggg gtgcctaatg agtgagctaa ctcacattaa      6360
ttgcgttgcg ctcactgccc gctttccagt cgggaaacct gtcgtgccag ctgcattaat      6420
gaatcggcca acgcgcgggg agaggcggtt tgcgtattgg gcgctcttcc gcttcctcgc      6480
tcactgactc gctgcgctcg gtcgttcggc tgcggcgagc ggtatcagct cactcaaagg      6540
cggtaatacg gttatccaca gaatcagggg ataacgcagg aaagaacatg tgagcaaaag      6600
gccagcaaaa ggccaggaac cgtaaaaagg ccgcgttgct ggcgtttttc cataggctcc      6660
gcccccctga cgagcatcac aaaaatcgac gctcaagtca gaggtggcga aacccgacag      6720
gactataaag ataccaggcg tttccccctg gaagctccct cgtgcgctct cctgttccga      6780
ccctgccgct taccggatac ctgtccgcct ttctcccttc gggaagcgtg gcgctttctc      6840
atagctcacg ctgtaggtat ctcagttcgg tgtaggtcgt tcgctccaag ctgggctgtg      6900
tgcacgaacc ccccgttcag cccgaccgct gcgccttatc cggtaactat cgtcttgagt      6960
ccaacccggt aagacacgac ttatcgccac tggcagcagc cactggtaac aggattagca      7020
gagcgaggta tgtaggcggt gctacagagt tcttgaagtg gtggcctaac tacggctaca      7080
ctagaaggac agtatttggt atctgcgctc tgctgaagcc agttaccttc ggaaaaagag      7140
ttggtagctc ttgatccggc aaacaaacca ccgctggtag cggtggtttt tttgtttgca      7200
agcagcagat tacgcgcaga aaaaaggat ctcaagaaga tcctttgatc ttttctacgg      7260
ggtctgacgc tcagtggaac gaaaactcac gttaagggat tttggtcatg agattatcaa      7320
aaaggatctt cacctagatc cttttaaatt aaaaatgaag ttttgcgcaaa tcaatctaaa      7380 gtatatatga gtaaacttgg tctgacagtt accaatgctt aatcagtgag gcacctatct      7440
cagcgatctg tctatttcgt tcatccatag ttgcctgact ccccgtcgtg tagataacta      7500
cgatacggga gggcttacca tctggcccca gtgctgcaat gataccgcga gacccacgct      7560
caccggctcc agatttatca gcaataaacc agccagccgg aagggccgag cgcagaagtg      7620
gtcctgcaac tttatccgcc tccatccagt ctattaattg ttgccgggaa gctagagtaa      7680
gtagttcgcc agttaatagt ttgcgcaacg ttgttgccat tgctacaggc atcgtggtgt      7740
cacgctcgtc gtttggtatg gcttcattca gctccggttc ccaacgatca aggcgagtta      7800
catgatcccc catgttgtgc aaaaaagcgg ttagctcctt cggtcctccg atcgttgtca      7860
```

-continued

```
gaagtaagtt ggccgcagtg ttatcactca tggttatggc agcactgcat aattctctta    7920
ctgtcatgcc atccgtaaga tgcttttctg tgactggtga gtactcaacc aagtcattct    7980
gagaatagtg tatgcggcga ccgagttgct cttgcccggc gtcaacacgg gataataccg    8040
cgccacatag cagaacttta aaagtgctca tcattggaaa acgttcttcg gggcgaaaac    8100
tctcaaggat cttaccgctg ttgagatcca gttcgatgta acccactcgt gcacccaact    8160
gatcttcagc atcttttact ttcaccagcg tttctgggtg agcaaaaaca ggaaggcaaa    8220
atgccgcaaa aaagggaata agggcgacac ggaaatgttg aatactcata ctcttccttt    8280
ttcaatatta ttgaagcatt tatcagggtt attgtctcat gacattaacc tataaaaata    8340
ggcgt                                                                8345
```

<210> SEQ ID NO 9
<211> LENGTH: 61
<212> TYPE: PRT
<213> ORGANISM: Artificial sequence
<220> FEATURE:
<223> OTHER INFORMATION: coiled-coil presentation structure

<400> SEQUENCE: 9

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
            20                  25                  30

Pro Leu Ala Ala Val Lys Ser Lys Leu Ser Ala Val Lys Ser Lys Leu
        35                  40                  45

Ala Ser Val Lys Ser Lys Leu Ala Ala Cys Gly Pro Pro
    50                  55                  60

<210> SEQ ID NO 10
<211> LENGTH: 6
<212> TYPE: PRT
<213> ORGANISM: Artificial sequence
<220> FEATURE:
<223> OTHER INFORMATION: looped structure of coiled-coil presentation
      structure

<400> SEQUENCE: 10

Gly Arg Gly Asp Met Pro
1               5

<210> SEQ ID NO 11
<211> LENGTH: 69
<212> TYPE: PRT
<213> ORGANISM: Artificial sequence
<220> FEATURE:
<223> OTHER INFORMATION: minibody presentation structure

<400> SEQUENCE: 11

Met Gly Arg Asn Ser Gln Ala Thr Ser Gly Phe Thr Phe Ser His Phe
1               5                   10                  15

Tyr Met Glu Trp Val Arg Gly Gly Glu Tyr Ile Ala Ala Ser Arg His
            20                  25                  30

Lys His Asn Lys Tyr Thr Thr Glu Tyr Ser Ala Ser Val Lys Gly Arg
        35                  40                  45

Tyr Ile Val Ser Arg Asp Thr Ser Gln Ser Ile Leu Tyr Leu Gln Lys
    50                  55                  60

Lys Lys Gly Pro Pro
65

```
<210> SEQ ID NO 12
<211> LENGTH: 7
<212> TYPE: PRT
<213> ORGANISM: Simian virus 40

<400> SEQUENCE: 12

Pro Lys Lys Lys Arg Lys Val
1               5

<210> SEQ ID NO 13
<211> LENGTH: 6
<212> TYPE: PRT
<213> ORGANISM: Homo sapiens

<400> SEQUENCE: 13

Ala Arg Arg Arg Arg Pro
1               5

<210> SEQ ID NO 14
<211> LENGTH: 10
<212> TYPE: PRT
<213> ORGANISM: Mus musculus

<400> SEQUENCE: 14

Glu Glu Val Gln Arg Lys Arg Gln Lys Leu
1               5                   10

<210> SEQ ID NO 15
<211> LENGTH: 9
<212> TYPE: PRT
<213> ORGANISM: Mus musculus

<400> SEQUENCE: 15

Glu Glu Lys Arg Lys Arg Thr Tyr Glu
1               5

<210> SEQ ID NO 16
<211> LENGTH: 20
<212> TYPE: PRT
<213> ORGANISM: Xenopus laevis

<400> SEQUENCE: 16

Ala Val Lys Arg Pro Ala Ala Thr Lys Lys Ala Gly Gln Ala Lys Lys
1               5                   10                  15

Lys Lys Leu Asp
            20

<210> SEQ ID NO 17
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 to 6 can be any amino acid.

<400> SEQUENCE: 17

Met Gly Xaa Xaa Xaa Xaa Gly Gly Pro Pro
1               5                   10

<210> SEQ ID NO 18
<211> LENGTH: 5
<212> TYPE: PRT
```

```
-continued

<213> ORGANISM: Artificial sequence
<220> FEATURE:
<223> OTHER INFORMATION: linker sequence

<400> SEQUENCE: 18

Gly Ser Gly Gly Ser
1               5

<210> SEQ ID NO 19
<211> LENGTH: 4
<212> TYPE: PRT
<213> ORGANISM: Artificial sequence
<220> FEATURE:
<223> OTHER INFORMATION: linker sequence

<400> SEQUENCE: 19

Gly Gly Gly Ser
1
```

VECTOR FOR SCREENING FOR MODULATORS OF IGE SYNTHESIS, SECRETION AND SWITCH REARRANGEMENT

This Application is a Continuation of U.S. application Ser. No. 09/076,624, filed May 12, 1998.

FIELD OF THE INVENTION

The invention relates to methods and compositions useful in screening for modulators of IgE synthesis, secretion and switch rearrangement.

BACKGROUND OF THE INVENTION

Immunoglobulins must bind to a vast array of foreign molecules and thus exist in many forms. The sequence of the variable (V) region of immunoglobulin molecules varies tremendously, conferring virtually unlimited capacity to bind antigens. The constant (C) region comes in five different varieties: $\alpha$, $\delta$, $\epsilon$, $\gamma$ and $\mu$, providing five different isotypes: IgA, IgD, IgE, IgG and IgM, each of which performs a different set of functions. B cells initially produce only IgM and IgD, and must be activated or induced to produce the other isoforms, such as IgE.

The course of IgE production starts with the activation of B cells. Upon activation with an antigen, B cells follow one of two differentiation pathways: they may differentiate directly into plasma cells, which are basically antibody-secreting factories, or they may give rise to germinal centers, specialized structures within lymphoid organs. In the latter, successive rounds of mutation of the V region genes is followed by expression of the gene products on the cell surface, with selection of the cells on the basis of the affinity of the mutated immunoglobulins against the antigen.

In both pathways of antigen-induced B cell differentiation, isotype switching occurs in which the C region of the immunoglobulin heavy chain changes from the joint expression of IgM and IgD on naive B cells to expression of one of the downstream isotypes such as IgE. This switching involves the replacement of upstream C regions with a downstream C region that has biologically distinct effector functions without changing the structure of the variable portion and, hence, its specificity. For IgE switching, a deletional rearrangement of the Ig heavy chain gene locus occurs, a rearrangement that joins the switch region of the $\mu$ gene, S$\mu$, with the corresponding region of the $\epsilon$ gene, S$\epsilon$. This switching is minimally induced by IL-4 or IL-13, which initates transcription through the S$\epsilon$ region, resulting in the synthesis of germ-line (or "sterile") $\epsilon$ transcripts; that is, transcripts of the unrearranged $C_\epsilon$ heavy genes. This IL-4 induced transcription is inhibited by IFN-$\gamma$, IFN-$\alpha$, and TGF-$\beta$. A second signal, normally delivered by T cells, is required for actual switch recombination leading to IgE production. The T cell signal may be replaced by monoclonal antibodies to CD40, Epstein-Barr viral infection, or hydrocortisone.

Recently, the mechanism of class switch recombination has been explained by an accessibility model, wherein the specificity of the switch gene rearrangement is determined by the modulation of switch region accessibility; that is, the opening up of the chromatin in certain areas, allowing the required protein/enzyme complexes access to the genes.

IgE antibodies are crucial immune mediators of allergic reactions, and have been shown to be responsible for the induction and maintenance of allergic symptoms. For example, the introduction of anti-IgE antibodies has been shown to interfere with IgE function, thus working to alleviate allergic symptoms. See Jardieu, Current Op. Immunol. 7:779–782 (1995), Shields et al., Int. Arch. Allergy. Immunol. 107:308–312 (1995).

Accordingly, it is an object of the invention to provide compositions and methods useful in screening for modulators of IgE production, in particular for modulators of switch rearrangement.

SUMMARY OF THE INVENTION

In accordance with the objects outlined above, the present invention provides methods of screening for bioactive agents capable of inhibiting an IL-4 inducible $\epsilon$ promoter. The method comprises combining a candidate bioactive agent and a cell comprising a fusion nucleic acid. The fusion nucleic acid comprises an IL-4 inducible $\epsilon$ promoter, and a reporter gene. The promoter is then induced with IL-4 (or IL-13), and the presence or absence of the reporter protein is detected. Generally, the absence of the reporter protein indicates that the agent inhibits the IL-4 inducible $\epsilon$ promoter. The fusion nucleic acid may comprise an exogenous IL-4 inducible $\epsilon$ promoter, or an endogeneous IL-4 inducible $\epsilon$ promoter. Preferred embodiments utilize the use of retroviral vectors to introduce the candidate bioactive agents.

In an additional aspect, the present invention provides cell lines for screening. Either CA-46 and MC-116 cell lines are included, and further comprise fusion nucleic acids comprising an IL-4 inducible $\epsilon$ promoter, and a reporter gene.

In a further aspect, the present invention provides methods of screening for bioactive agents capable of modulating IgE production. The method comprises combining a candidate bioactive agent and a cell capable of expressing IgE and determining the amount of IgE produced in the cell. Generally, a change in the amount of IgE as compared to the amount produced in the absence of the candidate agent indicates that the agent modulates IgE production. The cell can further comprise a IgE fusion protein comprises the $\epsilon$ heavy chain, and a fluorescent protein.

In an additional aspect, the invention provides methods of screening for bioactive agents capable of inhibiting a promoter of interest. The method comprises combining a candidate bioactive agent and a cell comprising a fusion nucleic acid. The fusion nucleic acid comprises a promoter of interest and a reporter gene comprising a death gene that is activated by the introduction of a ligand. The promoter is optionally induced, and the ligand is introduced to the cell. The presence of the cell is then detected, wherein the presence of the cell indicates that the agent inhibits the promoter.

In a further aspect, the invention provides compositions comprising a test vector and a reporter vector. The test vector comprises a first selection gene, and a fusion gene comprising a first sequence encoding a transcriptional activation domain, and a second sequence encoding a test protein. The reporter vector comprises a first detectable gene, and all or part of the switch $\epsilon$ sequence, which upon binding of the transcriptional activation domain due to a protein-nucleic acid interaction between the test protein and the switch $\epsilon$ sequence, will activate transcription of the first detectable gene. Methods utilizing these compositions are also provided; the methods comprise providing a host cell comprising the composition, and subjecting the host cell to conditions under which the fusion gene is expressed to produce a fusion protein. A protein-nucleic acid interaction between the fusion protein and the switch $\epsilon$ sequence is then detected.

BRIEF DESCRIPTION OF THE DRAWINGS

FIGS. 1A and 1B depict the germline $\epsilon$ locus and sequence. FIG. 1A depicts the sequence of the human IL-4 inducible ε promoter (SEQ ID NO: 1). FIG. 1B depicts the organization of the germilne ε locus.

FIGS. 2A and 2B depict the regions (2A) and sequences (2B and 2C; SEQ ID NOS:2&3) of the switch ε (Sε) region that are used in methods of screening for proteins that interact with the Sε region, as described below.

FIG. 3 shows a schematic of the yeast one-hybrid system used to identify proteins that bind to the Sε region.

FIG. 4 depicts the IL-4 induction of germline ε mRNA in three IgM⁺ B cell lines, CA-46, MC-116 and DND39. The cells were incubated for 48 hours in 300 U/ml of hIL-4. RT-PCR ws performed using primiers specific for the germline ε exon and the 5'-end of the ε CH1 exon (predicted size is ~200 bp).

FIGS. 5A, 5B, 5C and 5D depict two general approaches to generate germline ε promoter knock-in reporter cell lines. FIG. 5A shows the organization of this region in vivo. FIGS. 5B and 5C depict two possible knock in constructs. The IL-4 inducible IgM+ B cell lines are transfected with one or both of these constructs. Under the influence of IL-4, GFP and/or BFP positive clones are isolated by FACS. Homologous recombination can be confirmed by PCR and/or Southern blot hybridization. FIG. 5D depicts an alternate construct. In this embodiment, the IL-4 inducible IgM+ B cell lines are transfected with the 5D construct and selected with G418. Survivors are sorted for the lack of the 3' BFP expression (deleted during homologous recombination). RT-PCR is performed to confirm homologous recombination. Those clones are transfected with cre to remove the neomycin resistance gene.

FIG. 7 depicts a general schematic of the generation of the primary peptide libraries in retroviruses.

FIGS. 8A and 8B depict constructs useful in generating ε heavy chain knock-in cell lines. FIG. 8A depicts the wild-type organization. FIG. 8B depicts a representative construct to produce a GFP knock-in. S=secretory exon; GFP=green fluorescent protein; BFP=blue fluorescent protein; Neo$^r$= neomycin resistance gene; VDJ=V region exon; CH1, 2, 3, 4=constant region domain exons; M1, M2=membrane exons; HSV-TK=Herpes Simplex Virus—thymidine kinase.

FIGS. 9A and 9B depict constructs useful in the invention. FIG. 9A shows a reporter construct useful to create an IL-4 inducible ε promoter reporter cell line. CRU5=hCMV pormoter plus R and U5 regions of LTR; BGH poly A=bovine growth hormone poly-adenylation signal; SIN=self-inactivating LTR. FIG. 9B shows a library construct.

FIG. 10 depicts a schematic of the screen for the candidate agents of the germline ε promoter and examples of survival constructs useful in the screen. Position 1 can be a number of different genes, including a FAS chimeric receptor outlined herein (including extracellular mouse Fas receptor or mouse CD8 receptor coupled with the human transmembrane and cytoplasmic Fas receptor), HSV-TK, P450 2B1 and p21 peptide.

FIGS. 11A, 11B and 11C (SEQ ID NOS:4–6) depict preferred vectors and their sequences.

FIGS. 12A, 12B, 12C, and 12D (SEQ ID NO:7) depict a construct useful in the present invention, comprising a Fas survival construct (i.e. the use of a death gene). The sequence is of the inducible ε promoter-chimeric Fas-IRES-hygromycin-bovine growth hormone poly A tail that is put into the C12s vector backwards so that no leaky transcription happens through the cmv promoter.

FIGS. 13A, 13B, 13C, and 13D (SEQ ID NO:8) depict a construct useful in the present invention, comprising a Fas survival construct (i.e. the use of a death gene). The sequence is of the inducible ε promoter-chimeric Fas- (either CD8 or mLyt2)-IRES-hygromycin-bovine growth hormone poly A tail that is put into the C12s vector backwards so that no leaky transcription happens through the cmv promoter.

DETAILED DESCRIPTION OF THE INVENTION

Figure 6:
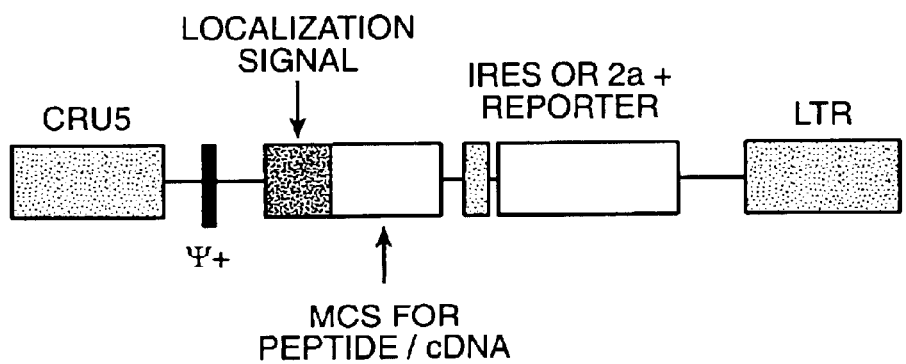
FIG. 6 depicts a preferred vector for introducing a peptide library into cell lines containing knock-in reporter genes under the control of the IL-4 inducible ε promoter. CRU5 is a modified LTR; Naviaux, et al., "The pCL Vector System: Rapid Production of Helper-Free, High-Titer, Recombinant Retroviruses," *Journal of Virology*, 70(8):5701–5705 (1996); LTR=long terminal repeat; ψ+=packaging signal; localization signal=nuclear, cell membrane, etc.; MCS= multiple cloning site; IRES=internal ribosome entry site; 2a=self-cleaving peptide. All the components are cassetted for flexibility.

The present invention provides compositions and methods useful in screening for modulators, particularly inhibitors, of the production of IgE antibodies. In particular, assay methodologies are provided that are amenable to high-throughput screening strategies, such that large numbers of potential drugs may be screened rapidly and efficiently. Generally, traditional treatments for IgE suppression are based on regulation of the system after IgE has been made, for example using anti-IgE antibodies or anti-histamines, to modulate the IgE-mediated response resulting in mast cell degranulation. In some cases, drugs are known that generally downregulate IgE production or that inhibit switching but not induction of germline transcripts (see for example Loh et al., J. Allerg. Clin. Immunol. 97(5):1141 (1996)).

In contrast, the present invention provides several related techniques that may be used to screen for upstream modulators of IgE production, to prevent the production of IgE and thus reduce or eliminate the allergic response. For example, an early step in the Ig switch is the production of sterile ε transcripts in response to IL-4. It is also appreciated that blockage of the production of membrane bound IgE may induce programmed cell death (PCD). By interfering at this step, highly efficient, rapid and prolonged inhibition of the allergic response may occur. In addition, these techniques allow individual cell assessment and thus are useful for high-throughput screening strategies, for example those that utilize fluorescence activated cell sorting (FACS) techniques, and thus allow screening of large numbers of compounds for their effects on IgE production.

In a preferred embodiment, the invention relates to methods that rely on reporter genes fused to IgE promoters, such as the IL-4 inducible ε promoter that starts a cascade that ultimately results in IgE production. Using novel reporter constructs, screening for modulators of this promoter system may be done. Thus the invention provides a number of different constructs that allow for screening for antagonists and agonists of these promoters.

In a preferred embodiment, the invention provides methods of screening for bioactive agents capable of modulating, particularly inhibiting, an IL-4 inducible ε promoter. By "an IL-4 inducible promoter" herein is meant a nucleic acid promoter that is induced by IL-4, putatively by binding an unknown IL-4 induced DNA binding protein that results in induction of the promoter; that is, the introduction of IL-4 causes the pronounced activation of a particular DNA binding protein that then binds to the IL-4 inducible promoter segment and induces transcription. The sequence of the human IL-4 inducible promoter is shown in FIG. 1, and as will be appreciated by those in the art, derivatives or mutant promoters are included within this definition. Particularly included within the definition of an IL-4 inducible promoter are fragments or deletions of the sequence shown in FIG. 1. As is known in the art, the IL-4 inducible promoter is also inducible by IL-13. By "modulating an IL-4 inducible promoter" herein is meant either an increase or a decrease (inhibition) of promoter activity, for example as measured by the presence or quantification of transcripts or of translation products. By "inhibiting an IL-4 inducible promoter" herein is meant a decrease in promoter activity, with changes of at least about 50% being preferred, and at least about 90% being particularly preferred.

The methods comprise combining a candidate bioactive agent and a cell or a population of cells comprising a fusion nucleic acid. The cell or cells comprise a fusion nucleic acid. In a preferred embodiment, the fusion nucleic acid comprises an IL-4 inducible ε promoter and at least a first reporter gene. The IL-4 inducible ε promoter is as described herein, for example SEQ ID NO: 1, or derivatives thereof, and may be either an endogenous or exogenous IL-4 inducible ε promoter, as is more fully described below.

By "reporter gene" or "selection gene" herein is meant a gene that by its presence in a cell (i.e. upon expression) can allow the cell to be distinguished from a cell that does not contain the reporter gene. Reporter genes can be classified into several different types, including detection genes, survival genes, death genes and cell cycle genes. It may be the nucleic acid or the protein expression product that causes the effect. As is more fully outlined below, additional components, such as substrates, ligands, etc., may be additionally added to allow selection or sorting on the basis of the reporter gene.

In a preferred embodiment, the reporter gene encodes a protein that can be used as a direct label, i.e. a detection gene, for sorting the cells, i.e. for cell enrichment by FACS. In this embodiment, the protein product of the reporter gene itself can serve to distinguish cells that are expressing the reporter gene. In this embodiment, suitable reporter genes include those encoding green fluorescent protein (GFP; Chalfie, et al., "Green Fluorescent Protein as a Marker for Gene Expression," *Science* 263(5148):802–805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462–471 (1998); 3. Heim, R. and Tsien, R. Y. Curr. Biol. 6:178–182 (1996)), enhanced yellow fluorescent protein (EYFP; 1. Clontech Laboratories, Inc., 1020 East Meadow Circle, Palo Alto, Calif. 94303), luciferase (Ichiki, et al.), and β-galactosidase (Nolan, et al., "Fluorescence-Activated Cell Analysis and Sorting of Viable Mammalian Cells Based on Beta-D-galactosidase Activity After Transduction of *Escherichia coli* LacZ," *Proc Natl Acad Sci USA* 85(8):2603–2607 (April 1988)).

Alternatively, the reporter gene encodes a protein that will bind a label that can be used as the basis of the cell enrichment (sorting); i.e. the reporter gene serves as an indirect label or detection gene. In this embodiment, the reporter gene should encode a cell-surface protein. For example, the reporter gene may be any cell-surface protein not normally expressed on the surface of the cell, such that secondary binding agents could serve to distinguish cells that contain the reporter gene from those that do not. Alternatively, albeit non-preferably, reporters comprising normally expressed cell-surface proteins could be used, and differences between cells containing the reporter construct and those without could be determined. Thus, secondary binding agents bind to the reporter protein. These secondary binding agents are preferably labelled, for example with fluors, and can be antibodies, haptens, etc. For example, fluorescently labeled antibodies to the reporter gene can be used as the label. Similarly, membrane-tethered streptavidin could serve as a reporter gene, and fluorescently-labeled biotin could be used as the label, i.e. the secondary binding agent. Alternatively, the secondary binding agents need not be labeled as long as the secondary binding agent can be used to distinguish the cells containing the construct; for example, the secondary binding agents may be used in a column, and the cells passed through, such that the expression of the reporter gene results in the cell being bound to the column, and a lack of the reporter gene (i.e. inhibition), results in the cells not being retained on the column. Other suitable reporter proteins/secondary labels include, but are not limited to, antigens and antibodies, enzymes and substrates (or inhibitors), etc.

In a preferred embodiment, the reporter gene is a survival gene that serves to provide a nucleic acid (or encode a protein) without which the cell cannot survive, such as drug resistant genes. In this embodiment, the assays may rely on clonal or pooled populations of cells, since if inhibitors of the promoter are found, the cells will die, necessitating a clonal population in order to determine the candidate agent.

In a preferred embodiment, the reporter gene is a cell cycle gene, that is, a gene that causes alterations in the cell cycle. For example, p21 protein its ligand (a collection of three proteins; see Harper, et al., "The p21 Cdk-Interacting Protein Cip1 Is a Potent Inhibitor of G1 Cyclin-Dependent Kinases," *Cell* 75:805–816 (Nov. 19, 1993)), which does not cause death, but causes cell-cycle arrest, such that cells containing inhibited IL-4 inducible promoters grow out much more quickly, allowing detection on this basis. As will be appreciated by those in the art, it is also possible to configure the system such that the cells containing the inhibited IL-4 inducible promoters do not grow out, and thus can be selected on this basis as well.

In a preferred embodiment, the reporter gene is a death gene that provides a nucleic acid that encodes a protein that causes the cells to die. Death genes fall into two basic categories: death genes that encode death proteins that require a death ligand to kill the cells, and death genes that encode death proteins that kill cells as a result of high expression within the cell, and do not require the addition of any death ligand. It is preferable that cell death requires a two-step process: the expression of the death gene and induction of the death phenotype with a signal or ligand, such that the cells may be grown up expressing the death gene, and then induced to die. A number of death genes/ligand pairs are known, including, but not limited to, the Fas receptor and Fas ligand (Bodmer, et al., "Characterization of Fas," *J Biol Chem* 272(30):18827–18833 (Jul. 25, 1997); muFAS, Gonzalez-Cuadrado, et al., "Agonistic anti-Fas Antibodies Induce Glomerular Cell Apoptosis in Mice In Vivo," *Kidney Int* 51(6): 1739–1746 (June 1997); Muruva, et al., *Hum Gene Ther*, 8(8):955 (May 1997)), (or anti-Fas receptor antibodies); p450 and cyclophosphamide (Chen, et al., "Potentiation of Cytochrome P450/Cyclophosphamide-Based Cancer Gene Therapy By Coexpression of the P450 Reductase Gene," *Cancer Res* 57(21):4830–4837 (Nov. 1, 1997)); thymidine kinase and gangcylovir (Stone, R., "Molecular 'Surgery' For Brain Tumors," 256(5063):1513 (Jun. 12, 1992)), tumor necrosis factor (TNF) receptor and TNF. Alternatively, the death gene need not require a ligand, and death results from high expression of the gene; for example, the overexpression of a number of programmed cell death (PCD) proteins are known to cause cell death, including, but not limited to, caspases, bax, TRADD, FADD, SCK, MEK, etc.

As will be appreciated by those in the art, the use of the death genes in the manner described herein, particularly in two-step applications, allows general and high-throughput screening for inhibitors of other promoters, in addition to the IL-4 inducible ε promoters described herein. Thus, the present invention provides fusion nucleic acids comprising a promoter of interest operably linked to a death gene for use in screening methods. The promoter of interest can be either a constitutive promoter or an inducible promoter, such as the IL-4 inducible ε promoter. As will be appreciated by those in the art, any number of possible promoters could be used. Suitable promoters of interest include, but are not limited to, inducible promoters such as IL-4 ε promoter, promoters that are induced by cytokines or growth factors such as the interferon responsive factors 1 to 4, NFkB (Fiering, et al., "Single Cell Assay of a Transcription Factor Reveals a Threshold in Transcription Activated By Signals Emanating From the T-Cell Antigen Receptor," *Genes Dev* 4(10) :1823–1834 (October 1990)), etc. When inducible promoters are used in this embodiment, suitable cell types are those that can be induced by the appropriate inducer, as will be appreciated by those in the art.

Preferred embodiments fall into one of three configurations. In a preferred embodiment, the promoter of interest is a constitutive promoter, and it is hooked to a death gene that requires the presence of a ligand, such as Fas or TNF. Thus, the cells can be grown up and the presence of the death gene verified due to the constitutive promoter. This is generally done by hooking the death gene up to a detection gene such as GFP or BFP, etc., using either an IRES or a protease cleavage site as is outlined below; thus, the presence of the detection gene means the death gene is also present. Verification of the presence of the death gene is preferred to keep the levels of false positives low; that is, cells that survive the screen should be due to the presence of an inhibitor of the promoter rather than a lack of the death gene.

Once the cells have been enriched for those containing the death gene, the candidate agents can be added (and their presence verified as well), followed by induction in the presence of IL-4, and finally by addition of the death ligand. Thus, the cell population is enriched for those cells that have an agent that inhibits the promoter and thus does not produce the death protein, i.e. those that survive.

Alternatively, a preferred embodiment utilizes fusion nucleic acids comprising promoters of interest that are inducible (such as the IL-4 ε promoter), and hooked to a death gene that requires a death ligand. The presence of the death gene is verified by inducing the promoter, causing the death gene (and preferably a detection gene) to be made. The candidate agents and death ligands are then introduced in the presence of their appropriate inducer, and the population is enriched for those cells that survive, i.e. contain an agent that inhibits the promoter and thus does not produce the death protein.

When death genes that require ligands are used, i.e. for "two step" processes, preferred embodiments utilize chimeric death genes, i.e. chimeric death receptor genes. These chimeric death receptors comprise the extracellular domain of a ligand-activated multimerizing receptor and the endogeneous cytosolic domain of a death receptor gene, such as Fas or TNF. This is done to avoid endogenous activation of the death gene. The mechanism of Fas-induced cell death involves the introduction of the Fas ligand, which can bind two monomeric Fas receptors, causing the multimerization of the receptor, which activates the receptor and leads to secondary signalling resulting in caspase activation and PCD. However, as will be appreciated by those in the art, it is possible to substitute the extracellular portion of the death receptor with the extracellular portion of another ligand-activated multimerizing receptor, such that a completely different signal activates the cell to die. There are a number of known ligand-activated dimerizing receptors, including, but not limited to, the CD8 receptor, erythropoeitin receptor, thrombopoeitin receptor, growth hormone receptor, Fas receptor, platelet derived growth hormone receptor, epidermal growth factor receptor, leptin receptor, and a variety of interleukin receptors (including, but not limited to, IL-1, IL-2, IL-3, IL-4, IL-5, IL-6, IL-7, IL-8, IL-9, IL-11, IL-12, IL-13, IL-15, and IL-17; although the use of the IL-4 and IL-13 receptors are not preferred, since these can be used to induce the promoter and thus does not provide a "two step" death process), low-density lipoprotein receptor, prolactin receptor, and transferrin receptor.

In a preferred embodiment, chimeric Fas receptor genes are made. The exact combination will depend on the cell type used and the receptors normally produced by these cells. For example, when using human cells or cell lines, a non-human extracellular domain and a human cytosolic domain are preferred, to prevent endogeneous induction of the death gene. For example, a preferred embodiment utilizes human cells, a murine extracellular Fas receptor domain and a human cytosolic domain, such that the endogeneous human Fas ligand will not activate the murine domain. Alternatively, human extracellular domains may be used when the cells used do not endogeneously produce the ligand; for example, the human EPO extracellular domain may be used when the cells do not endogeneously produce EPO. (Kawaguchi, et al., *Cancer Lett.*, 116(1):53 (1997); Takebayashi, et al., *Cancer Res.*, 56(18):4164 (1996); Rudert, et al., *Biochem Biophys Res Commun.*, 204(3):1102 (1194); Rudert, et al., *DNA Cell Biol.*, 16(2):197 (1997); Takahasi, et al., *J Biol Chem.* 271(29):17555 (1996); Adam, et al., *J Biol Chem.*, 268(26):19882 (1993); Mares, et al., *Growth Factors*, 6(2):93 (1992); Seedorf, et al., *J Biol Chem.*, 266(19):12424 (1991); Heidaran, et al., *J Biol Chem.*, 265(31):18741 (1990); Okuda, et al., *J Clin Invest.* 100(7):1708 (1997); Allgood, et al., *Curr Opin Biotechnol.*, 8(4):474 (1997); Anders, et al., *J Biol Chem.*, 271(36):21758 (1996); Krishnan, et al., *Oncogene*, 13(1):125 (1996); Declercq, et al., *Cytokine*, 7(7):701 (1995); Bazzoni, et al., *Proc Natl Acad Sci US.*, 92(12):5380 (1995); Ohashi, et al., *Proc Natl Acad Sci USA*, 91(1):158 (1994); Desai, et al., *Cell*, 73(3):541 (1993); and Amara, et al., *Proc Natl Acad Sci USA*, 94(20):10618 (1997)).

In addition to the extracellular domain and the cytosolic domain, these receptors have a transmembrane domain. As will be appreciated by those in the art, for chimeric death receptor genes, the transmembrane domain from any of the receptors can be used, although in general, it is preferred to use the transmembrane domain associated with the chosen cytosolic domain, to preserve the interaction of the transmembrane domain with other endogenous signalling proteins.

Thus, preferred embodiments provide fusion nucleic acids that utilize the IL-4 inducible ε promoter linked to a death gene, particularly a chimeric death receptor gene, that requires a death ligand for cell killing.

Alternatively, inducible promoters can be linked to "one step" death genes, i.e. death genes that upon a certain threshold expression, will kill a cell without requiring a ligand or secondary signal. In this embodiment, the inducible promoter is preferably "leaky", such that some small amount of death gene and a required secondary reporter gene such as a survival gene or a detection gene can be expressed. The cells that contain the death gene can then be selected on this basis, to avoid false positives. Once the presence of the construct is verified, candidate agents are added (and their presence preferably verified, using a detection or selection gene as well), and the promoter is induced. The population is then enriched for those cells that contain agents that inhibit the promoter, i.e. that will survive.

In a preferred embodiment, additional reporter genes are used, particularly when inducible death genes are used. In a preferred embodiment, the additional reporter gene is a selection gene. The cells containing the death gene and the drug selectable gene are grown; if the appropriate drug is added to the culture, only those cells containing the resistance gene (and hence the death gene) survive. This ensures that the cells are expressing the death gene to decrease "false positives", i.e. cells that do not die because they do not contain the death gene.

In an additional preferred embodiment, the additional reporter gene is a labeling gene such as GFP. The use of a detection gene allows cells to be sorted to give a population enriched for those containing the construct. As outlined above, a preferred embodiment uses "leaky" inducible promoters; that is, the cells are selected such that the IL-4 inducible promoter, even in the absence of IL-4 or IL-13, produces some GFP and death gene (for example, the Fas receptor constructs). In this embodiment, suitably "leaky" promoters are chosen such that some GFP is expressed (preferably enough to select the cells expressing the construct from those that are not), but not enough death gene is produced to cause death. While preferred embodiments utilize death genes requiring the addition of a death ligand, it is well known that high levels of some death genes, even in the absence of death ligand, can cause death. Thus, for example, high levels of Fas receptor expression can cause multimerization, and thus activation, even in the absence of the Fas ligand.

In a preferred embodiment, when two reporter genes are used, they are fused together in such a way as to only require a single promoter, and thus some way of functionally separating the two genes is preferred. This can be done on the RNA level or the protein level. Preferred embodiments utilize either IRES sites (which allows the translation of two different genes on a single transcript (Kim, et al., "Construction of a Bifunctional mRNA in the Mouse By Using the Internal Ribosomal Entry Site of the Encephalomycarditis Virus," *Molecular and Cellular Biology* 12(8):3636–3643 (August 1992) and McBratney, et al., "The Sequence Context of the Initiation Codon in the Encephalomycarditis Virus Leader Modulates Efficiency of Internal Translation Initiation," *Current Opinion in Cell Biology* 5:961–965 (1993)), or a protease cleavage site (which cleaves a protein translation product into two proteins).

Preferred protease cleavage sites include, but are not limited to, the 2a site (Ryan et al., J. Gen. Virol. 72:2727 (1991); Ryan et al., EMBO J. 13:928 (1994); Donnelly et al., J. Gen. Virol. 78:13 (1997); Hellen et al., *Biochem*, 28(26) :9881 (1989); and Mattion et al., J. Virol. 70:8124 (1996), all of which are expressly incorporated by reference), proseguences of retroviral proteases including human immunodeficiency virus protease and sequences recognized and cleaved by trypsin (EP 578472, Takasuga et al., J. Biochem. 112(5)652 (1992)) factor $X_a$ (Gardella et al., J. Biol. Chem. 265(26):15854 (1990), WO 9006370), collagenase (J03280893, Tajima et al., J. Ferment. Bioeng. 72(5):362 (1991), WO 9006370), clostripain (EP 578472), subtilisin (including mutant H64A subtilisin, Forsberg et al., J. Protein Chem. 10(5):517 (1991), chymosin, yeast KEX2 protease (Bourbonnais et al., J. Bio. Chem. 263(30):15342 (1988), thrombin (Forsberg et al., supra; Abath et al., Bio Techniques 10(2): 178 (1991)), *Staphylococcus aureus* V8 protease or similar endoproteinase-Glu-C to cleave after Glu residues (EP 578472, Ishizaki et al., Appl. Microbiol. Biotechnol. 36(4):483 (1992)), cleavage by NIa proteainase of tobacco etch virus (Parks et al., Anal. Biochem. 216(2):413 (1994)), endoproteinase-Lys-C (U.S. Pat. No. 4,414,332) and endoproteinase-Asp-N, Neisseria type 2 IgA protease (Pohlner et al., Bio/Technology 10(7):799–804 (1992)), soluble yeast endoproteinase yscF (EP 467839), chymotrypsin (Altman et al., Protein Eng. 4(5):593 (1991)), enteropeptidase (WO 9006370), lysostaphin, a polyglycine specific endoproteinase (EP 316748), and the like. See e.g. Marston, F. A. O. (1986) Biol. Chem. J. 240, 1–12.

In addition to the promoter of interest, such as an IL-4 inducible $\epsilon$ promoter and reporter gene, the fusion nucleic acids may comprise additional components, including, but not limited to, other reporter genes, protein cleavage sites, internal ribosome entry (IRES) sites, AP-1 sites, and other components as will be appreciated by those in the art.

In a preferred embodiment, foreign constructs comprising the IL-4 inducible $\epsilon$ promoter and the reporter gene are made. By "foreign" herein is meant that the fusion nucleic acids originates outside of the cells. That is, a recombinant nucleic acid is made that contains an exogeneous IL-4 inducible $\epsilon$ promoter and a reporter gene. Thus, in some circumstances, the cells will contain both exogeneous and endogeneous IL-4 inducible $\epsilon$ promoters. By "recombinant nucleic acid" herein is meant nucleic acid, originally formed in vitro, in general, by the manipulation of nucleic acid by endonucleases, in a form not normally found in nature. Thus an isolated nucleic acid, in a linear form, a nucleic acid containing components not normally joined, such as an IL-4 inducible promoter and a reporter gene, or an expression vector formed in vitro by ligating DNA molecules that are not normally joined, are all considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention. In this embodiment, any cells that express an IL-4 receptor that transduces the IL-4 signal to the nucleus and alters transcription can be used. Suitable cells include, but are not limited to, human cells and cell lines that show IL-4/13 inducible production of germline $\epsilon$ transcripts, including, but not limited to, DND39 (see Watanabe, supra), MC-116, (Kumar, et al., "Human BCGF-12kD Functions as an Autocrine Growth Factor in Transformed B Cells," *Eur Cytokine Netw* 1(2):109 (1990)), CA-46 (Wang, et al., "UCN-01: A Potent Abrogator of G2 Checkpoint Function in Cancer Cells with Dirupted p53," *J Natl Cancer Inst* 88:956 (1996)).

This recombinant nucleic acid may introduced to a cell in a variety of ways, as will be appreciated by those in the art, including, but not limited to, $CaPO_4$ precipitation, liposome fusion, lipofectin®, electroporation, viral infection, etc. The constructs may preferably stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.).

In a preferred embodiment, the exogeneous constructs, which may be in the form of an expression vector, are added as retroviral constructs, using techniques generally described in PCT US97/01019 and PCT US97/01048, both of which are expressly incorporated by reference, and the examples.

In a preferred embodiment, the fusion construct comprises an endogeneous IL-4 inducible ε promoter and an exogeneous reporter gene; "endogeneous" in this context means originating within the cell. That is, gene "knock-in" constructions are made, whereby an exogeneous reporter gene as outlined herein is added, via homologous recombination, to the genome, such that the reporter gene is under the control of the endogeneous IL-4 inducible ε promoter. This may be desirable to allow for the exploration and modulation of the full range of endogeneous regulation, i.e. regulatory elements (particularly those flanking the promoter) other than just the IL-4 inducible ε promoter fragment. Exemplary constructs are shown in FIGS. 5B and 5C, with GFP and BFP, although other reporter genes outlined herein may be used.

Homologous recombination may proceed in several ways. In one embodiment, traditional homologous recombination is done, with molecular biological techniques such as PCR being done to find the correct insertions. For example, gene "knock-ins" may be done as is known in the art, for example see Westphal et al., Current Biology 7:R530–R533 (1997), and references cited therein, all of which are expressly incorporated by reference. The use of recA mediated systems may also be done, see PCT US93/03868, hereby expressly incorporated by reference.

Alternatively, and preferably, the selection of the "knock ins" are done by FACS on the basis of the incorporation of a reporter gene. Thus, in a preferred embodiment, a first homologous recombination event is done to put a first reporter gene, such as GFP, into at least one allele of the cell genome. Preferably, this is a cell type that exhibits IL-4 inducible production of at least germline ε transcripts, so that the cells may be tested by IL-4 production for reporter gene expression. Suitable cells include, but are not limited to, human cells and cell lines that show IL-4/13 inducible production of germline ε transcripts, including, but not limited to, DND39 (see Watanabe, supra), MC-116, (Kumar, et al., "Human BCGF-12kD Functions as an autocrine Growth Factor in Transformed B Cells," *Eur Cytokine Netw* 1(2):109 (1990)), CA-46 (Wang, et al., "UCN-01 :A Potent Abrogator of G2 Checkpoint Function in Cancer Cells with Dirupted p53," *J Natl Cancer Inst* 88:956 (1996)). As is noted herein, the ability of MC-116 and CA-46 cells to produce germline ε transcripts upon IL-4/13 induction was not known prior to the present invention. Thus, preferred embodiments provide MC-116 and/or CA-46 cells comprising recombinant nucleic acid reporter constructs are outlined herein.

In a preferred embodiment, once a first endogeneous promoter has been combined with an exogeneous reporter construct, a second homologous recombination event may be done, preferably using a second reporter gene different from the first, such as BFP, to target the other allele of the cell genome, and tested as above.

Generally, IL-4 induction of the reporter genes will indicate the correct placement of the genes, which can be confirmed via sequencing such as PCR sequencing or Southern blot hybridization. In addition, preferred embodiments utilize prescreening steps to remove "leaky" cells, i.e. those showing constitutive expression of the reporter gene.

Thus, in a preferred embodiment, the invention provides cell lines that contain fusion nucleic acids comprising IL-4 inducible ε promoter operably connected to at least one reporter gene. Once made, the cell lines comprising these reporter constructs are used to screen candidate bioactive agents for the ability to modulate the production of IgE, as is outlined below.

The term "candidate bioactive agent" or "exogeneous compound" as used herein describes any molecule, e.g., protein, oligopeptide, small organic molecule, polysaccharide, polynucleotide. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occuring proteins or fragments of naturally occuring proteins. Thus, for example, cellular extracts containing proteins, or random or directed digests of proteinaceous cellular extracts, may be used. In this way libraries of procaryotic and eucaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res., 14:3487 (1986); Sawai, et al., Chem. Lett., 805 (1984), Letsinger, et al, J. Am. Chem. Soc., 110:4470 (1988); and Pauwels, et al., Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al., Nature, 380:207 (1996), all of which are incorporated by reference)). Other analog nucleic acids include those with positive backbones (Denpcy, et al., Proc. Natl. Acad. Sci. USA, 92:6097 (1995)); non-ionic backbones (U.S. Pat. Nos. 5,386,023; 5,637,684; 5,602,240; 5,216,141; and 4,469,863; Kiedrowski, et al., Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins, et al., Chem. Soc. Rev., (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occuring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

The candidate bioactive agents are combined or added to a cell or population of cells. Suitable cell types for different embodiments are outlined above. By "population of cells" herein is meant at least two cells, with at least about $10^5$ being preferred, at least about $10^6$ being particularly preferred, and at least about $10^7$, $10^8$ and $10^9$ being especially preferred.

The candidate bioactive agent and the cells are combined. As will be appreciated by those in the art, this may accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins).

In a preferred embodiment, the candidate bioactive agents are either nucleic acids or proteins (proteins in this context includes proteins, oligopeptides, and peptides) that are introduced into the host cells using retroviral vectors, as is generally outlined in PCT US97/01019 and PCT US97/01048, both of which are expressly incorporated by reference. Generally, a library of retroviral vectors is made using retroviral packaging cell lines that are helper-defective and are capable of producing all the necessary trans proteins, including gag, pol and env, and RNA molecules that have in cis the ψ packaging signal. Briefly, the library is generated in a retrovirus DNA construct backbone; standard oligonucleotide synthesis is done to generate either the candidate agent or nucleic acid encoding a protein, for example a random peptide, using techniques well known in the art. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES) that greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in the examples.

The retroviruses may include inducible and constitutive promoters for the expression of the candidate agent (to be distinguished from the IL-4 inducible ε promoter). For example, there are situations wherein it is necessary to induce peptide expression only during certain phases of the selection process. A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment, particularly a nuclear localization sequence (NLS); c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; f) reporter genes (preferably a labeling gene or a survival gene); or g) any combination of a), b), c), d), e), or f) as well as linker sequences as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows: MGCAALESEVSALESEVASLESEVAAL GRGDMPLAAVKSKLSAVKSKLASVKSKLAACGPP (SEQ ED NO:9). The underlined regions represent a coiled-coil leucine zipper region defined previously (see Martin et al., EMBO J. 13(22):5303–5309 (1994), incorporated by reference). The bolded GRGDMP (SEQ ID NO: 10) region represents the loop structure and when appropriately replaced with randomized peptides (i.e. candidate bioactive agents, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a Hindu site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, Kd=$10^{-7}$, for the pro-inflammatory cytokine IL-6.

A preferred minibody presentation structure is as follows: MGRNSQATSGFTFSHFYMEWVRGGEYIAASR HKHNKYTTEYSASVKGRYIVSR DTSQSI- LYLQKKKGPP (SEQ ID NO: 11). The bold, underline regions are the regions which may be randomized. The italicized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence that targets the candidate bioactive agent to a particular subcellular location. As will be appreciated by those in the art, the localization of proteins within a cell is a simple method for increasing effective concentration and determining function. The concentration of a protein can also be simply increased by nature of the localization. Shuttling the proteins into the nucleus confines them to a smaller space thereby increasing concentration. While other targeting sequences such as targeting sequences to the Golgi, endoplasmic reticulum, nuclear membrane, mitochondria, secretory vesicles, lysosome, and cellular membrane may be used, a preferred embodiment uses targeting sequences to the nucleus, i.e. a nuclear localization signal (NLS).

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLSs such as that of the SV40 (monkey virus) large T Antigen (Pro Lys Lys Lys Mg Lys Val (SEQ ID NO: 12)), Kalderon (1984), et al., Cell, 39:499–509; the human retinoic acid receptor-β nuclear localization signal (ARRRRP (SEQ ID) NO:13)); NFκB p50 (EEVQRKRQKL (SEQ ID NO:14); Ghosh et al., Cell 62:1019 (1990); NFκB p65 (EEKRKRTYE (SEQ ID NO: 15); Nolan et al., Cell 64:961 (1991), and others (see for example Boulikas, J. Cell. Biochem. 55(1):32–58 (1994), hereby incorporated by reference) and double basic NLSs exemplified by that of the Xenopus (African clawed toad) protein, nucleoplasmin (Ala Val Lys Mg Pro Ala Ala Thr Lys Lys Ala (My Gin Ala Lys Lys Lys Lys Leu Asp (SEQ ID NO:16)), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dmgwall, and Laskey; Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the His$_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGQO), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows: MG(X)$_n$GGPP (SEQ ID NO:17), where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, 10$^4$) to become large libraries if two peptides per cell are generated which then dimerize, to form an effective library of 10$^8$ (10$^4$×10$^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods.

In a preferred embodiment, the fusion partner is a detection gene, preferably a labeling gene or a survival gene. That is, it is desirable to know that the candidate bioactive agent is a) present and b) being expressed. Thus, preferred embodiments utilize fusion constructs utilizing genes that allow the detection of cells that contain candidate bioactive agents, as is generally outlined in the Examples, and shown in FIG. 10. Preferred detection genes include, but are not limited to, GFP, BFP, YFP, RFP, luciferase, and β-galactosidase. Preferred embodiments utilize detection genes that are different from the reporter genes used to determine whether the IL-4 inducible promoter is inhibited; that is, if a GFP reporter gene is used, preferably a non-GFP detection gene is used. This allows cell enrichment using FACS that can distinguish between cells containing candidate agents and those that do not, as well distinguishing cells containing candidate agents that do not inhibit the promoter and cells containing candidate agents that do inhibit the promoter.

In a preferred embodiment, as for the other constructs outlined herein, when a detection gene fusion partner is used with nucleic acid encoding a peptide candidate agent (which may also include other fusion partners as described herein), the two nucleic acids are fused together in such a way as to only require a single promoter, i.e. using either an IRES site or a protease cleavage site such as 2a. A preferred embodiment is depicted in FIG. 10B.

The fusion partners may be placed anywhere (i.e. N-terminal, C-terminal, internal) in the structure as the biology and activity permits.

In a preferred embodiment, the fusion partner includes a linker or tethering sequence, as generally described in PCT US 97/01019, that can allow the candidate agents to interact with potential targets unhindered. For example, when the candidate bioactive agent is a peptide, useful linkers include glycine-serile polymers (including, for example, (GS)$_n$ (GSGGS)$_n$ (SEQ ID NO:18) and (GGGS)$_n$ (SEQ ID NO:19), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences.

Thus, candidate agents can include these components, and may then be used to generate a library of fragments, each containing a different random nucleotide sequence that may encode a different peptide. The ligation products are then transformed into bacteria, such as *E. coli*, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference. Preferred systems include PhiNX-eco and PhiNX-ampho or similar cell lines, disclosed in PCT US97/01019.

In general, the candidate agents are added to the cells under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away.

A variety of other reagents may be included in the assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Once the candidate agents have been introduced or combined with the cells containing the fusion constructs, the IL-4 inducible ε promoter is induced. Alternatively, the promoter is induced prior to the addition of the candidate bioactive agents, or simultaneously. This is generally done as is known in the art, and involves the addition of IL-4 or IL-13 to the cells at a concentration of not less than 5 units/ml with 200 units/ml being most preferred. Addition of IL-4 or IL-13 is usually 24–48 hours after the bioactive agents are added.

The presence or absence of the reporter gene is then detected. This may be done in a number of ways, as will be appreciated by those in the art, and will depend in part on the reporter gene. For example, cells expressing a label reporter gene, such as GFP, can be distinguished from those not expressing the gene, and preferably sorted (enriched by FACS) on this basis. Similarly, cells expressing the death gene will die, leaving only cells that have inhibited promotion of the expression of the gene, etc. In general, the cells that express the reporter gene (i.e. non-inhibited IL-4 inducible ε promoter) and separated from those that do not (i.e. the IL-4 inducible ε promoter was inhibited). This may be done using FACS, lysis selection using complements, cell cloning, scanning by a Fluorimager, growth under drug resistance, enhanced growth, etc.

In a preferred embodiment, for example when the reporter gene is a death gene, sorting of cells containing bioactive agents that inhibit the IL-4 inducible ε promoter (and thus do not turn on the death gene) from those cells that contain candidate agents that do not inhibit the promoter is simple: only those surviving cells contain such an agent.

In a preferred embodiment, the presence or absence of the reporter gene is determined using a fluorescent-activated cell sorter (FACS). In general, the expression of the reporter gene comprising a label (or allowing the use of a label) is optimized to allow for efficient enrichment by FACS. Thus, for example, in general, 10 to 1000 fluores per sorting event are needed; i.e. per cell, with from about 100 to 1000 being preferred, and from 500 to 1000 being especially preferred. This can be accomplished by amplifying the signal per reporter gene, i.e. have each second label comprise multiple fluores, or by having a high density of reporter genes per cell; or a combination of both.

In a preferred embodiment, the cells are sorted at very high speeds, for example greater than about 5,000 sorting events per sec, with greater than about 10,000 sorting events per sec being preferred, and greater than about 25,000 sorting events per second being particularly preferred, with speeds of greater than about 50,000 to 100,000 being especially preferred. The use of multiple laser paths allows sort accuracy of 1 in $10^6$ with better than 70% accuracy.

The sorting results in a population of cells containing the reporter protein (i.e. the promoter was not inhibited) and at least one population of cells without the reporter protein (i.e. the promoter was inhibited). The absence of the reporter protein is indicative that at least one candidate bioactive agent is a bioactive agent that inhibits the IL-4 inducible ε promoter.

In addition to screening methods utilizing the reporter constructs described above, the invention also provides methods for screening candidate agents for the ability to modulate IgE production. By "modulating IgE production" herein is meant either an increase or a decrease in IgE production, as quantified by the amount of IgE protein made. In this embodiment, cells that have already switched to the ε heavy chain region can no longer be blocked at the earlier phase of IgE production. This is especially important for memory B cells that maintain their capacity to secrete IgE and are long lived. Thus, in this embodiment, candidate agents are screened to identify compounds that can block IgE at the level of ε heavy chain transcription, translation, assembly and trafficking, to prevent the terminal stages of IgE production. In this embodiment, a candidate bioactive agent is combined with a cell capable of expressing IgE, preferably surface IgE. Preferred cells include, but are not limited to, cells that produce surface IgE such as the U266 cell line (Lagging, et al., "Distribution of Plasma Cell Markers and Intracellular IgE in Cell Line U266," *Immunology Letters* 49:71 (1996)).

The candidate agent and the cells are combined, as outlined above, and the cells screened for alterations in the amount of IgE produced, as compared to the amount produced in the absence of the candidate bioactive agent. This may be done using standard IgE labeling techniques, including, but not limited to, the use of anti-IgE antibodies, that may be either directly or indirectly labeled, for example through the use of fluorescent anti-IgE antibodies or fluorescent secondary antibodies, and through the use of IgE fusion proteins, as outlined below.

In a preferred embodiment, the amount of IgE produced is determined through the use of IgE fusion proteins; that is, the IgE is produced as a fusion protein comprising the IgE protein, specifically at least the ε heavy chain, and a detectable protein such as is generally outlined above for label reporter genes. In a preferred embodiment, gene "knock in" cell lines are produced, as outlined above and shown in the Figures. In this embodiment, a first label gene, such as the gene for green fluorescent protein (GFP), is fused to the secretory exon of IgE to label secretory IgE heavy chains green. In a preferred embodiment, a second label gene, such as the gene for blue fluorescent protein (BFP), is attached to the M2 exon to label membrane IgE heavy chains blue. This is preferred as it allows discrimination between mRNA processing and translation of secretory versus membrane ε-heavy chain transcripts. Suitable label genes for this embodiment include, but are not limited to, GFP, BFP, YFP and RFP.

Accordingly, the present invention provides cell lines that produce fusion proteins comprising IgE (either secreted or membrane bound) fused to a label protein, preferably a fluorescent protein.

In yet another preferred embodiment, the invention provides methods of identifying proteins that bind to all or part of the switch ε region (FIG. 2B). The general idea is to use a "one hybrid" system to identify proteins that bind to all or part of the switch ε region. To this end, the present invention provides compositions comprising a test vector and a reporter vector, and cells containing these vectors. These cells may be yeast, such as YM4271 or any yeast cell lines that reporter constructs can be inserted into.

By "vector" or "episome" herein is meant a replicon used for the transformation of host cells. The vectors may be either self-replicating extrachromosomal vectors ("plasmids") or vectors which integrate into a host genome. A preferred embodiment utilizes retroviral vectors, as is more fully described below.

Suitable vectors will depend on the host cells used. For use of the system in yeast, suitable vectors are known in the art and include, but are not limited to, pHisi-1 and pLacZi (Clonetech Cat #K1603-1) (Li, et al., "Isolation of ORC6, A Component of the Yeast Origin of Recognition Complex By a One-Hybrid System," *Science* 262:1870–1873 (1993); Liu, et al. "Identifying DNA-Binding Sites and Analyzing DNA-Binding Domains Using a Yeast Selection System," In: *Methods: A Companion to Methods in Enzymology* 5:125–137 (1993), Luo, et al., "Cloning and Analysis of DNA-Binding Proteins By Yeast One-Hybrid and One-Two-Hybrid Systems," *Biotechniques* 20:564–568 (1996), and Strubin, et al., "OBF-1, A Novel B Cell-Specific Coactivator That Stimulates Immunoglobin Promoter Activity Through Association with Octamer-Binding Proteins," *Cell* 80:497–506 (1995)). Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica*. Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

For non-retroviral mammalian cell embodiments, suitable vectors are derived from any number of known vectors, including, but not limited to, pCEP4 (Invitrogen), pCI-NEO (Promega), and pBI-EGFP (Clontech). Basically, any mammalian expression vectors with strong promoters such as CMV can be used to construct test vectors.

In a preferred embodiment, one or more retroviral vectors are used. Currently, the most efficient gene transfer methodologies harness the capacity of engineered viruses, such as retroviruses, to bypass natural cellular barriers to exogenous nucleic acid uptake. The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins —gag, pol, and env— that are required for packaging, processing, reverse transcription, and integration of recombinant genomes. Those RNA molecules that have in cis the ψ packaging signal are packaged into maturing virions.

Retroviruses are preferred for a number of reasons. First, their derivation is easy. Second, unlike Adenovirus-mediated gene delivery, expression from retroviruses is long-term (adenoviruses do not integrate). Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express. In addition, transfection efficiencies can be extremely high, thus obviating the need for selection genes in some cases.

A particularly well suited retroviral transfection system is described in Mann et al., supra: Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); WO 94/19478; PCT US97/01019, and references cited therein, all of which are incorporated by reference.

Any number of suitable retroviral vectors may be used. Preferred retroviral vectors include a vector based on the murine stem cell virus (MSCV) (see Hawley et al., Gene Therapy 1:136 (1994)) and a modified MFG virus (Rivere et al., Genetics 92:6733 (1995)), and pBABE (see PCT US97/01019, incorporated by reference). Particularly preferred vectors are shown in FIG. 11.

As for the other vectors, the retroviral vectors may include inducible and constitutive promoters. Constitutive promoters are preferred for the bait and test vectors, and include, but are not limited to, CMV, SV40, Srα, RSV, and TK. Similarly, the reporter vector promoter is associated with at least one copy of an operator, as outlined herein.

In addition, it is possible to configure a retroviral vector to allow expression of bait genes or test genes after integration of a bait or test vector in target cells. For example, Tet-inducible retroviruses can be used to express bait or test genes (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

Generally, these expression vectors include transcriptional and translational regulatory nucleic acid operably linked to nucleic acids which are to be expressed. "Operably linked" in this context means that the transcriptional and translational regulatory nucleic acid is positioned relative to any coding sequences in such a manner that transcription is initiated. Generally, this will mean that the promoter and transcriptional initiation or start sequences are positioned 5' to the coding region. The transcriptional and translational regulatory nucleic acid will generally be appropriate to the host cell used, as will be appreciated by those in the art. Numerous types of appropriate expression vectors, and suitable regulatory sequences, are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters, hybrid or synthetic promoters. Hybrid promoters, which combine elements of more than one promoter, are also known in the art, and are useful in the present invention.

In general, the vectors of the present invention utilize two different types of promoters. In a preferred embodiment, the promoters on the bait and test vectors are constitutive, and drive the expression of the fusion proteins and selection genes, if applicable, at a high level. However, it is possible to utilize inducible promoters for the fusion constructs and selection genes, if necessary.

The test vector comprises a selection gene. Selection genes allow the selection of transformed host cells containing the vector, and particularly in the case of mammalian cells, ensures the stability of the vector, since cells which do not contain the vector will generally die. Selection genes are well known in the art and will vary with the host cell used. Suitable selection genes include, but are not limited to, neomycin, blastocidin, bleomycin, puromycin, hygromycin, and other drug resistance genes, as well as genes required for growth on certain media, including, but not limited to, His and Lev or His and Trp. In some cases, for example when using retroviral vectors, the requirement for selection genes is lessened due to the high transformation efficiencies which can be achieved. Accordingly, selection genes need not be used in retroviral constructs, although they can be. In addition, when retroviral vectors are used, the test vectors may also contain detectable genes as are described herein rather than selection genes; it may be desirable to verify that the vector is present in the cell, but not require selective pressure for maintenance.

In addition to the selection gene, the test vector comprises a fusion gene comprising a first sequence encoding a transcriptional activation domain, and a second sequence encoding a test protein. By "fusion gene" or "fusion construct" herein is meant nucleic acid that comprises at least two functionally distinct sequences; i.e. generally sequences from two different genes. As will be appreciated by those in the art, in some embodiments the sequences described herein may be DNA, for example when extrachromosomal plasmids are the vectors, or RNA, for example when retroviral vectors are used. Generally, the sequences are directly linked together without any linking sequences, although in some embodiments linkers such as restriction endonuclease cloning sites or linkers encoding flexible amino acids such as glycine and serine linkers such as are known in the art are used. In a preferred embodiment, the first fusion gene comprises a first sequence encoding a transcriptional activation domain. By "transcriptional activator domain" herein is meant a proteinaceous domain which is able to activate transcription.

Suitable transcription activator domains include, but are not limited to, transcriptional activator domains from GAL4 (amino acids 1–147; see Fields et al., Nature 340:245 (1989), and Gill et al., PNAS USA 87:2127 (1990)), GCN4 (from *S. cerevisiae*, Hope et al., Cell 46:885 (1986)), ARD1 (from *S. cerevisiae*, Thukral et al., Mol. Cell. Biol. 9:2360 (1989)), the human estrogen receptor (Kumar et al., Cell 51:941 (1987)), VP16 (Triezenberg et al., Genes Dev. 2(6) :718–729 (1988)), and B42 (Gyuris et al, Cell 1993), and NF-kB p65, derivatives thereof which are functionally similar.

The fusion nucleic acid also includes a test nucleic acid, encoding a test protein. By "test protein" herein is meant a candidate protein which is to be tested for interaction with a bait protein. Protein in this context means proteins, oligopeptides, and peptides, i.e. at least two amino acids attached. In a preferred embodiment, the test protein sequence is one of a library of test protein sequences; that is, a library of test proteins is tested for binding to one or more bait proteins. The test protein sequences can be derived from genomic DNA, cDNA or can be random sequences. Alternatively, specific classes of test proteins may be tested. The library of test proteins or sequences encoding test proteins are incorporated into a library of test vectors, each or most containing a different test protein sequence.

In a preferred embodiment, the test protein sequences are derived from genomic DNA sequences. Generally, as will be appreciated by those in the art, genomic digests are cloned into test vectors. The genomic library may be a complete library, or it may be fractionated or enriched as will be appreciated by those in the art.

In a preferred embodiment, the test protein sequences are derived from cDNA libraries. A cDNA library from any number of different cells may be used, and cloned into test vectors. As above, the cDNA library may be a complete library, or it may be fractionated or enriched in a number of ways.

In a preferred embodiment, the test protein sequences are random sequences. Generally, these will be generated from chemically synthesized oligonucleotides. Generally, random test proteins range in size from about 2 amino acids to about 100 amino acids, with from about 10 to about 50 amino acids being preferred. Fully random or "biased" random proteins may be used; that is, some positions within the sequence are either held constant or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., for zinc fingers, SH-2 domains, stem loop structures, or to purines, or to reduce the chance of creation of a stop codon, etc.

The compositions of the invention also include reporter vectors. Generally, the test and reporter vectors are distinct, although as will be appreciated by those in the art, one or two independent vectors may be used. The reporter vectors comprise a first detectable or reporter gene and all or part of the switch $\epsilon$ sequence, which functions as an operator site. That is, upon binding of a test protein to the switch $\epsilon$ sequence (i.e. a protein-nucleic acid interaction), the transcriptional activator domain of the fusion protein will activate transcription and cause expression of the selectable or detectable gene(s). Thus, in this embodiment, the test protein functions essentially as a candidate agent.

In a preferred embodiment, the compositions are introduced into host cells to screen for protein-nucleic acid interactions. By "introduced into" or grammatical equivalents herein is meant that the nucleic acids enter the cells in a manner suitable for subsequent expression of the nucleic acid. The method of introduction is largely dictated by the targeted cell type and the composition of the vector. Exemplary methods include $CaPO_4$ precipitation, liposome fusion, lipofectin®, electroporation, viral infection, etc. The vectors may stably integrate into the genome of the host cell (for example, with retroviral introduction for mammalian cells, outlined herein), or may exist either transiently or stably in the cytoplasm (i.e. through the use of traditional plasmids, utilizing standard regulatory sequences, selection markers, etc.).

The vectors can be introduced simultaneously, or sequentially in any order. In a preferred embodiment, host cells containing the reporter construct are generated first, and preferably the reporter vector is integrated into the genome of the host cell, for example, using a retroviral reporter vector. Once the components of the system are in the host cell, the cell is subjected to conditions under which the selectable markers and fusion proteins are expressed. If a test protein has sufficient affinity to the switch ε region to activate transcription, the detectable protein is produced, and cells containing these proteins will survive drug selection and can be detected as outlined above. The detectable protein will be produced at a measurably higher level than in the absence of a protein-nucleic acid interaction. Thus the determination of a protein-nucleic acid interaction is generally done on the basis of the presence or absence of the detectable gene(s).

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, drug selection, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluoroscent one; overgrowth against a background of no or slow growth; death of cells and isolation of DNA or other cell vitality indicator dyes; changes in fluorescent characteristics, etc. The preferred isolation techniques are drug selection and FACS based on the expression of the detectable gene, with a preferred embodiment utilizing both simultaneously.

Once a cell with a protein-nucleic acid interaction is detected and isolated, it is generally desirable to identify the test protein. In a preferred embodiment, the test protein nucleic acid and/or the test protein is isolated from the positive cell. This may be done in a number of ways. In a preferred embodiment, primers complementary to DNA regions common to the vector, or to specific components of the library such as a rescue sequence, are used to "rescue" the unique test sequence. Alternatively, the test protein is isolated using a rescue sequence. Thus, for example, rescue sequences comprising epitope tags or purification sequences may be used to pull out the test protein, using immunoprecipitation or affinity columns. Alternatively, the test protein may be detected using mass spectroscopy.

Once a bioactive agent is identified, a number of things may be done. In a preferred embodiment, the chacterization of the bioactive agent is done. This will proceed as will be appreciated by those in the art, and generally includes an analysis of the structure, identity, binding affinity and function of the agent. Depending on the type of agent, this may proceed in a number of ways. In a preferred embodiment, for example when the candidate agents have been introduced intracellularly using nucleic acid constructs, the candidate nucleic acid and/or the bioactive agent is isolated from the cells. This may be done in a number of ways. In a preferred embodiment, primers complementary to DNA regions common to the retroviral constructs, or to specific components of the library such as a rescue sequence, defined above, are used to "rescue" the unique random sequence. Alternatively, the bioactive agent is isolated using a rescue sequence. Thus, for example, rescue sequences comprising epitope tags or purification sequences may be used to pull out the bioactive agent, using immunoprecipitation or affinity columns. Alternatively, the peptide may be detected using mass spectroscopy.

Once rescued, the sequence of the bioactive agent and/or bioactive nucleic acid is determined. Similarly, candidate agents from other chemical classes can be identified and characterized, for example through the use of mass spectroscopy. This information can then be used in a number of ways.

In a preferred embodiment, the bioactive agent is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference. Other techniques known in the art may be used as well.

In a preferred embodiment, the sequence of a bioactive agent is used to generate more candidate bioactive agents. For example, the sequence of the bioactive agent may be the basis of a second round of (biased) randomization, to develop bioactive agents with increased or altered activities. Alternatively, the second round of randomization may change the affinity of the bioactive agent. Furthermore, it may be desirable to put the identified random region of the bioactive agent into other presentation structures, or to alter the sequence of the constant region of the presentation structure, to alter the conformation/shape of the bioactive agent. It may also be desirable to "walk" around a potential binding site, in a manner similar to the mutagenesis of a binding pocket, by keeping one end of the ligand region constant and randomizing the other end to shift the binding of the peptide around.

Once identified and the biological activity is confirmed, the bioactive agent may be formulated. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Construction of ε Germline GFP/BFP Knock-in Cell Lines

Three different IgM+, EBV− human B cells lines (CA-46, MC116, DND39, FIG. 4) that produce ε germline transcripts in the presence of IL-4 will be transfected with a germline ε GFP or BFP knock-in construct (FIGS. 5B and 5C) and induced with IL-4. The cells will then be sorted by FACS for the appropriate reporter expression, GFP or BFP. Background (i.e. random integration) should be low since the construct must integrate downstream of an IL-4 inducible region in order to be activated. Homologous recombination of the reporter construct will be confirmed in fluorescent clones by genomic PCR using primers located within and immediately flanking the construct. For double knockouts, both GFP and BFP constructs will be transfected and cells sorted for expression of both reporters.

It is possible that activation with IL-4 to identify homologous recombined clones will result in events that move beyond the first phase of ε switching, thus making the clones unusable for a screen identifying blockers of this first step. For this case, we have designed a more traditional construct containing an SV40 promoter-driven neomycin resistance gene which is flanked by loxP sites and inserted in the intron between the first and second ε constant coding exons (FIG. 5D). In addition, attached to the 3' end of the long arm is a BFP reporter gene driven by a constitutive promoter. B cell clones transfected with this construct will be selected for integration by culturing them in the presence of G418. The surviving cells lacking BFP will be sorted by FACS (the BFP at the 3' end will be preferentially deleted during the homologous recombination event). The remaining clones will be assessed for homologous recombination by PCR. Clones containing homologous recombined constructs will be exposed to the cre recombinase protein to mediate excision of the SV40 promoter/neomycin resistance gene in order to eliminate promoter interference and potential ε promoter shutdown. Excision of the SV40 promoter/neomycin resistance gene fragment will be verified by subdividing clones into parent and daughter pools and re-selecting the latter pool in G418. The parental cells corresponding to G418 sensitive daughter cells will be subdivided again and tested for IL-4 inducible GFP expression. Parental stocks of the most inducible clones will be used for subsequent peptide screening. Production of the knock-in cell line using this approach would provide a continuous source of IL-4 inducible cells and would circumvent any down-regulation associated with IL-4 pre-treatment.

Example 2

Creation and Screening of Candidate Bioactive Agents in Knock-in Cell Lines A candidate bioactive agent library, in this case a peptide library, will be packaged into infectious viral particles as outlined below. A preferred library is a mixture of random peptide sequences with and without a nuclear localization sequence (NLS) upstream of a reporter gene to identify infected cells and relative peptide expression (see FIG. 6).

Each screen will start with production of the primary retrovirus peptide library, as is generally shown in FIG. 7. This is generally done as outlined in PCT US97/01019 and PCT US97/01048, both of which are expressly incorporated by reference. In general, this is done as follows. On day 1, the Phoenix cells are seeded in 10 cm plates at 5×106 cells in 6 ml (DMEM+10% FBS+Pen/Strep) per plate the day before transfection. Day 2: allow all reagents to reach room temperature 30 min. before starting. Add 50 mM chloroquine at 8 µl/plate (50 µM final) before preparing the transfection solution. Mix CaPO$_4$ reagents in 15 ml polypropylene tube: per plate: 10 µg DNA, 122 µl 2M CaCl$_2$, 876 µl H$_2$O, 1.0 ml 2×HBS. Add 2×HBS and depress the expulsion button completely to bubble air through the mix for 10 secs. Immediately add mixture gently dropwise to plate. Incubate 3–8 hours. Remove medium and replace with 6.0 ml DMEM-medium. Day 3: Change medium again to 6.0 mls of medium optimal for the cells to be infected. Move to 32° C. either in the morning or afternoon depending on the Phoenix cell confluency and whether you will infect at 48 or 72 hrs after transfection. Day 4 or 5: Collect virus supernatant from transfected plates (6.0 ml) into 50 ml tubes and add protamine sulfate to a final concentration of 5 µg/ml. Pass through a 0.45 µm filter. Count target cells and distribute 10$^7$ cells per 10 cm plate transfected to 50 ml tubes and pellet 5 min. Resuspend each pellet of target cells in virus supernatant and transfer to a 6 well plate at 1.0–1.2 ml per well. Seal plate with parafilm and centrifuge at RT for 30–90 min. at 2500 RPM. Remove parafilm and incubate plate over night at 37° C. Day 5: Collect and pellet each well of target cells. Resuspend in 3 ml medium and transfer back to the same 6well plate. Infection can be repeated by refeeding the Phoenix cells with 6 ml fresh medium and reinfecting the same cells again up to 3 times to increase % of cells infected (for instance at 48, 56, and 72 hours). Day 7 or Day 8: At 48 to 72 hrs. post infection, target cells are ready to analyze for expression.

This primary library will be used to infect at least 10$^9$ knock-in cells. After infection, the cells will be stimulated with IL-4 and two days later, peptide-containing cells (identified by the fluorescent reporter) that are negative for the knock-in reporter (i.e. where there is ε promoter inhibition) will be sorted by FACS. This enriched, knock-in reporter negative population will be subjected to RT-PCR to amplify the integrated peptide sequences. The PCR material will be used to construct a new "enriched" retrovirus peptide library to initiate the next screening round.

It will take approximately 5–7 rounds of enrichment to identify individual sequences capable of inhibiting the germline ε promoter, as outlined below using an iterative screening equation.

$$R = \frac{v}{\varepsilon^\rho + \left(Q + \sum_{i=0}^{\infty} \beta(1+\varepsilon)^\rho\right) + v}$$

The above equation mathematically models screening efficiency and provides a guideline for monitoring enrichment for inhibitory peptides. R=ratio of true positive cells over the total number of cells screened per round of selection; v=frequency of true positive cells (i.e. # of cells expressing peptide inhibitors of IgE switch/synthesis); ε=frequency of non-heritable false-positive cells (i.e. # of cells in which IgE switch/synthesis is inhibited due to stimulation/screening inefficiencies, but are IgE positive in subsequent selection rounds); ρ=number of rounds of selection/enrichment applied to library screen; Q=initial frequency of cells with an heritable false-positive phenotype (i.e. dominant-negative somatic mutation in cells that prevent IgE switch/synthesis); β=frequency of false-positives incurred by or during the selection/enrichment process.

Since we amplify enriched peptides by RT-PCR after each selection round, the equation can be simplified to $$R = \frac{v}{\varepsilon^\rho + Q + v}$$

By plugging in empirically-derived or estimated values for the variables, an estimate of how many selection rounds must be applied to a library before enrichment for IgE inhibitory peptide becomes apparent.

For the purposes of our screens, we engineer and select reporter cell lines in which the values of and Q are low to minimize the number of screening rounds necessary to observe rare positive peptide "hits".

For example, IL-4 treatment upregulates the IgE switch reporter in 97% of cells, therefore ε=0.03. Of the uninduced cells, a second round of stimulation indicates that less than 0.01% of the starting population contain heritable false positives, therefore Q<0.0001. A conservative estimate of IgE inhibitory peptides in the starting population is $1/10^8$, therefore $v \sim 10^{-8}$. Solving the equation for the number of selection rounds required to enrich to 50% true positive hits . . .

$$0.5 = \frac{10^{-8}}{(0.03)^\rho + 10^{-3} + 10^{-8}} \rightarrow \rho = 5 \text{ rounds}$$

The most important factor that influences the number of enrichment rounds necessary to identify individual peptide hits is the ratio between the real positive peptide hits in the original library and the heritable false positives. The frequency of real positive peptide hits is dependent upon the qualitative ability of the peptide to access and, in the correct conformation, bind to regulatory domains on proteins in the pathway of interest. Thus, preferably, multiple scaffolding structures are used for presentation of random peptide surfaces and also different localization sequences fused to those peptide structures. Enrichment of real positive peptides becomes less efficient with false positive rates above 2%. For this reason, great emphasis is placed on developing robust reporter constructs and cell lines.

Uneven RT-PCR amplification may decrease overall amplification of real peptides hits from one round to another. This is overcome by additional rounds of library enrichment and is why RT-PCR amplification is carefully monitored after each round of screening.

Example 3

Screening for Inhibitors of IgE Secretion in Cells that have Already Switched

After B cells have switched to production of IgE, there are several factors that determine when they will secrete IgE. By screening for peptide inhibitors of surface IgE expression, proteins that regulate IgE transcription, translation, assembly and trafficking may be identified.

The IgE$^+$ cell line, U266, expresses IgE on the surface and also secretes IgE. Antibodies against surface IgE heavy and light chains have been obtained and both are used to fluorescently mark IgE positive cells. The U266 line is consistently greater than 98.5% positive for membrane IgE.

Peptide library screening and target identification: The peptide library and enrichment protocols identical to those described in Example 2. As well, peptide hit validation and corresponding target protein identification will be performed as described in Example 2.

Development of an ε-heavy chain GFP/BFP knock-in cell line derivative of U266: The cytoplasmic tail of the ε-heavy chain in U266 cells will be engineered by homologous recombination to encode a GFP/BFP reporter as shown in FIG. 8. This will produce a cell line that is fluorescent when ε-heavy chains are produced. The GFP will be attached to the secretory exon to label secretory IgE heavy chains green. The BFP will be attached to the M2 exon to label membrane IgE heavy chains blue. This will allow discrimination of mRNA processing and translation between secretory versus membrane ε-heavy chain transcripts.

The construct will contain an SV40 promoter-driven neomycin resistance gene which is flanked by loxP sites and inserted in the intron between the CH3 and CH4 exons (FIG. 8). In addition, the HSV-TK gene will be cloned 3' of the longer homologous sequence region. U266 cells transfected with this construct will be selected for integration by culturing them in the presence of G418. The surviving cells will be cultured in ganciclovir to select against cells containing the HSV-TK gene (the HSV-TK gene at the 3' end will be deleted during the desired homologous recombination event). The remaining clones will be assessed for homologous recombination by PCR. Clones containing homologously-recombined constructs will be transfected with cre to mediate excision of the SV40 promoter/neomycin resistance gene in order to eliminate promoter interference. Excision will be verified by subdividing clones into parent and daughter pools and re-selecting the latter pool in G418. The parental cells corresponding to G418 sensitive daughter cells will be subdivided again and tested for GFP and BFP expression. Parental stocks of the most inducible clones will be used for of subsequent screening.

Example 4

Development of an ε Promoter GFP Reporter Cell Line

The induction of the ε promoter in response to IL-4/13 is the first recognizable step necessary for the switch to IgE. Blocking activation of this promoter should prevent B cells from switching to IgE. Inhibitors are predicted to interfere with IL-4/13 signaling as well as nuclear transcription of the ε germline gene.

Three IgM$^+$, EBV$^-$ human B cells lines (CA-46, MC116, and DND39; see FIG. 4) that produce ε germline transcripts in the presence of IL-4 will be infected with the following construct: a retroviral vector containing an IL-4 responsive 600 bp fragment of the ε promoter in the reverse orientation followed by a splice site, GFP encoding sequence and a poly-adenylation sequence (FIG. 10). Briefly, cells will be infected with the reporter construct and induced with IL-4. The cells will then be sorted by FACS for GFP reporter expression. The IL-4 will be removed and the cells will be sorted for the absence of reporter fluorescence. From these sorts, several clones will be established that turn on the reporter in the presence of IL-4, indicating activation of the germline ε promoter.

Example 5

Screening of Candidate Agents using Reporter Cell Line

The cell line of Example 4 is infected infected with a peptide library as described above. The peptide library is packaged into infectious viral particles (see FIG. 7). The library is a mixture of random peptide sequences with and without a nuclear localization sequence (NLS) upstream of a reporter gene to identify infected cells and relative peptide expression (FIG. 6).

Each screen will start with production of the primary retrovirus peptide library. This primary library will be used to infect at least $10^9$ ε promoter reporter cells. After infection, the cells will be stimulated with IL-4 and two days later, the FACS will sort peptide-containing, reporter negative cells (i.e. where there is ε promoter inhibition). This enriched, reporter negative population will be subjected to RT-PCR to amplify the integrated peptide sequences. The PCR material will be used to construct a new "enriched" retrovirus peptide library to initiate the next screening round.

It will take approximately 5–7 rounds of enrichment to identify individual sequences capable of inhibiting the germline ε promoter (see discussion above regarding the statistics associated with enrichment). The most important factor that influences the number of enrichment rounds necessary to identify individual peptide hits is the ratio between real positive peptide hits in the original library and heritable false positives. The frequency of real positive peptide hits is dependent upon the qualitative ability of the peptide to get to and, in the correct conformation, bind to the regulatory domains on proteins in the pathway of interest. This is why we use multiple scaffolding structures for presentation of random peptide surfaces and also different localization sequences fused to those peptide structures (Appendix B). Enrichment of real positive peptides becomes less efficient with false positive rates above 2%. For this reason, great effort is placed in developing robust reporter constructs and cell lines.

Once enrichment is achieved and individual peptide sequences are shown to effect inhibition of ε promoter activation in an independent assay, they will be introduced into a standard set of secondary and orthogonal assays. Many of these assays will be performed in primary B cells to test the specificity and physiologic characteristics of the peptide inhibitor.

Example 6

Generation of an ε Promoter Survival Cell Line

Three different IgM+, EBV− human B cells lines that produce ε germline transcripts in the presence of IL-4 will be infected with a survival construct carrying a death gene and a drug selectable marker (FIG. 10). Briefly, the retroviral construct consists of the 600 bp IL-4 inducible ε promoter downstream of a self-inactivating (SIN) LTR, followed by a chimeric FAS receptor (FASr), the self-cleaving peptide 2a and, lastly, the drug-selectable puromycin resistance gene. The chimeric receptor is composed of the mouse FASr external domain and the human FASr transmembrane and cytoplasmic domains. A mouse specific anti-FASr antibody can be used which will bind only activated FASr produced by the survival construct. The 2a self-cleaving peptide allows equimolar amounts of the chimeric FASr and puromycin to be produced in the cell.

IgM+ B cell lines infected with this construct in the presence of IL-4 will produce CD95, as well as puromycin resistance. Upon drug selection with puromycin, only cells containing IL-4 activated ε promoters will survive. The remaining cells are infected with the peptide libraries and, when cultured in the presence of IL-4 and anti-FAS ((αCD95) monoclonal antibodies, will express the chimeric FAS receptor and apoptose unless their ε promoter has been blocked by a library peptide.

If problems arise due to over-expression of the chimeric FASr resulting in self-activation, other external domains will be used. We have already engineered a chimeric FASr containing the murine CD8 external domain as an alternative (FIG. 10). If overexpression of the chimeric FASr results in self-activation, we have designed an alternative strategy in which the proposed construct contains the GFP gene in lieu of the puromycin resistance gene (FIG. 10). Due to the mild transcriptional leakiness inherent to all SIN retroviral vectors, a small percentage of IgM+ B cell clones infected with this construct will express low, detectable levels of GFP. These cells can be single-cell cloned by FACS, split into parent and daughter pools and tested for IL-4 inducible FASr expression-dependent apoptosis. Parent stocks of the most efficiently killed daughter cells will provide a continuous cell source for subsequent peptide screening assays. In addition, FASr ligation can be used to potentiate cell death and thus diminish background cell survival.

Additionally, IL-4 stimulation has been reported to diminish FAS-induced apoptosis in certain B-cell lines. To circumvent this potential difficulty, common suicide genes including Herpes Simplex Virus Thymidine Kinase (HSV-TK) or human cytochrome P450 2B1 in conjunction with ganciclovir or cyclophosphamide treatment, respectively, can replace FASr-mediated death (FIG. 10). Alternatively, cell cycle arrest genes such as p21 can be used in place of toxic gene products (FIG. 10). In this way, cells expressing peptides which prevent IL-4 induced overexpression of p21 will have a selective growth advantage and will quickly dominate the culture.

Example 7

Screening in ε Promoter Survival Cells

Using a peptide library generated as outlined above, the IgM+ B cell lines described in Example 6 are infected with the survival construct. Leaky cells (constitutive expression of the ε promoter) will be removed by incubation with the anti-mouse FASr antibody. Next, the cells are incubated in the presence of the inducer, IL-4, and the drug selection compound, puromycin. Cells that contain a construct that is inducible by IL-4 will be resistant and survive. This produces a population with an exogenous ε promoter that is IL-4 inducible. The peptide library is introduced into these cells and two days later they are induced with IL-4 in the presence of anti-mouse FASr monoclonal antibody. Cells carrying peptides that inhibit induction of the engineered ε promoter fragment will not produce the chimeric FASr and will survive. After the survivors grow out (approximately 1 week), they will again be subjected to IL-4 and the anti-FASr treatment. The genes encoding the peptides responsible for the survivors will be rescued by RT-PCR and used to generate an enriched retroviral library. The identification of individual inhibitory peptides should occur in only 3–4 rounds since the false positive background for survival screens is lower than for FACS-based screening. Once enrichment is achieved and individual peptide sequences are independently shown to inhibit ε promoter activation, these sequences will be introduced into a standard set of secondary and orthogonal assays.

Example 8

One-hybrid Screens for Identification of Proteins that Bind to Switch ε Region

Recombinase proteins that bind to the Sε region mediate the DNA rearrangement that generates a functional ε heavy chain. They may be specific for ε switching cells or may bind to other proteins that target them specifically to the Sε region. Breakpoints in the recombination of the switch ε region to the switch μ region occur in a limited area of the switch ε region. Two stretches of the switch ε region spanning the majority of breakpoints will be used as bait in a one-hybrid screen (FIG. 2b). The cDNA libraries to be used are derived from the IgE positive cell line U266 (the assumption here is that the U266 line still contains the switch recombinase; certainly, the recombinase is turned off in plasma cells) and from human peripheral blood lymphocytes stimulated in vitro to switch with a high frequency to IgE.

The screening is summarized in FIG. 3. The methods are as follows: Two stretches of the switch ε region were cloned (FIG. 2A) into EcoR I/Xba I sites of pHISi-1 (Clontech) to construct a HIS reporter vector pIgE-HIS. In this construct, HIS expression is under the control of a minimal promoter and proteins binding to the switch ε region. Similarly, a second LacZ reporter is constructed by inserting two stretches of switch ε region into the EcoR I/Xho I sites of pLacZi to construct pIgE-LacZ.

The pIgE-HIS was linearized at an Afl II site and integrated into yeast strain YM4271 (MATa, ura3-52, his3-200, ade2-101, lys2-801, leu2-3, 112, trpl-901, tyrl-501, gal4-Δ512, gal80-Δ538, ade5::hisG) to construct the first yeast reporter strain YIgE-HIS. SD-H plates were used to select for integrated reporters. The yeast strain YIgE-HIS was tested on SD-H+3AT plates to determine the optimal concentration of 3AT to suppress basal level HIS expression from the minimal promoter.

The pIgE-LacZ plasmid was linearized at an Nco I site and integrated into the yeast strain YIgE-HIS to construct a dual reporter strain YIgE-HL. SD-U plates were used to select for cells with dual reporters integrated. The dual reporter strain will be used for transformation by the U266 cDNA library (it is assumed that the U266 line still contains the switch recombinase) and the IgE switching PBL cDNA library. At least 20 million transformants from each library will be screened on SD-LH+3AT plates. Clones that can grow up and turn blue on SD-LH+3AT plates will be grown up in SD-L liquid medium for plasmid retrieval. Retrieved cDNA clones will be further tested using in vitro binding assays.

We claim:

1. A retroviral vector comprising a fusion nucleic acid comprising:
   i) a promoter of interest, wherein said promoter of interest is an IL-4 inducible ε promoter comprising the sequence set forth as SEQ ID NO:1;
   ii) a first reporter gene; and
   iii) a second reporter gene, wherein the promoter is operably linked to the first reporter gene and the first and second reporter genes are fused, such that transcription from the promoter results in a single transcript encoding the first and second reporter genes, and further comprising a site which allows for functional separation of the two reporter genes, wherein the site is a protease cleavage site.

2. A vector according to claim 1 wherein one of said reporter genes is a death gene.

3. A vector according to claim 1 wherein one of said reporter genes is a drug resistance gene.

4. A vector according to claim 1, wherein said protease cleavage site is a 2a site.

5. A vector according to claim 1 wherein one of said reporter genes encodes a fluorescent protein.

6. A vector according to claim 5, wherein said fluorescent protein is a blue fluorescent protein (BFP).

7. A vector according to claim 5, wherein said fluorescent protein is a yellow fluorescent protein (YFP).

8. A vector according to claim 5, wherein said fluorescent protein is a red fluorescent protein (RFP).

9. A vector according to claim 2 wherein said death gene encodes a Fas receptor.

10. A vector according to claim 5 wherein said fluorescent protein is a green fluorescent protein (GFP).

* * * * *